(12) United States Patent
Sun

(10) Patent No.: US 8,703,152 B2
(45) Date of Patent: Apr. 22, 2014

(54) METHODS OF TREATING INFLAMMATORY INTESTINAL DISEASE AND MANAGING SYMPTOMS THEREOF

(75) Inventor: Jun Sun, Rochester, NY (US)

(73) Assignee: University of Rochester, Rochester, NY (US)

( * ) Notice: Subject to any disclaimer, the term of this patent is extended or adjusted under 35 U.S.C. 154(b) by 368 days.

(21) Appl. No.: 12/996,166

(22) PCT Filed: Jun. 3, 2009

(86) PCT No.: PCT/US2009/046142
§ 371 (c)(1),
(2), (4) Date: Mar. 28, 2011

(87) PCT Pub. No.: WO2009/149191
PCT Pub. Date: Dec. 10, 2009

(65) Prior Publication Data
US 2011/0178030 A1      Jul. 21, 2011

Related U.S. Application Data

(60) Provisional application No. 61/058,421, filed on Jun. 3, 2008.

(51) Int. Cl.
| | |
|---|---|
| *A61K 39/112* | (2006.01) |
| *A61K 39/00* | (2006.01) |
| *A61K 39/38* | (2006.01) |
| *A61K 39/02* | (2006.01) |
| *A61K 45/00* | (2006.01) |
| *A61K 47/00* | (2006.01) |
| *A61K 38/16* | (2006.01) |
| *A61K 38/00* | (2006.01) |

(52) U.S. Cl.
USPC ............. 424/258.1; 424/184.1; 424/190.1; 424/278.1; 514/21.2; 514/1.1

(58) Field of Classification Search
None
See application file for complete search history.

(56) References Cited

U.S. PATENT DOCUMENTS

| | | |
|---|---|---|
| 2003/0198640 A1 | 10/2003 | Yu et al. |
| 2006/0253100 A1 | 11/2006 | Burright et al. |
| 2007/0087013 A1* | 4/2007 | Sizemore et al. ......... 424/200.1 |

FOREIGN PATENT DOCUMENTS

| | | | |
|---|---|---|---|
| WO | WO 98/56817 | * | 12/1998 |
| WO | 2000014260 A1 | | 3/2000 |
| WO | 2005116201 A1 | | 12/2005 |
| WO | 2001046183 A1 | | 5/2012 |

OTHER PUBLICATIONS

Hardt et al., Proc. Natl. Acad. Sci., 1997; 94: 9887-9892.*
Wu et al., Cell Microbiol., 2012; 14(1): 28-39.*
Bowie et al. (Science, 1990, 257:1306-1310).*
Liao et al., Gastroenterology, Apr. 2008; 134(4), Suppl. 1, pp. A352 (meeting abstract).*
Hardt et al. "A Secreted Salmonella Protein with Homology to an Avirulence Determinant of Plant Pathogenic Bacteria", Proc. Natl. Acad. Sci. U.S.A. 94:9887-9892 (1997).
Liao et al., "Salmonella Type III Effector AvrA Stabilizes Cell Tight Junctions to Inhibit Inflammation in Intestinal Epithelial Cells," PLoS ONE 3(6): e2369 (2008).
Jones et al., "Salmonella AvrA Coordinates Suppression of Host Immune and Apoptotic Defenses via JNK Pathway Blockade," Cell Host & Microbe 3:233-244 (2008).
Collier-Hyams et al., "Cutting Edge: Salmonella AvrA Effector Inhibits the Key Proinflammatory, Anti-Apoptotic NF-kappaB Pathway," J. Immunol. 169:2846-2850 (2000).
Amavisit et al., "Variation between Pathogenic Serovars within Salmonella Pathogenicity Islands," J. Bacteriol. 185 (12):3624-3635 (2003).
Ye et al., "Salmonella Effector AvrA Regulation of Colonic Epithelial Cell Inflammation by Deubiquitination," Am. J. Pathol. 171(3):882-892 (2007).
PCT International Search Report and Written Opinion for PCT/US2009/046142, dated Jun. 3, 2009.
Liao et al., Gastroenterology 134(4):Suppl. 1, Abstract A352 (2008).
Sun et al., Gastroenterology 126(4):Suppl. 2, Abstract A561 (2004).

* cited by examiner

*Primary Examiner* — Vanessa L Ford
*Assistant Examiner* — Lakia Tongue
(74) *Attorney, Agent, or Firm* — LeClairRyan, a Professional Corporation

(57) ABSTRACT

Methods and products are disclosed for treating an inflammatory intestinal disease in a mammalian subject in need thereof, or preventing or reducing a symptom of inflammatory intestinal disease. These method include administering to the subject a therapeutically effective dose of (i) an isolated AvrA protein or polypeptide fragment thereof or (ii) a nucleic acid molecule encoding the isolated AvrA protein or polypeptide fragment. Preferred inflammatory intestinal diseases include Inflammatory Bowel Disease, Celiac Disease, and gastroenteritis.

8 Claims, 20 Drawing Sheets

CLUSTAL 2.0.10 multiple sequence alignment

```
S.enterica_Typhimurium              MIFSVQELSCGGKSMLSPTTRNMGASLSPQPDVSGELNTEALTCIVERLE    50
S.enterica_Typhimurium_LT2          MIFSVQELSCGGKSMLSPTTRNMGASLSPQPDVSGELNTEALTCIVERLE    50
S.enterica_Gallinarum_287/91        MIFSVQELSCGGKSMLSPTTRNMGASLSPQPDVSGELNTEALTCIVERLE    50
S.enterica_Heidelberg_SL486         ----------------------MGASLSPQPDVSGELNTEALTCIVERLE    28
S.enterica_Enteritidis_P125109      MIFSVQELSCGGKSMLSPTTRNMGASLSPQPDVSGELNTEALTCIVERLE    50
S.enterica_Kentucky_CVM29188        ----------------------MGASLSPQPDVSGELNTEALTCIVERLE    28
S.enterica_Saintpaul_SARA29         --------------MLSPTTRNMGASLSPQPDVSGELNTEALTCIVERLE    36
S.enterica_Agona_SL483              --------------MLSPTTRNMGASLSPQPDVSGELNTEALTCIVERLE    36
S.enterica_Schwarzengrund_CVM1      --------------MLSPTTRNMGASLSPQSDVSGELNTEALTCIVERLE    36
                                                   **********:*********************

S.enterica_Typhimurium              SEIIDGSWIHISYEETDLEMPFLVAQANKKYPELNLKFVMSVHELVSSI    100
S.enterica_Typhimurium_LT2          SEIIDGSWIHISYEETDLEMPFLVAQANKKYPELNLKFVMSVHELVSSI    100
S.enterica_Gallinarum_287/91        SEIIDGSWIHISYEETDLEMPFLVAQANKKYPELNLKFVMSVHELVSSI    100
S.enterica_Heidelberg_SL486         SEIIDGSWIHISYEETDLEMPFLVAQANKKYPELNLKFVMSVHELVSSI     78
S.enterica_Enteritidis_P125109      SEIIDGSWIHISYEETDLEMPFLVAQANKKYPELNLKFVMSVHELVSSI    100
S.enterica_Kentucky_CVM29188        SEIIDGSWIHISYEETDLEMPFLVAQANKKYPELNLKFVMSVHELVSSI     78
S.enterica_Saintpaul_SARA29         SEIIDGSWIHISYEETDLEMPFLVAQANKKYPELNLKFVMSVHELVSSI     86
S.enterica_Agona_SL483              SEIIDGSWIHISYEETDLEMPFLVAQANKKYPELNLKFVMSVHELVSSI     86
S.enterica_Schwarzengrund_CVM1      SEIIDGSWIHISYEETDLEMPFLVAQANKKYPELNLKFVMSVHELVSSI     86
                                    ************************************************

S.enterica_Typhimurium              KETRMEGVESARFLVNMGSSGIHISVVDFRVMDGKTSVILFEPAACSAFG    150
S.enterica_Typhimurium_LT2          KETRMEGVESARFLVNMGSSGIHISVVDFRVMDGKTSVILFEPAACSAFG    150
S.enterica_Gallinarum_287/91        KETRMEGVESARFLVNMGSSGIHISVVDFRVMDGKTSVILFEPAACSAFG    150
S.enterica_Heidelberg_SL486         KETRMEGVESARFLVNMGSSGIHISVVDFRVMDGKTSVILFEPAACSAFG    128
S.enterica_Enteritidis_P125109      KETRMEGVESARFLVNMGSSGIHISVVDFRVMDGKTSVILFEPAACSAFG    150
S.enterica_Kentucky_CVM29188        KETRMEGVESARFLVNMGSSGIHISVVDFRVMDGKTSVILFEPAACSAFG    128
S.enterica_Saintpaul_SARA29         KETRMEGVESARFLVNMGSSGIHISVVDFRVMDGKTSVILFEPAACSAFG    136
S.enterica_Agona_SL483              KETRMEGVESARFLVNMGSSGIHISVVDFRVMDGKTSVILFEPAACSAFG    136
S.enterica_Schwarzengrund_CVM1      KETRMEGVESARFIVNMGSSGIHVSVVDFRVMDGKTSVILFEPAACSAFG    136
                                    *************:*********:*************************

S.enterica_Typhimurium              PA-LALRTKAALEREQLPDCYFAMVELDIQRSSSECGIFSLALAKKLQLE    199
S.enterica_Typhimurium_LT2          PALLALRTKAALEREQLPDCYFAMVELDIQRSSSECGIFSLALAKKLQLE    200
S.enterica_Gallinarum_287/91        PALLALRTKAALEREQLPDCYFAMVELDIQRSSSECGIFSLALAKKLQLE    200
S.enterica_Heidelberg_SL486         PALLALRTKAALEREQLPDCYFAMVELDIQRSSSECGIFSLALAKKLQLE    178
S.enterica_Enteritidis_P125109      PALLALRTKAALEREQLPDCYFAMVELDIQRSSSECGIFSLALAKKLQLE    200
S.enterica_Kentucky_CVM29188        PALLALRTKAALEREQLPDCYFAMVELDIQRSSSECGIFSLALAKKLQLE    178
S.enterica_Saintpaul_SARA29         PALLALRTKAALEREQLPDCYFAMVELDIQRSSSECGIFSLALAKKLQLE    186
S.enterica_Agona_SL483              PALLALRTKAALEREQLPDCYFAMVELDIQRSSSECGIFSLALAKKLQLE    186
S.enterica_Schwarzengrund_CVM1      PALLALRTKAALEREQLPDCYFAMVELDIQRSSSECGIFSLALAKKLHLE    186
                                    ** **********************************************:**
```

Figure 1A

CLUSTAL 2.0.10 multiple sequence alignment cont.

```
S.enterica_Typhimurium          FMNLVKIHEDNICERLCGEEPFLPSDKADRYLPVSFYKHTQGAQRLNEYV 249
S.enterica_Typhimurium_LT2      FMNLVKIHEDNICERLCGEEPFLPSDKADRYLPVSFYKHTQGAQRLNEYV 250
S.enterica_Gallinarum_287/91    FMNLVKIHEDNICERLCGEEPFLPSDKADRYLPVSFYKHTQGVQRLNEYV 250
S.enterica_Heidelberg_SL486     FMNLVKIHEDNICERLCGEEPFLPSDKADRYLPVSFYKHTQGVQRLNEYV 228
S.enterica_Enteritidis_P125109  FMNLVKIHEDNICERLCGEEPFLPSDKADRYLPVSFYKHTQGVQRLNEYV 250
S.enterica_Kentucky_CVM29188    FMNLVKIHEDNICERLCGEEPFLPSDKADRYLPVSFYKHTQGVQRLNEYV 228
S.enterica_Saintpaul_SARA29     FMNLVKIHEDNICERLCGEEPFLPSDKADRYLPVSFYKHTQGVQRLNEYV 236
S.enterica_Agona_SL483          FMNLVKIHEDNICERLCGEEPFLPSDKADRYLPVSFYKHTQGVQRLNEYV 236
S.enterica_Schwarzengrund_CVM1  FMNLVKIHEDNICERLCGEEPFLPSDKADRYLPVSFYKHTQGVQRLNEYV 236
                                *************************************** ********

S.enterica_Typhimurium          EANPAAGSSIVNKKNETLYERFDNNAVMLNDKKLSISAHKKRIAEYKSLL 299
S.enterica_Typhimurium_LT2      EANPAAGSSIVNKKNETLYERFDNNAVMLNDKKLSISAHKKRIAEYKSLL 300
S.enterica_Gallinarum_287/91    EANPAAGSSIVNKKNETLYERFDNNAVMLNDKKLSISAHKKRIAEYKSLL 300
S.enterica_Heidelberg_SL486     EANPAAGSSIVNKKNETLYERFDNNAVMLNDKKLSISAHKKRIAEYKSLL 278
S.enterica_Enteritidis_P125109  EANPAAGSSIVNKKNETLYERFDNNAVMLNDKKLSISAHKKRIAEYKSLL 300
S.enterica_Kentucky_CVM29188    EANPAAGSSIVNKKNETLYERFDNNAVMLNDKKLSISAHKKRIAEYKSLL 278
S.enterica_Saintpaul_SARA29     EANPAAGSSIVNKKNETLYERFDNNAVMLNDKKLSIFAHKKRIAEYKSLL 286
S.enterica_Agona_SL483          QANPAAGSSIVNKKNETLYERFDNNAVMLNDKKLSISAHKKRIAEYKSLL 286
S.enterica_Schwarzengrund_CVM1  QANPAAGSSIVNKKNETLYERFDNNAVMLNDKKLSISAHKKRIAEYKSLL 286
                                 ********************************** ************

S.enterica_Typhimurium          KP 301
S.enterica_Typhimurium_LT2      KP 302
S.enterica_Gallinarum_287/91    KS 302
S.enterica_Heidelberg_SL486     KS 280
S.enterica_Enteritidis_P125109  KS 302
S.enterica_Kentucky_CVM29188    KP 280
S.enterica_Saintpaul_SARA29     KP 288
S.enterica_Agona_SL483          KP 288
S.enterica_Schwarzengrund_CVM1  KP 288
                                *.
```

Figure 1B

DIALIGN Alignment

```
S.enterica_Typhimurium          1    ATGATATTTT CGGTGCAGGA GCTATCATGT GGAGGGAAAA GTATGCTAAG
S.enterica_Typhimurium_LT2      1    ATGATATTTT CGGTGCAGGA GCTATCATGT GGAGGGAAAA GTATGCTAAG
S.enterica_Gallinarum_287/91    1    ATGATATTTT CGGTGCAGGA GCTATCATGT GGAGGGAAAA GTATGCTAAG
S.enterica_Enteritidis_P125109  1    ATGATATTTT CGGTGCAGGA GCTATCATGT GGAGGGAAAA GTATGCTAAG
S.enterica_Agona_SL483          1    ---------- ---------- ---------- ---------- --ATGCTAAG
S.enterica_Saintpaul_SARA29     1    ---------- ---------- ---------- ---------- --ATGCTAAG
S.enterica_Schwarzengrund_CVM1  1    ---------- ---------- ---------- ---------- --ATGCTAAG
S.enterica_Kentucky_CVM29188    1    ---------- ---------- ---------- ---------- ----------
S.enterica_Heidelberg_SL486     1    ---------- ---------- ---------- ---------- ----------
                                     ++++++++++ ++++++++++ ++++++++++ ++++++++++ ++++++++++

S.enterica_Typhimurium          51   TCCTACGACT CGTAATATGG GGGCGAGTTT ATCGCCTCAG CCTGACGTCA
S.enterica_Typhimurium_LT2      51   TCCTACGACT CGTAATATGG GGGCGAGTTT ATCGCCTCAG CCTGACGTCA
S.enterica_Gallinarum_287/91    51   TCCTACGACT CGTAATATGG GGGCGAGTTT ATCGCCTCAG CCTGACGTCA
S.enterica_Enteritidis_P125109  51   TCCTACGACT CGTAATATGG GGGCGAGTTT ATCGCCTCAG CCTGACGTCA
S.enterica_Agona_SL483          9    TCCTACGACT CGTAATATGG GGGCGAGTTT ATCGCCTCAG CCTGACGTCA
S.enterica_Saintpaul_SARA29     9    TCCTACGACT CGTAATATGG GGGCGAGTTT ATCGCCTCAG TCTGACGTCA
S.enterica_Schwarzengrund_CVM1  9    TCCTACGACT CGTAATATGG GGGCGAGTTT ATCGCCTCAG CCTGACGTCA
S.enterica_Kentucky_CVM29188    1    ---------- ------ATGG GGGCGAGTTT ATCGCCTCAG CCTGACGTCA
S.enterica_Heidelberg_SL486     1    ---------- ------ATGG GGGCGAGTTT ATCGCCTCAG CCTGACGTCA
                                     ++++++++++ ++++++**** ********** ********** **********

S.enterica_Typhimurium          101  GCGGGGAGCT AAACACCCAA GCATTGACCT CTGGATTCAT GTATTGTTGA GGGTCTGGAA
S.enterica_Typhimurium_LT2      101  GCGGGGAGCT AAACACCCAA GCATTGACCT CTGGATTCAT GTATTGTTGA GGGTCTGGAA
S.enterica_Gallinarum_287/91    101  GCGGGGAGCT AAACACCCAA GCATTGACCT CTGGATTCAT GTATTGTTGA GGGTCTGGAA
S.enterica_Enteritidis_P125109  101  GCGGGGAGCT AAACACCCAA GCATTGACCT CTGGATTCAT GTATTGTTGA GGGTCTGGAA
S.enterica_Agona_SL483          59   GCGGGGAGCT AAACACCCAA GCATTGACCT CTGGATTCAT GTATTGTTGA GGGTCTGGAA
S.enterica_Saintpaul_SARA29     59   GCGGGGAGCT AAACACCCAA GCATTGACCT CTGGATTCAT GTATTGTTGA GGGTCTGGAA
S.enterica_Schwarzengrund_CVM1  59   GCGGGGAGCT AAACACCCAA GCATTGACCT CTGGATTCAT GTATTGTTGA GGGTCTGGAA
S.enterica_Kentucky_CVM29188    35   GCGGGGAGCT AAACACCCAA GCATTGACCT CTGGATTCAT GTATTGTTGA GGGTCTGGAA
S.enterica_Heidelberg_SL486     35   GCGGGGAGCT AAACACCCAA GCATTGACCT CTGGATTCAT GTATTGTTGA GGGTCTGGAA
                                     ********** ********** ********** ********** ********** **********

S.enterica_Typhimurium          151  AGTGAAATTA TAGATGGCAG ATCAGTTACG AGGAAACCGA
S.enterica_Typhimurium_LT2      151  AGTGAAATTA TAGATGGCAG ATCAGTTACG AGGAAACCGA
S.enterica_Gallinarum_287/91    151  AGTGAAATTA TAGATGGCAG ATCAGTTACG AGGAAACCGA
S.enterica_Enteritidis_P125109  151  AGTGAAATTA TAGATGGCAG ATCAGTTACG AGGAAACCGA
S.enterica_Agona_SL483          109  AGTGAAATTA TAGATGGCAG ATCAGTTACG AGGAAACCGA
S.enterica_Saintpaul_SARA29     109  AGTGAAATTA TAGATGGCAG ATCAGTTACG AGGAAACCGA
S.enterica_Schwarzengrund_CVM1  109  AGTGAAATTA TAGATGGCAG ATCAGTTACG AGGAAACCGA
S.enterica_Kentucky_CVM29188    85   AGTGAAATTA TAGATGGCAG ATCAGTTACG AGGAAACCGA
S.enterica_Heidelberg_SL486     85   AGTGAAATTA TAGATGGCAG ATCAGTTACG AGGAAACCGA
                                     ********** ********** ********** **********
```

```
DIALIGN Alignment cont.

S.enterica_Typhimurium          201 TCTCGAAATG ATGCCTTTTC TTGTTGCACA GGCCAATAAG AAGTATCCAG
S.enterica_Typhimurium_LT2      201 TCTCGAAATG ATGCCTTTTC TTGTTGCACA GGCCAATAAG AAGTATCCAG
S.enterica_Gallinarum_287/91    201 TCTCGAAATG ATGCCTTTTC TTGTTGCACA GGCCAATAAG AAGTATCCAG
S.enterica_Enteritidis_P125109  201 TCTCGAAATG ATGCCTTTTC TTGTTGCACA GGCCAATAAG AAGTATCCAG
S.enterica_Agona_SL483          159 TCTCGAAATG ATGCCTTTTC TTGTTGCACA GGCCAATAAG AAGTATCCAG
S.enterica_Saintpaul_SARA29     159 TCTCGAAATG ATGCCTTTTC TTGTTGCACA GGCCAATAAG AAGTATCCAG
S.enterica_Schwarzengrund_CVM1  159 TCTCGAAATG ATGCCTTTTC TTGTTGCACA GGCCAATAAG AAGTATCCAG
S.enterica_Kentucky_CVM29188    135 TCTCGAAATG ATGCCTTTTC TTGTTGCACA GGCCAATAAG AAGTATCCAG
S.enterica_Heidelberg_SL486     135 TCTCGAAATG ATGCCTTTTC TTGTTGCACA GGCCAATAAG AAGTATCCAG
                                    ********** ********** ********** ********** **********

S.enterica_Typhimurium          251 AGTTAAATCT TAAATTTGTT ATGTCAGTCC ATGAGCTTGT TTCCTCTATA
S.enterica_Typhimurium_LT2      251 AGTTAAATCT TAAATTTGTT ATGTCAGTCC ATGAGCTTGT TTCCTCTATA
S.enterica_Gallinarum_287/91    251 AGTTAAATCT TAAATTTGTT ATGTCAGTCC ATGAGCTTGT TTCCTCTATA
S.enterica_Enteritidis_P125109  251 AGTTAAATCT TAAATTTGTT ATGTCAGTCC ATGAGCTTGT TTCCTCTATA
S.enterica_Agona_SL483          209 AGTTAAATCT TAAATTTGTT ATGTCAGTCC ATGAGCTTGT TTCCTCTATA
S.enterica_Saintpaul_SARA29     209 AGTTAAATCT TAAATTTGTT ATGTCAGTCC ATGAGCTTGT TTCCTCTATA
S.enterica_Schwarzengrund_CVM1  209 AGTTAAATCT TAAATTTGTT ATGTCAGTCC ATGAGCTTGT TTCCTCTATA
S.enterica_Kentucky_CVM29188    185 AGTTAAATCT TAAATTTGTT ATGTCAGTCC ATGAGCTTGT TTCCTCTATA
S.enterica_Heidelberg_SL486     185 AGTTAAATCT TAAATTTGTT ATGTCAGTCC ATGAGCTTGT TTCCTCTATA
                                    ********** ********** ********** ********** **********

S.enterica_Typhimurium          301 AAGGAGACCA GAATGGAAGG CGTTGAATCT TTTCAGTCGT GCCCGATTTC TCGTAAATAT
S.enterica_Typhimurium_LT2      301 AAGGAGACCA GAATGGAAGG CGTTGAATCT TTTCAGTCGT GCCCGATTTC TCGTAAATAT
S.enterica_Gallinarum_287/91    301 AAGGAGACCA GAATGGAAGG CGTTGAATCT TTTCAGTCGT GCCCGATTTC TCGTAAATAT
S.enterica_Enteritidis_P125109  301 AAGGAGACCA GAATGGAAGG CGTTGAATCT TTTCAGTCGT GCCCGATTTC TCGTAAATAT
S.enterica_Agona_SL483          259 AAGGAGACCA GAATGGAAGG CGTTGAATCT TTTCAGTCGT GCCCGATTTC TCGTAAATAT
S.enterica_Saintpaul_SARA29     259 AAGGAGACCA GAATGGAAGG CGTTGAATCT TTTCAGTCGT GCCCGATTTA TCGTAAATAT
S.enterica_Schwarzengrund_CVM1  259 AAGGAGACCA GAATGGAAGG CGTTGAATCT TTTCAGTCGT GCCCGATTTC TCGTAAATAT
S.enterica_Kentucky_CVM29188    235 AAGGAGACCA GAATGGAAGG CGTTGAATCT TTTCAGTCGT GCCCGATTTC TCGTAAATAT
S.enterica_Heidelberg_SL486     235 AAGGAGACCA GAATGGAAGG CGTTGAATCT TTTCAGTCGT GCCCGATTTC TCGTAAATAT
                                    ********** ********** ********** ********** ********** **********

S.enterica_Typhimurium          351 GGGAAGTTCA GGTATCCATA TTTCAGTCGT CGATTTTAGA GTTATGGACG
S.enterica_Typhimurium_LT2      351 GGGAAGTTCA GGTATCCATA TTTCAGTCGT CGATTTTAGA GTTATGGACG
S.enterica_Gallinarum_287/91    351 GGGAAGTTCA GGTATCCATA TTTCAGTCGT CGATTTTAGA GTTATGGACG
S.enterica_Enteritidis_P125109  351 GGGAAGTTCA GGTATCCATA TTTCAGTCGT CGATTTTAGA GTTATGGACG
S.enterica_Agona_SL483          309 GGGAAGTTCA GGTATCCATA TTTCAGTCGT CGATTTTAGA GTTATGGACG
S.enterica_Saintpaul_SARA29     309 GGGAAGTTCA GGTATCCATG TTTCAGTCGT CGATTTTAGA GTTATGGACG
S.enterica_Schwarzengrund_CVM1  309 GGGAAGTTCA GGTATCCATA TTTCAGTCGT CGATTTTAGA GTTATGGACG
S.enterica_Kentucky_CVM29188    285 GGGAAGTTCA GGTATCCATA TTTCAGTCGT CGATTTTAGA GTTATGGACG
S.enterica_Heidelberg_SL486     285 GGGAAGTTCA GGTATCCATA TTTCAGTCGT CGATTTTAGA GTTATGGACG
                                    ********** ********** ********** ********** **********
```

```
DIALIGN Alignment cont.

S.enterica_Typhimurium            401  GAAAGACATC GGTGATTTTG TTCGAACCAG CAGCGTGTAG CGCTTTTGGA
S.enterica_Typhimurium_LT2        401  GAAAGACATC GGTGATTTTG TTCGAACCAG CAGCGTGTAG CGCTTTTGGA
S.enterica_Gallinarum_287/91      401  GAAAGACATC GGTGATTTTG TTCGAACCAG CAGCGTGTAG CGCTTTTGGA
S.enterica_Enteritidis_P125109    401  GAAAGACATC GGTGATTTTG TTCGAACCAG CAGCGTGTAG CGCTTTTGGA
S.enterica_Agona_SL483            359  GAAAGACATC GGTGATTTTG TTCGAACCAG CAGCGTGTAG CGCTTTTGGA
S.enterica_Saintpaul_SARA29       359  GAAAGACATC GGTGATTTTG TTCGAACCAG CAGCGTGTAG CGCTTTTGGA
S.enterica_Schwarzengrund_CVM1    359  GAAAGACATC GGTGATTTTG TTCGAACCAG CAGCGTGTAG CGCTTTTGGA
S.enterica_Kentucky_CVM29188      335  GAAAGACATC GGTGATTTTG TTCGAACCAG CAGCGTGTAG CGCTTTTGGA
S.enterica_Heidelberg_SL486       335  GAAAGACATC GGTGATTTTG TTCGAACCAG CAGCGTGTAG CGCTTTTGGA
                                       ********** ********** ********** ********** **********

S.enterica_Typhimurium            451  CCTGC---AC TGGCGTTGAG GACCAAAGCA GCTCTTGAAC GTGAACAACT
S.enterica_Typhimurium_LT2        451  CCTGCTTTAC TGGCGTTGAG GACCAAAGCA GCTCTTGAAC GTGAACAACT
S.enterica_Gallinarum_287/91      451  CCTGCTTTAC TGGCGTTGAG GACCAAAGCA GCTCTTGAAC GTGAACAACT
S.enterica_Enteritidis_P125109    451  CCTGCTTTAC TGGCGTTGAG GACCAAAGCA GCTCTTGAAC GTGAACAACT
S.enterica_Agona_SL483            409  CCTGCTTTAC TGGCGTTGAG GACCAAAGCA GCTCTTGAAC GTGAACAACT
S.enterica_Saintpaul_SARA29       409  CCTGCTTTAC TGGCGTTGAG GACCAAAGCA GCTCTTGAAC GTGAACAACT
S.enterica_Schwarzengrund_CVM1    409  CCTGCTTTAC TGGCATTGAG GACCAAAGCA GCTCTTGAAC GTGAACAACT
S.enterica_Kentucky_CVM29188      385  CCTGCTTTAC TGGCGTTGAG GACCAAAGCA GCTCTTGAAC GTGAACAACT
S.enterica_Heidelberg_SL486       385  CCTGCTTTAC TGGCGTTGAG GACCAAAGCA GCTCTTGAAC GTGAACAACT
                                       *****  ** ********** ********** ********** **********

S.enterica_Typhimurium            498  GCCTGATTGT TATTTTGCTA TGGTCGAGCT GGACATTCAA CGAAGCTCTT
S.enterica_Typhimurium_LT2        501  GCCTGATTGT TATTTTGCTA TGGTCGAGCT GGACATTCAA CGAAGCTCTT
S.enterica_Gallinarum_287/91      501  GCCTGATTGT TATTTTGCTA TGGTCGAGCT GGACATTCAA CGAAGCTCTT
S.enterica_Enteritidis_P125109    501  GCCTGATTGT TATTTTGCTA TGGTCGAGCT GGACATTCAA CGAAGCTCTT
S.enterica_Agona_SL483            459  GCCTGATTGT TATTTTGCTA TGGTCGAGCT GGACATTCAA CGAAGCTCTT
S.enterica_Saintpaul_SARA29       459  GCCTGATTGT TATTTTGCTA TGGTCGAGCT GGACATTCAA CGAAGCTCTT
S.enterica_Schwarzengrund_CVM1    459  GCCTGATTGT TATTTTGCTA TGGTCGAGCT GGACATTCAA CGAAGCTCTT
S.enterica_Kentucky_CVM29188      435  GCCTGATTGT TATTTTGCTA TGGTCGAGCT GGACATTCAA CGAAGCTCTT
S.enterica_Heidelberg_SL486       435  GCCTGATTGT TATTTTGCTA TGGTCGAGCT GGACATTCAA CGAAGCTCTT
                                       ********** ********** ********** ********** **********

S.enterica_Typhimurium            548  CTGAATGCGG TATTTTTAGC CTGGCGCTCG CCAAAAAACT TCAGCTTGAA
S.enterica_Typhimurium_LT2        551  CTGAATGCGG TATTTTTAGC CTGGCGCTCG CCAAAAAACT TCAGCTTGAA
S.enterica_Gallinarum_287/91      551  CTGAATGCGG TATTTTTAGC CTGGCGCTCG CCAAAAAACT TCAGCTTGAA
S.enterica_Enteritidis_P125109    551  CTGAATGCGG TATTTTTAGC CTGGCGCTCG CCAAAAAACT TCAGCTTGAA
S.enterica_Agona_SL483            509  CTGAATGTGG TATTTTTAGC CTGGCGCTCG CCAAAAAACT TCAGCTTGAA
S.enterica_Saintpaul_SARA29       509  CTGAATGCGG TATTTTTAGC CTGGCGCTCG CCAAAAAACT TCAGCTTGAA
S.enterica_Schwarzengrund_CVM1    509  CTGAATGCGG TATTTTTAGC CTGGCGCTCG CCAAAAAACT TCAGCTTGAA
S.enterica_Kentucky_CVM29188      485  CTGAATGCGG TATTTTTAGC CTGGCGCTCG CCAAAAAACT TCATCTTGAA
S.enterica_Heidelberg_SL486       485  CTGAATGCGG TATTTTTAGC CTGGCGCTCG CCAAAAAACT TCAGCTTGAA
                                       *******  * ********** ********** ********** *** ******
```

DIALIGN alignment cont.

```
S.enterica_Typhimurium          798  GCTTTATGAG CGATTCGATA ACAATGCCGT TATGCTAAAC GATAAAAAAC
S.enterica_Typhimurium_LT2      801  GCTTTATGAG CGATTCGATA ACAATGCCGT TATGCTAAAC GATAAAAAAC
S.enterica_Gallinarum_287/91    801  GCTTTATGAG CGATTCGATA ACAATGCCGT TATGCTAAAC GATAAAAAAC
S.enterica_Enteritidis_P125109  801  GCTTTATGAG CGATTCGATA ACAATGCCGT TATGCTAAAC GATAAAAAAC
S.enterica_Agona_SL483          759  GCTTTATGAG CGATTCGATA ACAATGCCGT TATGCTAAAC GATAAAAAAC
S.enterica_Saintpaul_SARA29     759  GCTTTATGAG CGATTCGATA ACAATGCCGT TATGCTAAAC GATAAAAAAC
S.enterica_Schwarzengrund_CVM1  759  GCTTTATGAG CGATTCGATA ACAATGCCGT TATGCTAAAC GATAAAAAAC
S.enterica_Kentucky_CVM29188    735  GCTTTATGAG CGATTCGATA ACAATGCCGT TATGCTAAAC GATAAAAAAC
S.enterica_Heidelberg_SL486     735  GCTTTATGAG CGATTCGATA ACAATGCCGT TATGCTAAAC GATAAAAAAC
                                     ********** ********** ********** ********** **********

S.enterica_Typhimurium          848  TCTCTATATC CGCTCATAAA AAAAGGATAG CTGAATATAA GTCTTTACTT
S.enterica_Typhimurium_LT2      851  TCTCTATATC CGCTCATAAA AAAAGGATAG CTGAATATAA GTCTTTACTT
S.enterica_Gallinarum_287/91    851  TCTCTATATC CGCTCATAAA AAAAGGATAG CTGAATATAA GTCTTTACTT
S.enterica_Enteritidis_P125109  851  TCTCTATATC CGCTCATAAA AAAAGGATAG CTGAATATAA GTCTTTACTT
S.enterica_Agona_SL483          809  TCTCTATATC CGCTCATAAA AAAAGGATAG CTGAATATAA GTCTTTACTT
S.enterica_Saintpaul_SARA29     809  TCTCTATATT CGCTCATAAA AAAAGGATAG CTGAATATAA GTCTTTGCTT
S.enterica_Schwarzengrund_CVM1  809  TCTCTATATC CGCTCATAAA AAAAGGATAG CTGAATATAA GTCTTTACTT
S.enterica_Kentucky_CVM29188    785  TCTCTATATC CGCTCATAAA AAAAGGATAG CTGAATATAA GTCTTTACTT
S.enterica_Heidelberg_SL486     785  TCTCTATATC CGCTCATAAA AAAAGGATAG CTGAATATAA GTCTTTACTT
                                     ********** ********** ********** ********** *** ****

S.enterica_Typhimurium          898  AAACCGTAA
S.enterica_Typhimurium_LT2      901  AAACCGTAA
S.enterica_Gallinarum_287/91    901  AAATCGTAA
S.enterica_Enteritidis_P125109  901  AAATCGTAA
S.enterica_Agona_SL483          859  AAACCGTAA
S.enterica_Saintpaul_SARA29     859  AAACCGTAA
S.enterica_Schwarzengrund_CVM1  859  AAACCGTAA
S.enterica_Kentucky_CVM29188    835  AAACCGTAA
S.enterica_Heidelberg_SL486     835  AAATCGTAA
                                     *** *****
```

Figure 2E

Figure 10A
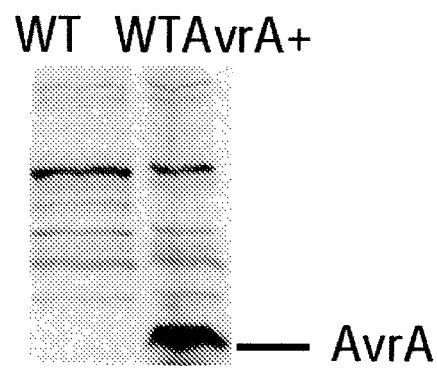
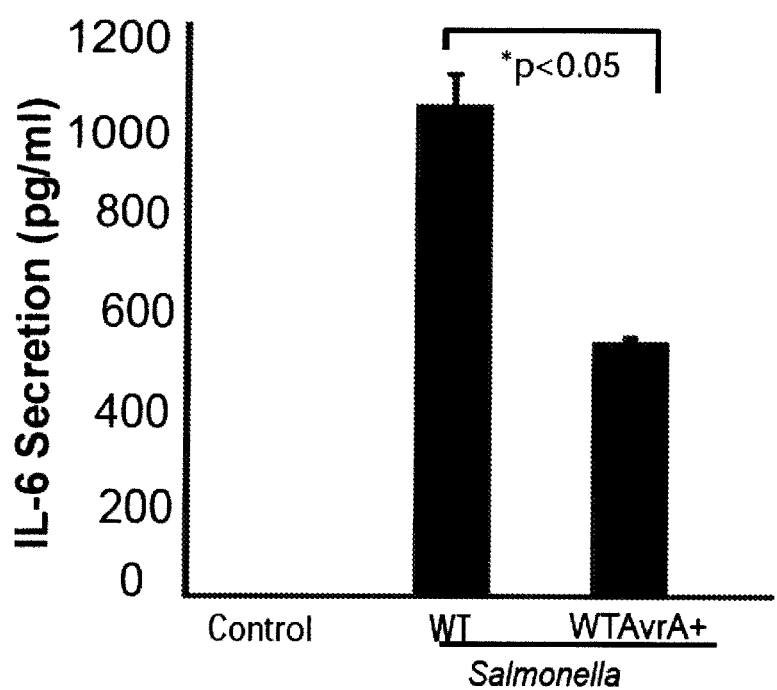
Figure 10B

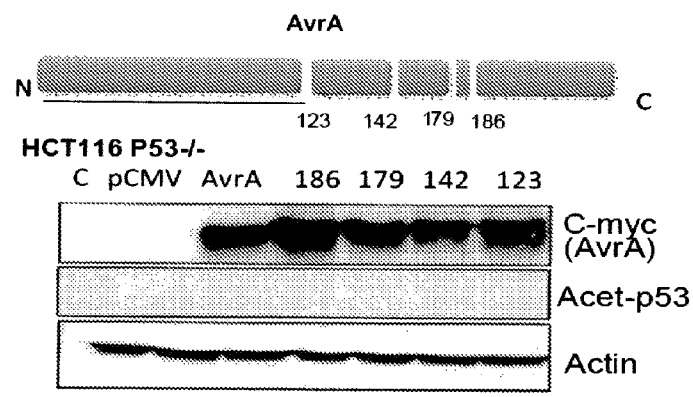
Figure 11A
Figure 11B
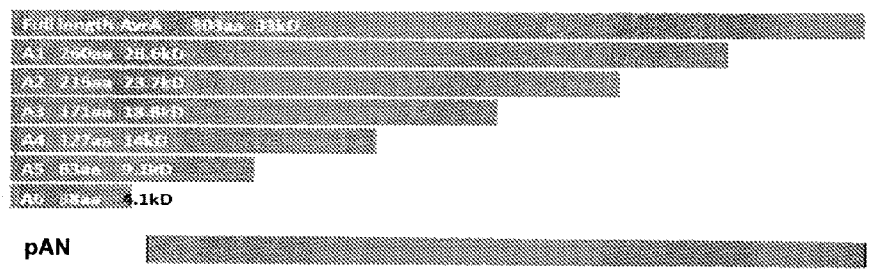
Figure 11C
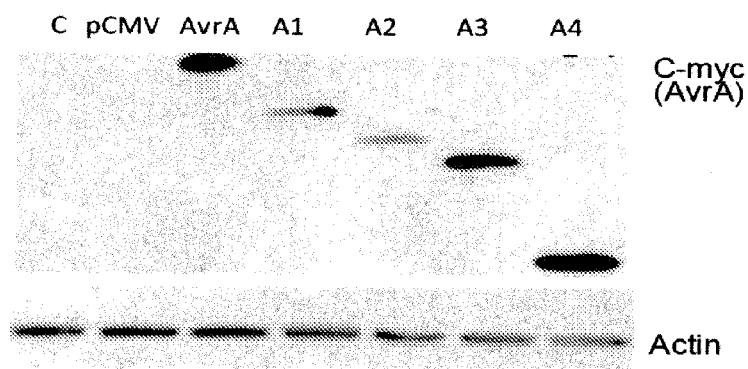
Figure 11D

METHODS OF TREATING INFLAMMATORY INTESTINAL DISEASE AND MANAGING SYMPTOMS THEREOF

This application is a national stage application under 35 U.S.C. 371 of PCT/US2009/046142, filed Jun. 3, 2009, and claims the priority benefit of U.S. Provisional Patent Application Ser. No. 61/058,421, filed Jun. 3, 2008, which is hereby incorporated by reference in its entirety.

This invention was made with government support under grant number KO1 DK075386 awarded by the National Institutes of Health. The government has certain rights in this invention.

FIELD OF THE INVENTION

The present invention generally relates to methods, preparations and pharmaceutical compositions for treating or preventing inflammatory intestinal diseases in mammalian subjects.

BACKGROUND OF THE INVENTION

Intestinal epithelial cells participate in immune regulation and mucosal integrity. Tight junctions (TJs) constitute continuous circumferential seals around cells and serve as a protective barrier, preventing solutes and water from passing freely through the paracellular pathway. Tight junctions can be altered by various pathogens, as well as by their toxins. These effects may result from direct modification of TJ proteins such as occludin, claudin, and Zonula occludens-1 (ZO-1), or by alteration of the perijunctional actomyosin ring (Berkes et al., "Intestinal Epithelial Responses to Enteric Pathogens: Effects on the Tight Junction Barrier, Ion Transport, and Inflammation," *Gut* 52: 439-451 (2003); Landau, "Epithelial Paracellular Proteins in Health and Disease," *Curr Opin Nephrol Hypertens* 15: 425-429 (2006); Sousa et al., "Microbial Strategies to Target, Cross or Disrupt Epithelia," *Curr Opin Cell Biol* 17:489-498 (2005)).

*Salmonella enterica* serovar *Typhimurium* is a major cause of human gastroenteritis. Infection of polarized epithelial cell monolayers by *S. Typhimurium* disrupts TJ structure and function (Finlay et al., "*Salmonella* Interactions with Polarized Human Intestinal Caco-2 Epithelial Cells," *J Infect Dis* 162:1096-1106 (1990); Jepson et al., "Rapid Disruption of Epithelial Barrier Function by *Salmonella Typhimurium* is Associated with Structural Modification of Intercellular Junctions," *Infect Immun* 63:356-359 (1995); Jepson et al., "Localization of Dysfunctional Tight Junctions in *Salmonella enterica* serovar *Typhimurium*-infected Epithelial Layers," *Infect Immun* 68:7202-7208 (2000); Tafazoli et al., "Disruption of Epithelial Barrier Integrity by *Salmonella enterica* serovar *Typhimurium* Requires Geranylgeranylated Proteins," *Infect Immun* 71:872-881 (2003)). TJ disruption is dependent on the type III secretory system (TTSS) of *Salmonella*. TTSS is a needle-like protein transport device used by Gram-negative pathogenic bacteria. It allows bacteria to inject virulence effectors into eukaryotic host cells (Galan, "*Salmonella* Interactions with Host Cells: Type III Secretion at Work," *Annu Rev Cell Dev Biol* 17:53-86 (2001)). TTSS is encoded by the *Salmonella* pathogenicity island 1 (SPI-1) (Galan, "Interaction of *Salmonella* with Host Cells through the Centisome 63 Type III Secretion System," *Curr Opin Microbiol* 2:46-50 (1999)). A recent study indicated that SopB, SopE, SopE2, and SpiA are the TTSS secreted SPI-1 effectors responsible for the disruption of TJ structure and function (Boyle et al., "*Salmonella enterica* serovar *Typhimurium* Effectors SopB, SopE, SopE2 and SipA Disrupt Tight Junction Structure and Function," *Cell Microbiol* 8:1946-1957 (2006)). The specific bacterial effectors responsible for the regulation of TJs, however, remain to be identified. The majority of published studies regarding *Salmonella* and TJ have utilized in vitro cultured epithelial models. The physiological consequences of *Salmonella*-effector-induced alteration of TJ function need to be addressed in vivo using animal models.

AvrA is a newly described bacterial effector transported into the host cell by the TTSS of *Salmonella* (Hardt et al., "A Secreted *Salmonella* Protein with Homology to an Avirulence Determinant of Plant Pathogenic Bacteria," *Proc Natl Acad Sci USA* 94:9887-9892 (1997)). It also belongs to the SPI-1 (Hardt et al., "A Secreted *Salmonella* Protein with Homology to an Avirulence Determinant of Plant Pathogenic Bacteria," *Proc Natl Acad Sci USA* 94:9887-9892 (1997)). The SPI-1 effectors are responsible for early inflammation in the mouse model of *S. Typhimurium*-induced enterocolitis (Hapfelmeier et al., "Role of the *Salmonella* Pathogenicity Island 1 Effector Proteins SipA, SopB, SopE, and SopE2 in *Salmonella enterica* subspecies 1 serovar *Typhimurium* Colitis in Streptomycin-pretreated Mice," *Infect Immun* 72:795-809 (2004); Barthel et al., "Pretreatment of Mice with Streptomycin Provides a *Salmonella enterica* serovar *Typhimurium* Colitis Model that Allows Analysis of Both Pathogen and Host," *Infect Immun* 71:2839-2858 (2003)). AvrA protein from *Salmonella Typhimurium* inhibits activation of the proinflammatory NF-κB transcription factor in cultured human epithelial cells (Collier-Hyams et al., "Cutting Edge: *Salmonella* AvrA Effector Inhibits the Key Proinflammatory, Anti-apoptotic NF-kappa B Pathway," *J Immunol* 169:2846-2850 (2002)). Based on the sequence alignment, AvrA belongs to the cysteine protease family (Orth et al., "Disruption of Signaling by *Yersinia* effector YopJ, a Ubiquitin-like Protein Protease," *Science* 290:1594-1597 (2000)). Representative AvrA members include the adenovirus-like proteases (human adenovirus type 2, fowl adenovirus 8, Hemorrhagic enteritis virus), YopJ (*Yersinia* outer protein J), and AvrBsT. The catalytic triad for the cysteine protease is present in all AvrA family members (Orth et al., "Disruption of Signaling by *Yersinia* effector YopJ, a Ubiquitin-like Protein Protease," *Science* 290:1594-1597 (2000); Orth et al., "Inhibition of the Mitogen-activated Protein Kinase Kinase Superfamily by a *Yersinia* Effector," *Science* 285:1920-1923 (1999)). Further studies demonstrated that expression of a mutant AvrA protein with a single amino acid residue transition (AvrA/C186A) in a putative catalytic cysteine of this enzyme did not inhibit TNFα-stimulated induction of the reporter (Collier-Hyams et al., "Cutting Edge: *Salmonella* AvrA Effector Inhibits the Key Proinflammatory, Anti-apoptotic NF-kappa B Pathway," *J Immunol* 169:2846-2850 (2002)). It was recently demonstrated that AvrA has deubiquitinase activity which removes ubiquitins from ub-IκBα, thus inhibiting NF-κB activity (Ye et al., "*Salmonella* effector AvrA Regulation of Colonic Epithelial Cell Inflammation by Deubiquitination," *Am J Pathol* 171:882-892 (2007)). AvrA C186A mutant protein had reduced deubiquitinase activity as evidenced by cleaving less ubiquitin moieties from IκBα (Ye et al., "*Salmonella* effector AvrA Regulation of Colonic Epithelial Cell Inflammation by Deubiquitination," *Am J Pathol* 171:882-892 (2007)). This data further supports the hypothesis that AvrA protein has protease activity which attenuates the proinflammatory NF-κB pathway.

The AvrA gene is present in 80% of *Salmonella enterica* serovars (Streckel et al., "Expression Profiles of Effector Proteins SopB, SopD1, SopE1, and AvrA Differ with Systemic, Enteric, and Epidemic Strains of *Salmonella enterica*," *Mol Nutr Food Res* 48:496-503 (2004)). The protein expression of AvrA differs strikingly between bacterial strains in systemic disease and in enteritis, which is localized to the intestine (Streckel et al., "Expression Profiles of Effector Proteins SopB, SopD1, SopE1, and AvrA Differ with Systemic, Enteric, and Epidemic Strains of *Salmonella enterica*," *Mol Nutr Food Res* 48:496-503 (2004)). AvrA protein was not expressed in strains related to systemic disease, but was conditionally (pH below 6.0) expressed in the enteritis-related strains. In addition, *S. enterica* strains from systemic infections could be characterized by their strong SopB and SopE1 expression and by the absence of SopD1 and AvrA proteins (Streckel et al., "Expression Profiles of Effector Proteins SopB, SopD1, SopE1, and AvrA Differ with Systemic, Enteric, and Epidemic Strains of *Salmonella enterica*," *Mol Nutr Food Res* 48:496-503 (2004)). Four phenotypic classes of *S. enterica* have been identified under defined standard culture conditions: strains with a constitutive synthesis of AvrA; strains with an acid induction of AvrA; strains with silent avrA genes; and a fourth class without AvrA gene (Ben-Barak et al., "The Expression of the Virulence-associated Effector Protein Gene avrA is Dependent on a *Salmonella enterica*-specific Regulatory Function," *Int J Med Microbiol* 296:25-38 (2006)). Taken together, AvrA protein expression is very different from the other *Salmonella* effectors such as SopB, SopD, and SopE (Ben-Barak et al., "The Expression of the Virulence-associated Effector Protein Gene avrA is Dependent on a *Salmonella enterica*-specific Regulatory Function," *Int J Med Microbiol* 296:25-38 (2006)). Although it is premature to claim a correlation of AvrA with the clinical and epidemiological potency of Salmonellae, current studies indicate that a fine-tuning of AvrA expression takes place during the pathogenesis of *Salmonella* infection.

Unlike SopB and SopD, AvrA does not increase physiologic fluid secretion into infected calf ileal loops (Zhang et al., "The *Salmonella enterica* serotype *typhimurium* Effector Proteins SipA, SopA, SopB, SopD, and SopE2 Act in Concert to Induce Diarrhea in Calves," *Infect Immun* 70:3843-3855 (2002); Schesser et al., "The *Salmonella* YopJ-homologue AvrA does not Possess YopJ-like Activity," *Microb Pathog* 28:59-70 (2000)). However, the role of AvrA expression on the tight junction structure and function of the intestinal epithelial cells in both in vitro and in vivo models is unexplored.

The present invention overcomes these and other deficiencies in the art, and identifies a therapeutic mechanism for treatment of Inflammatory Bowel Disease ("IBD"), Celiac Disease, and other inflammatory conditions of the intestine.

SUMMARY OF THE INVENTION

A first aspect of the present invention relates to a method for treating an inflammatory intestinal disease in a mammalian subject in need thereof, the method including administering to the subject a therapeutically effective dose of (i) an isolated AvrA protein or polypeptide fragment thereof or (ii) a nucleic acid molecule encoding the isolated AvrA protein or polypeptide fragment. In preferred embodiments, the inflammatory intestinal disease is IBD, Celiac Disease, or gastroenteritis.

A second aspect of the present invention relates to a method for preventing or reducing a symptom of inflammatory intestinal disease in a mammalian subject, the method including: a) identifying a mammalian subject at risk of inflammatory intestinal disease; and b) administering to the subject a therapeutically effective dose of (i) an isolated AvrA protein or polypeptide fragment thereof, or (ii) a nucleic acid molecule encoding the AvrA protein or polypeptide fragment. In preferred embodiments, the inflammatory intestinal disease is IBD, Celiac Disease, or gastroenteritis.

A third aspect of the present invention relates to a pharmaceutical composition that includes, in a unit dose, a therapeutically effective amount of an isolated AvrA protein or polypeptide fragment thereof, and a pharmaceutically acceptable carrier.

A fourth aspect of the present invention relates to an expression vector that includes a promoter operable in mammalian epithelial cells and a nucleic acid molecule operably coupled 3' of the promoter, the nucleic acid molecule encoding an AvrA protein or polypeptide fragment thereof. Compositions that contain the expression vector, including pharmaceutical compositions, are also encompassed.

The results presented in the accompanying Examples demonstrate that *Salmonella* lacking AvrA decreased tight junction ("TJ") protein expression in both cultured colonic epithelial cell and bacterial infected mouse models. While examining changes in resistance and cell permeability, TJ protein expression and protein distribution were examined as induced by AvrA-deficient and AvrA-sufficient bacterial strains in vitro and in vivo. The data presented demonstrate that TJ protein expression increased significantly in cells transiently transfected with the AvrA gene. These findings indicate an important role for the bacterial effector AvrA in regulating the structure and function of tight junctions in intestinal epithelial cells. Specifically, AvrA and active polypeptide fragments thereof, whether administered as a pharmaceutical composition or expressed via gene expression vector, can be used to treat inflammatory intestinal diseases or disorders, such as IBD, Celiac Disease, and gastroenteritis, as well as manage symptoms thereof and heal intestinal tissue damaged by various disorders.

Other features and advantages of the invention will be apparent from the following detailed description and claims.

BRIEF DESCRIPTION OF THE DRAWINGS

FIGS. 1A-B illustrate a ClustalW multiple sequence alignment of nine exemplary AvrA amino acid sequences. SEQ ID NO: 1=*Salmonella enterica* serovar *Typhimurium* (Genbank Accession No. AAB83970, which is hereby incorporated by reference in its entirety); SEQ ID NO: 2=*Salmonella typhimurium* LT2 (Genbank Accession No. AAL21745, which is hereby incorporated by reference in its entirety); SEQ ID NO: 3=*Salmonella enterica* subsp. *enterica* serovar Gallinarum str. 287/91 (Genbank Accession No. CAR38577, which is hereby incorporated by reference in its entirety); SEQ ID NO: 4=*Salmonella enterica* subsp. *enterica* serovar Heidelberg str. SL486 (Genbank Accession No. EDZ24776, which is hereby incorporated by reference in its entirety); SEQ ID NO: 5=*Salmonella enterica* subsp. *enterica* serovar Enteritidis str. P125109 (Genbank Accession No. CAR34285, which is hereby incorporated by reference in its entirety); SEQ ID NO: 6=*Salmonella enterica* subsp. *enterica* serovar Kentucky str. CVM29188 (Genbank Accession No. EDX43702, which is hereby incorporated by reference in its entirety); SEQ ID NO: 7=*Salmonella enterica* subsp. *enterica* serovar Saintpaulia, strain SARA23 (Genbank Accession No. EDZ12687, which is hereby incorporated by reference in its entirety); SEQ ID NO: 8=*Salmonella enterica* subsp. *enterica* serovar Agona strain SL483 (Genbank Accession No. ACH48766, which is hereby incorporated by reference in its entirety); and SEQ ID NO: 9=*Salmonella enterica* subsp. *enterica* serovar Schwarzengrund str. CVM19633 (Genbank Accession No. ACF92027, which is hereby incorporated by reference in its entirety). Symbols: "*" denotes absolutely conserved residues; ":" and "." denote conserved and semi-conserved substitutions, respectively.

Figure 2D:
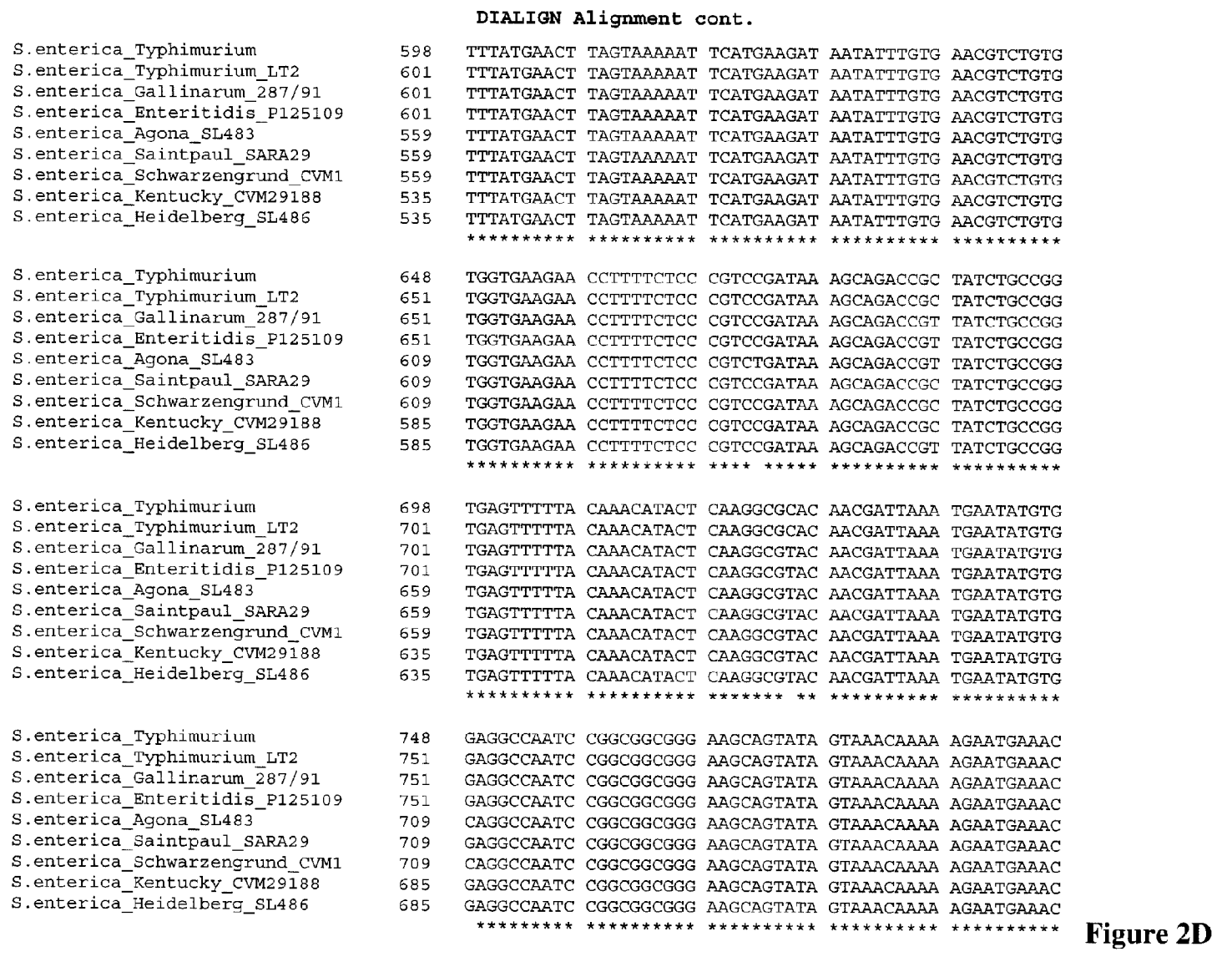

FIGS. 2A-E illustrate a Dialign multiple sequence alignment of nine exemplary avrA open reading frames (DNA sequences). SEQ ID NO: 10=*Salmonella enterica* serovar *Typhimurium* (Genbank Accession No. AF013573, which is hereby incorporated by reference in its entirety); SEQ ID NO: 11=*Salmonella typhimurium* LT2 (Genbank Accession No. AE006468, which is hereby incorporated by reference in its entirety); SEQ ID NO: 12=*Salmonella enterica* subsp. *enterica* serovar Gallinarum str. 287/91 (Genbank Accession No. AM933173, which is hereby incorporated by reference in its entirety); SEQ ID NO: 13=*Salmonella enterica* subsp. *enterica* serovar Heidelberg str. SL486 (Genbank Accession No. ABEL01000005, which is hereby incorporated by reference in its entirety); SEQ ID NO: 14=*Salmonella enterica* subsp. *enterica* serovar Enteritidis str. P125109 (Genbank Accession No. AM933172, which is hereby incorporated by reference in its entirety); SEQ ID NO: 15=*Salmonella enterica* subsp. *enterica* serovar Kentucky str. CVM29188 (Genbank Accession No. ABAK02000001, which is hereby incorporated by reference in its entirety); SEQ ID NO: 16=*Salmonella enterica* subsp. *enterica* serovar Saintpaulia, strain SARA23 (Genbank Accession No. ABAN01000004, which is hereby incorporated by reference in its entirety); SEQ ID NO: 17=*Salmonella enterica* subsp. *enterica* serovar Agona strain SL483 (Genbank Accession No. CP001138, which is hereby incorporated by reference in its entirety); and SEQ ID NO: 18=*Salmonella enterica* subsp. *enterica* serovar Schwarzengrund str. CVM19633 (Genbank Accession No. CP001127, which is hereby incorporated by reference in its entirety). Symbols: "*" denotes absolutely conserved nucleic acids; "+" denotes conserved nucleic acids among subset of sequence aligned.

In FIG. 3A, Western blots of occludin-1, ZO-1, claudin-1, and E-cadherin are shown. Polarized human colonic epithelial T84 cells were colonized with AvrA-deficient or -sufficient bacterial strains for 30 minutes, washed with HBSS and incubated in DMEM for 30 minutes. Cells were lysed. Equal volumes of total cell lysate were processed for immunoblotting with Rabbit anti-claudin-1, Mouse anti-occludin-1, Mouse anti-ZO-1 antibodies, or E-cadherin antibodies. Experimental groups: Control: polarized T84 cells without any treatment; WT: wild-type *S. Typhimurium* ATCC 14028s without sufficient AvrA protein expression; PhoP$^c$: parental PhoP$^c$ with sufficient AvrA protein expression; AvrA$^-$: PhoP$^c$ AvrA mutant; AvrA$^-$/AvrA$^+$: PhoP$^c$ AvrA– transcomplemented with a plasmid encoding WT AvrA; or *E. coli* F18: commensal bacteria isolated from human intestine. In FIG. 3B densitometry of occludin and ZO-1 are shown. Relative occludin-1 and ZO-1 band intensity was determined using NIH Image 1.63 software. Occludin-1 and ZO-1 expression significantly increased in the PhoP$^c$ group compared to the Control, WT, and AvrA– groups in absence of AvrA protein. *P<0.05. Data are reported as mean±SD of 3 independent experiments.

In FIG. 4A, HT29C19A cells were transfected with a pCMV-myc-AvrA wild-type gene construct, a pCMV-myc-AvrAC186A AvrA mutant construct, or control empty pCMV-myc plasmid using LipofectAMINE (Invitrogen). The AvrA mutant C186A is a single amino acid residue transition which is mutated at the key cysteine required for AvrA activity. 24 h after transfection, cells were lysed in protein-loading buffer. Equal volumes of total cell lysis were processed for immunoblotting for ZO-1, occludin-1, claudin-1, AvrA, and β-actin. Control: normal HT29C119A without treatment; pCMV: cells transfected with empty pCMV-myc plasmid; AvrA: cells transfected with pCMV-myc-AvrA plasmid; C186A: cells transfected with AvrA mutant C186A plasmid. FIG. 4B shows the densitometry of ZO-1, occludin-1, and claudin-1. These are significant increases of ZO-1 and occludin-1 expression in AvrA– overexpressed cells compared to the cells without AvrA expression. AvrA mutant C186A expression did not increase ZO-1 and occludin-1 expression. It indicates that cysteine mutation abolished the effects of wild-type AvrA on TJ protein expression. *P<0.05, **P<0.01. Data are reported as mean±SD of 2-3 independent experiments.

White arrow in Panel AvrA− DAPI shows lymphoid aggregation. Of note is the disorganized structure of ZO-1 in the colonic epithelial cells infected with AvrA− bacterial strain. Images shown are from a single experiment and are representative of three separate experiments. n=3 animals in each experimental group.

Figure 9:
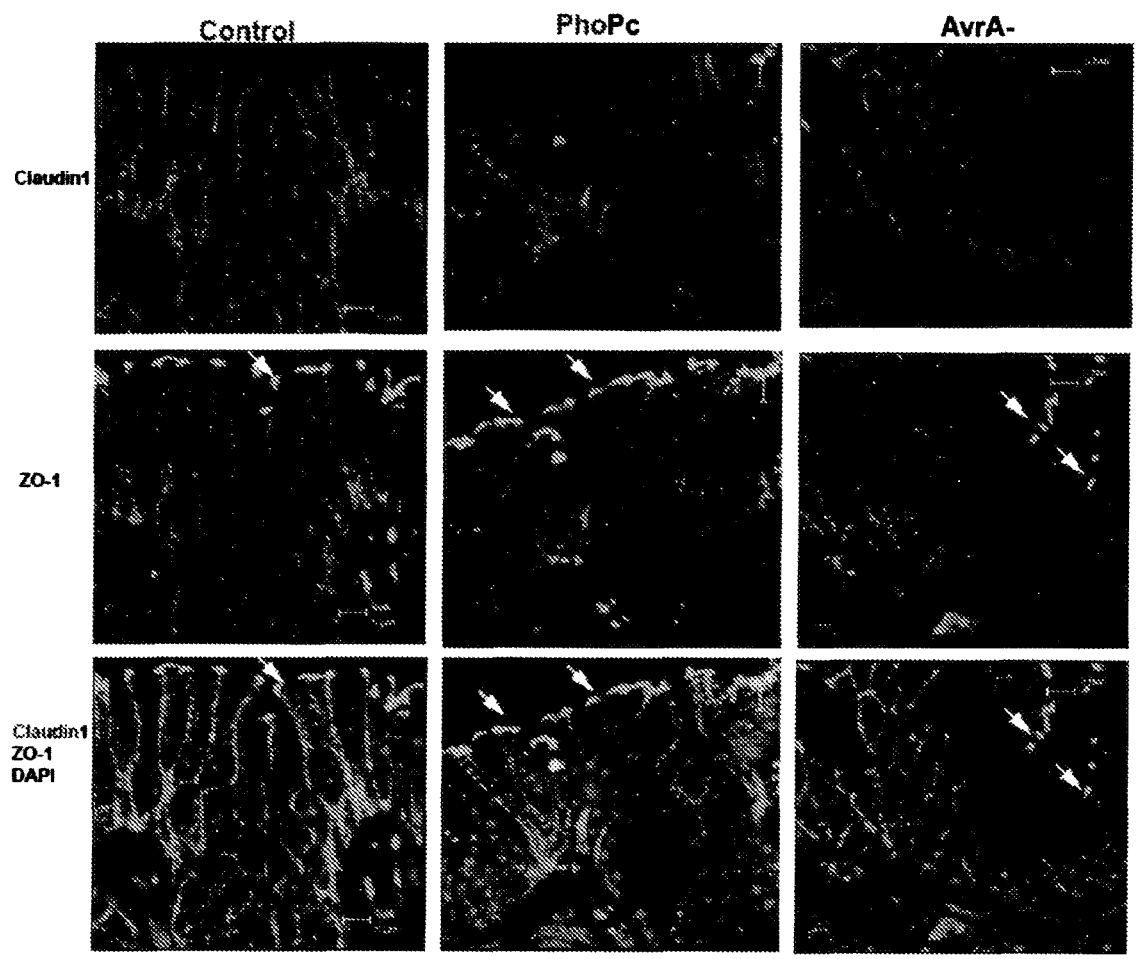

FIG. 9 illustrates in vivo immunostaining of claudin-1 and ZO-1 at higher magnification. Arrows in Panel ZO-1 show staining of ZO-1 protein on the top of the intestinal crypts. Panel AvrA⁻ showing disrupted ZO-1 and weaker claudin-1 staining in epithelial cells. ZO-1 was detected at the tight junction of villous enterocytes in both normal control and PhoP$^c$-treated animals. No intracellular ZO-1 deposits were detected after PhoP$^c$ infection. The ring-like structure of ZO-1 was disrupted in mouse colon infected by the AvrA-deficient bacteria. The staining of claudin-1 is weaker in the AvrA− treated intestinal epithelium. No intracellular claudin-1 deposits were detected after PhoP$^c$ or AvrA− infection. n=3 animals in each experimental group.

FIGS. 10A-B illustrate that the *Salmonella* effector AvrA inhibited IL-6 secretion in mice. FIG. 10A shows the AvrA protein expression level in the AvrA-sufficient or -deficient bacterial strains. Total bacterial lysates were immunoblotted with antibodies against AvrA. FIG. 10B is a graph illustrating IL-6 levels in mouse serum samples 2 hours after WT *Salmonella* or WT *Salmonella* AvrA infection. Data shown in FIG. 10B are mean±SD for n=3 animals in each experimental group. Significance was at p≤0.05.

FIGS. 11A-D illustrate several types of AvrA pinpoint mutants and truncation mutants. FIG. 11A illustrates the scheme of the *Salmonella* AvrA point-mutants C186A, C179A, E142A, and H123A. Expression of these pinpoint mutants in HCT116p53−/− cells is shown in FIG. 11B. FIG. 11C illustrates the scheme for Wild-type (WT) AvrA and truncated AvrA DNAs. All expressed proteins were tagged with Myc at the N-terminus. Expression of these AvrA truncation mutants in epithelial cells, as detected by Western blot for Myc, is shown in FIG. 11D.

Figure 12:
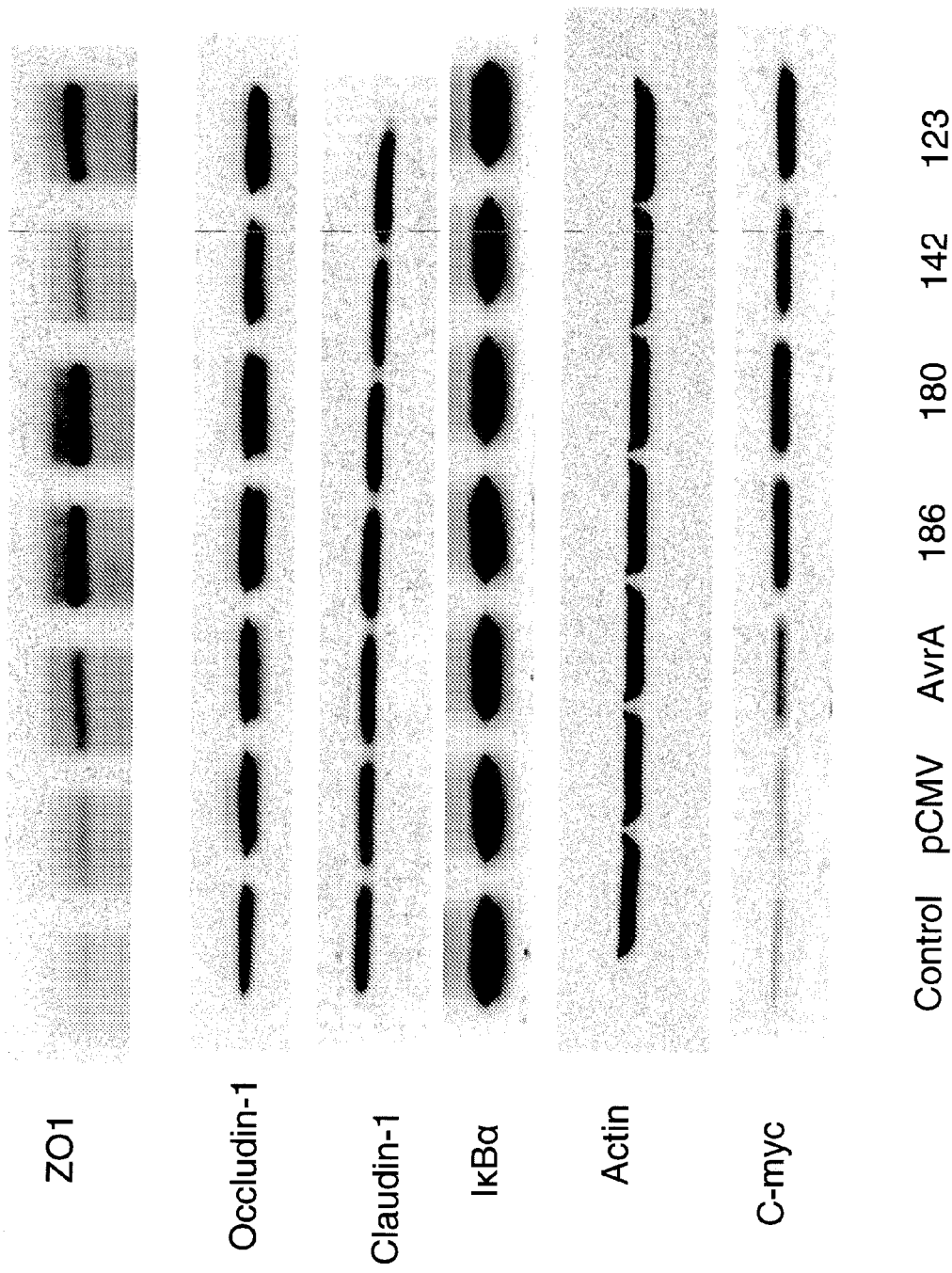

FIG. 12 illustrates TJ protein expression following transfection of HT29C19A cells with a pCMV-myc-AvrA wild-type gene construct, control empty pCMV-myc plasmid, or the pCMV-myc-AvrA-C186A, -C180A, -E142A, and -E123A plasmids encoding the point mutants. Transfections were carried out using LipofectAMINE (Invitrogen). 24 h after transfection, cells were lysed in protein-loading buffer. Equal volumes of total cell lysis were processed for immunoblotting for ZO-1, occludin-1, claudin-1, IκBα, c-myc, and β-actin. Control: normal HT29C119A without treatment; pCMV: cells transfected with empty pCMV-myc plasmid; AvrA: cells transfected with pCMV-myc-AvrA plasmid; 186: cells transfected with AvrA mutant C186A plasmid; 179: cells transfected with AvrA mutant C179A plasmid; 142: cells transfected with AvrA mutant E 142A plasmid; and 123: cells transfected with AvrA mutant H123A plasmid.

Figure 13:
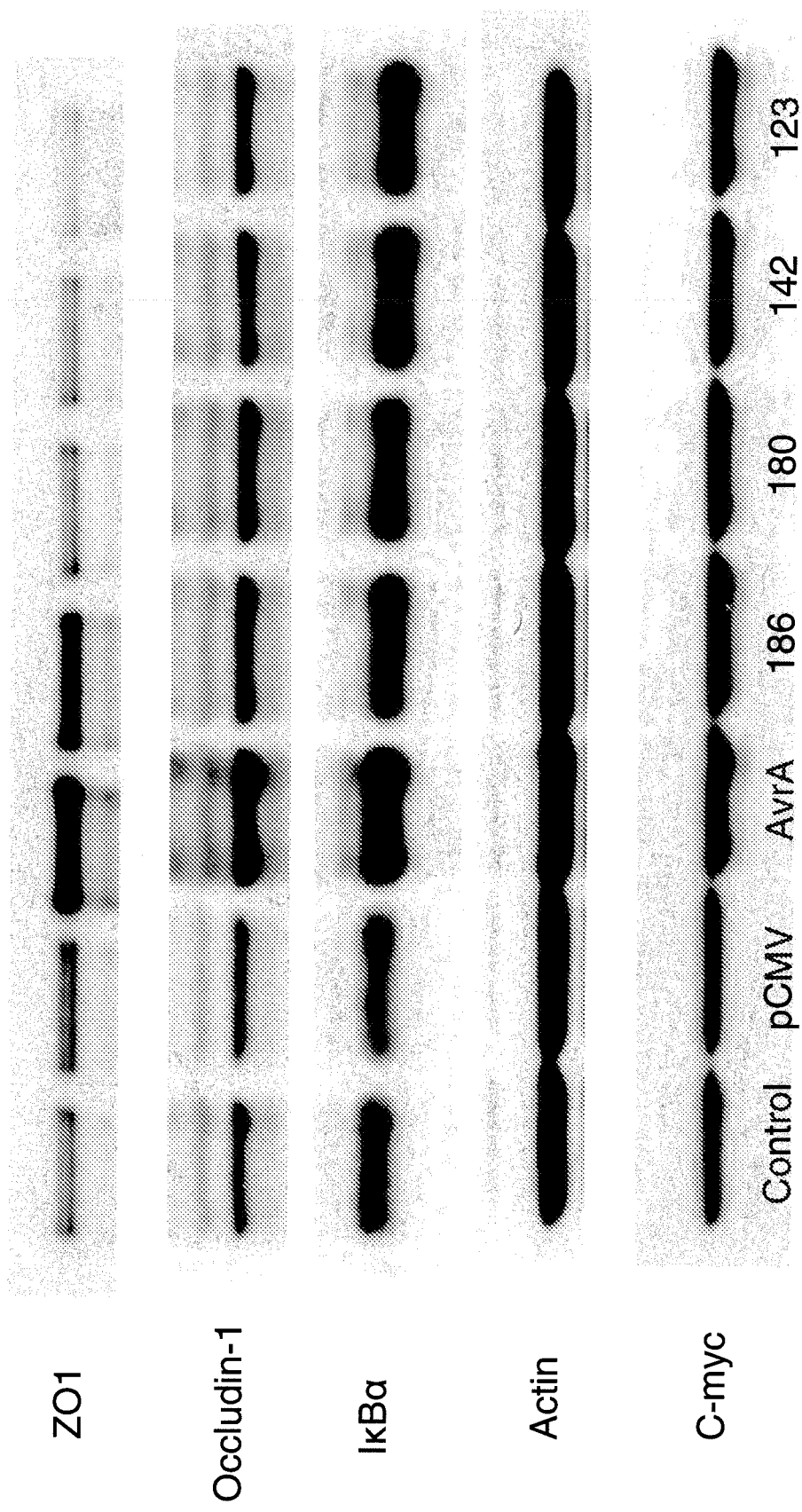

FIG. 13 is a Western blot for TJ protein expression following transfection of HT29C19A cells under the same conditions used in FIG. 12 except that TNFα was introduced for 30 minutes following 24 h transfection.

Figure 14:
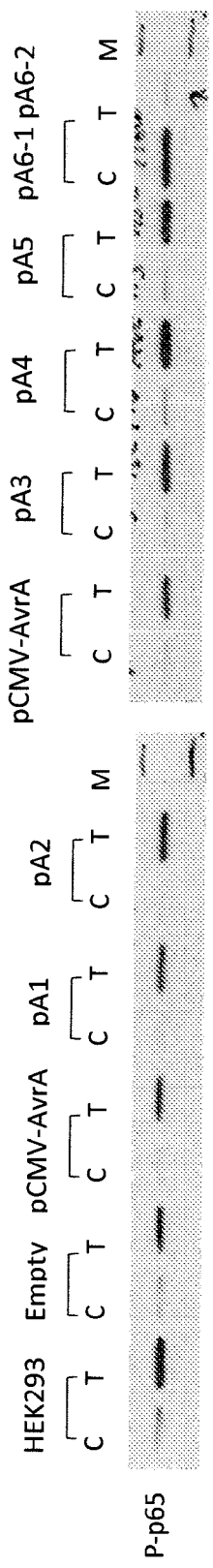

FIG. 14 illustrates phosphorylation of p65 by Western-blot after 24 hour plasmid transfection with or without TNFα incubation (10 ng/ml in each well). pA6-1 was treated with TNFα, but pA6-2 was not. Both the sequences are correct, though they were obtained from different clones when using Amp+ plate screening. C: control; T:TNF; pCMV-AvrA:full length AvrA; pA1-6: truncated AvrA 1-6.

Figure 15:
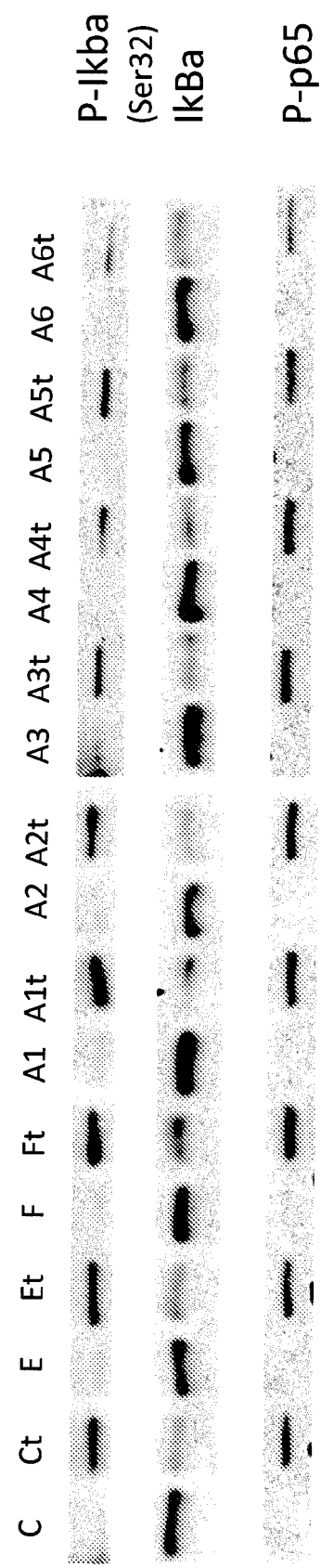

FIG. 15 illustrates a Western blot for phosphorylated IκBα, non-phosphorylated IκBα, and phosphorylated p-65 in cell lysates of HCT116 cells transfected with control (C), pCMV-empty vector (E), pCMV-AvrA:full length AvrA (F), pA1-pA6 (A1-A6) with and without TNFα exposure (t) 24 h following transfection.

Figure 16:
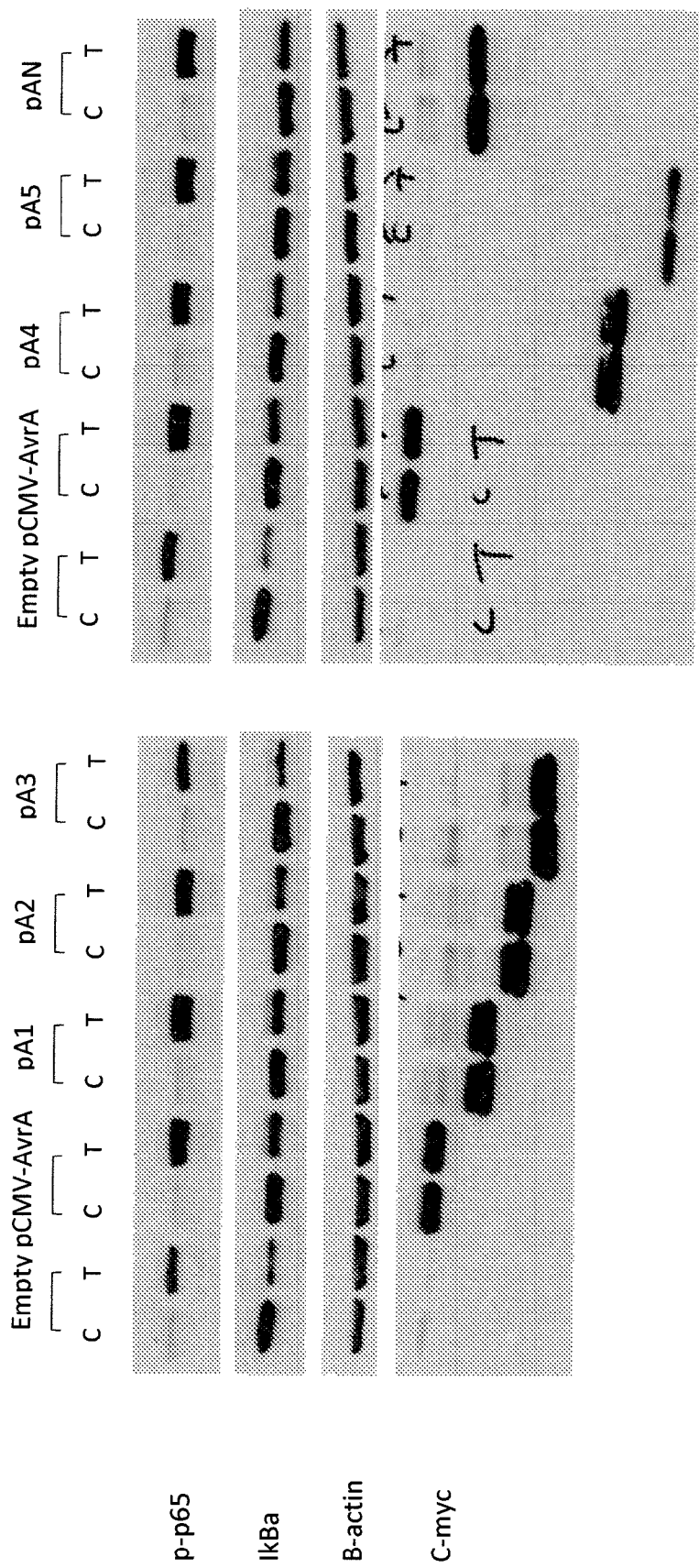

FIG. 16 illustrates a Western blot for non-phosphorylated IκBα, phosphorylated p-65, beta-actin, and C-myc in cell lysates of HCT116 cells transfected with pCMV-empty vector (E), pCMV-AvrA:full length AvrA (A), pA1-pA6 (A1-A6) with and without TNFα exposure (t) 24 h following transfection.

DETAILED DESCRIPTION OF THE INVENTION

The present invention relates to uses of the bacterial avirulence protein known as AvrA, as well as active polypeptide fragments thereof, and isolated nucleic acid molecules or expression vectors encoding the same. In particular, as noted above, the applicant has surprisingly demonstrated that AvrA is active in intestinal epithelial cells to promote the structure and function of tight junctions in intestinal epithelial tissue. Thus, AvrA and active polypeptide fragments thereof, whether administered as a pharmaceutical composition or expressed via recombinant DNA, can be used to treat an inflammatory intestinal disease or condition, manage symptoms thereof, or heal intestinal tissue damaged by such diseases of conditions.

Exemplary inflammatory intestinal diseases or conditions include, without limitation, Inflammatory Bowel Disease ("IBD"), Celiac Disease, and gastroenteritis.

IBD encompasses both ulcerative colitis and Crohn's Disease. Ulcerative colitis is an inflammatory disease of the large intestine where the intestinal mucosa becomes inflamed and develops ulcers. Ulcerative colitis is often the most severe in the rectal area, which can cause frequent diarrhea. Mucus and blood often appear in the stool if the lining of the colon is damaged. Crohn's disease differs from ulcerative colitis in the areas of the bowel it involves. It most commonly affects the last part of the small intestine, called the terminal ileum, and parts of the large intestine. However, Crohn's disease is not limited to these areas and can attack any part of the digestive tract. Crohn's disease causes inflammation that extends much deeper into the layers of the intestinal wall than ulcerative colitis does. Crohn's disease generally tends to involve the entire bowel wall, whereas ulcerative colitis affects only the lining of the bowel.

IBD is generally a chronic disorder. Symptoms of IBD include abdominal pain, diarrhea or constipation or alternating diarrhea and constipation, gas, bloating, nausea, weight loss, rectal bleeding, fatigue, and decreased appetite. Children suffering from IBD also experience delayed growth and development.

Celiac Disease is a digestive condition triggered by consumption of the protein gluten (found in most grains), which causes an immune reaction to occur in the small intestine. This immune reaction can cause damage to the surface of the small intestine and an inability to absorb certain nutrients. Symptoms of Celiac Disease generally include intermittent diarrhea, abdominal pain, and bloating. Celiac Disease is often managed solely by regulating diet.

Gastroenteritis is a catchall term for infection or irritation of the digestive tract, particularly the stomach and intestine. Gastroenteritis arises from ingestion of viruses (e.g., rotavirus, adenovirus, astrovirus, and calicivirus and small round-structured viruses (SRSVs) such as Norwalk, Southhampton, and Lonsdale viruses), certain bacteria (e.g., *Salmonella, Campylobacter, E. coli* 0157, and *Listeria monocytogenes*), or parasites. Certain medications and excessive alcohol can also irritate the digestive tract to the point of inducing gastroenteritis. Regardless of the cause, the symptoms of gastroenteritis include diarrhea, nausea and vomiting, and abdominal pain and cramps. Sufferers may also experience bloating, low fever, and overall tiredness. Typically, the symptoms last only two to three days, but some may last up to a week. Dehydration resulting from diarrhea is a major concern in children, the elderly, and anyone with an underlying disease.

In inflammatory diseases of the intestine where the integrity of the TJ system is compromised, such as IBD, Celiac Disease, and gastroenteritis, a paracellular leak ("leaky gut") and an inappropriate immune response to environmental antigens (including gluten) may develop. In one aspect of the present invention, the administration of AvrA or active polypeptide fragments thereof or nucleic acid molecules encoding the same can be used to treat or manage symptoms of these inflammatory conditions, and even promote the repair of damaged intestinal epithelium through the formation of TJ. The invention provides methods for administering these active agents in pharmaceutical compositions by encapsulated oral delivery, direct injection to the bowels, anal suppository, and enema to treat diseases involving intestinal inflammation. In accordance with the present invention, according to one embodiment the AvrA protein or polypeptide (or encoding nucleic acid) is not administered for treatment of bacterially-induced gastroenteritis.

As used herein, the term "AvrA" is intended to encompass any AvrA homolog (including YopJ), but preferably *Salmonella* AvrA homologs. A consensus sequence of *Salmonella* AvrA is provided in SEQ ID NO: 19 as follows:

```
MIFSVQELSCGGKSMLSPTTRNMGASLSPQXDVSGELNTEALTCIVERL

ESEIIDGSWIHISYEETDLEMMPFLVAQANKKYPELNLKFVMSVHELVS

SIKETRMEGVESARFXVNMGSSGIHXSVVDFRVMDGKTSVILFEPAACS

AFGPAXLALRTKAALEREQLPDCYFAMVELDIQRSSSECGIFSLALAKK

LXLEFMNLVKIHEDNICERLCGEEPFLPSDKADRYLPVSFYKHTQGXQR

LNEYVXANPAAGSSIVNKKNETLYERFDNNAVMLNDKKLSIXAHKKRIA

EYKSLLKX
``` where the consensus preferably comprises amino acids 23-302 of SEQ ID NO: 19, or alternatively amino acids 15-302 of SEQ ID NO: 19 or amino acids 1-302 of SEQ ID NO: 19, with X at position 31 being any amino acid, but preferably P or S; X at position 114 being any amino acid, but preferably L or I; X at position 124 being any amino acid, but preferably I or V; X at position 153 being optional or any amino acid, but preferably L; X at position 198 being any amino acid, but preferably Q or H; X at position 243 being any amino acid, but preferably A or V; X at position 251 being any amino acid, but preferably E or Q; X at position 287 being any amino acid, but preferably S or F; and X at position 302 being any amino acid, but preferably P or S.

Exemplary *Salmonella* AvrA homologs are shown in FIGS. 1A-B, including SEQ ID NO: 1 (*Salmonella enterica* serovar *Typhimurium*; Genbank Accession No. AAB83970, which is hereby incorporated by reference in its entirety); SEQ ID NO: 2 (*Salmonella typhimurium* LT2; Genbank Accession No. AAL21745, which is hereby incorporated by reference in its entirety); SEQ ID NO: 3 (*Salmonella enterica* subsp. *enterica* serovar Gallinarum str. 287/91; Genbank Accession No. CAR38577, which is hereby incorporated by reference in its entirety); SEQ ID NO: 4 (*Salmonella enterica* subsp. *enterica* serovar Heidelberg str. SL486; Genbank Accession No. EDZ24776, which is hereby incorporated by reference in its entirety); SEQ ID NO: 5 (*Salmonella enterica* subsp. *enterica* serovar Enteritidis str. P125109; Genbank Accession No. CAR34285, which is hereby incorporated by reference in its entirety); SEQ ID NO: 6 (*Salmonella enterica* subsp. *enterica* serovar Kentucky str. CVM29188; Genbank Accession No. EDX43702, which is hereby incorporated by reference in its entirety); SEQ ID NO: 7 (*Salmonella enterica* subsp. *enterica* serovar Saintpaulia, strain SARA23; Genbank Accession No. EDZ12687, which is hereby incorporated by reference in its entirety); SEQ ID NO: 8 (*Salmonella enterica* subsp. *enterica* serovar Agona strain SL483; Genbank Accession No. ACH48766, which is hereby incorporated by reference in its entirety); and SEQ ID NO: 9 (*Salmonella enterica* subsp. *enterica* serovar Schwarzengrund str. CVM19633; Genbank Accession No. ACF92027, which is hereby incorporated by reference in its entirety). These nine sequences shown in FIGS. 1A-B share between 97-100% identity.

Other *Salmonella* AvrA homologs are also known in the art, including those for strains HI_N05-537, SL317, CVM23701, SL254, CT__02021853, SL480, SL491, SARA29, SL476, CVM29188, CDC 191, and RI__05P066 (see, e.g., Genbank Accession Nos. ZP__02832444.1, ZP__02697922.1, ZP__02575265.1, ZP__02679382.1, ZP__02352067.1, ZP__02568199.1, ZP__02660958.1, ZP__02704254.1, ZP__02344048.1, ZP__02667530.1, ZP__02671513.1, ZP__02560426.1, ZP__02655988.1, ZP__02683990.1, AAL21745.1, AF250312.1, each of which is hereby incorporated by reference in its entirety).

According to one embodiment, the isolated AvrA proteins or polypeptides include those that are at least about 75 percent identical, more preferably at least about 80 or 85 percent, most preferably at least about 90 or 95 percent identical, to the amino acid sequence of residues 23-302 (301) of SEQ ID NO: 19 (consensus AvrA).

Amino acid sequence homology, or sequence identity, is determined by optimizing residue matches and, if necessary, by introducing gaps as required. See also Needleham et al., "A General Method Applicable to the Search for Similarities in the Amino Acid Sequence of Two Proteins," *J. Mol. Biol.* 48:443-453 (1970); Sankoff et al., Chapter One in *Time Warps, String Edits, and Macromolecules: The Theory and Practice of Sequence Comparison*, Addison-Wesley, Reading, Mass. (1983); and software packages from IntelliGenetics, Mountain View, Calif.; and the University of Wisconsin Genetics Computer Group, Madison, Wis., each of which is hereby incorporated by reference in its entirety. Sequence identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. The conservation may apply to biological features, functional features, or structural features. Homologous amino acid sequences are typically intended to include natural polymorphic or allelic and interspecies variations of a protein sequence. In the absence of including gaps and conserved substitutions, identity measures will be at least about 75%, preferably at least about 80%, and more preferably at least about 90% for AvrA homologs.

Other embodiments of these proteins or polypeptide include fusion proteins that are formed, e.g., by an in-frame gene fusion to result in the expression of AvrA protein or polypeptide fragment thereof fused to a second polypeptide, such as an affinity tag for purification or identification, a fluorescent polypeptide for in situ visualization of the fusion protein, or any polypeptides that promote intestinal epithelial cell uptake of the fusion protein.

It is believed that fusion proteins may be used to enhance uptake of the AvrA protein or polypeptide, but that such enhancement is not required to effectively treat IBD or celiac disease, where TJ formations may be lacking Pre-existing disruption of the TJ will facilitate absorption of the AvrA protein or polypeptide, and thereby promote TJ function post-administration.

Fragments of the above-identified proteins or polypeptides can also be used according to the present invention. Fragments having the ability to promote TJ function can be screened in vitro as described in the accompanying examples. Exemplary fragments include, without limitation, those missing N-terminal portions of the AvrA protein but possessing the C-terminal portions thereof.

Suitable fragments can be produced by several means. Subclones of the gene encoding a known protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial or other host cells to yield a smaller protein or polypeptide that can be tested for activity, e.g., as a product calcium signaling.

In another approach, based on knowledge of the primary structure of the protein, fragments of the protein-coding gene may be synthesized using the PCR technique together with specific sets of primers chosen to represent particular portions of the protein (Erlich et al., "Recent Advances in the Polymerase Chain Reaction," *Science* 252:1643-51 (1991), which is hereby incorporated by reference in its entirety). These can then be cloned into an appropriate vector for expression of a truncated protein or polypeptide from bacterial or other cells as described above.

As an alternative, fragments of a protein can be produced by digestion of a full-length protein with proteolytic enzymes like chymotrypsin or *Staphylococcus* proteinase A, or trypsin. Different proteolytic enzymes are likely to cleave different proteins at different sites based on the amino acid sequence of the particular protein. Some of the fragments that result from proteolysis may be active AvrA polypeptides, and can be screened in vitro for their ability to promote TJ function as described in the accompanying examples.

Chemical synthesis can also be used to make suitable fragments. Such a synthesis is carried out using known amino acid sequences for the polypeptide being produced. Alternatively, subjecting a full length protein to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Other variants include those possessing single or multiple substitutions of one or more domains. Upon expression of these variants in intestinal epithelial host cells, activity of the variants can be screened using the methods described herein. Variants may include one or more conserved substitutions, as identified above.

The proteins or polypeptides used in accordance with the present invention are preferably produced in purified form (preferably at least about 80%, more preferably 90%, pure) by conventional techniques, preferably by isolation from recombinant host cells. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the protein or polypeptide of interest can be subjected to gel filtration in an appropriately sized dextran or polyacrylamide column to separate the proteins. If necessary, the protein fraction may be further purified by HPLC.

Also encompassed by the present invention are isolated nucleic acid molecules encoding the AvrA proteins or polypeptides of the present invention. The isolated nucleic acid molecule can be DNA or RNA, and it can also contain non-naturally occurring nucleic acids.

Exemplary DNA molecules encoding AvrA are shown in FIGS. 2A-E, including without limitation, SEQ ID NO: 10 (*Salmonella enterica* serovar *Typhimurium*; Genbank Accession No. AF013573, which is hereby incorporated by reference in its entirety); SEQ ID NO: 11 (*Salmonella typhimurium* LT2; Genbank Accession No. AE006468, which is hereby incorporated by reference in its entirety); SEQ ID NO: 12 (*Salmonella enterica* subsp. *enterica* serovar Gallinarum str. 287/91; Genbank Accession No. AM933173, which is hereby incorporated by reference in its entirety); SEQ ID NO: 13 (*Salmonella enterica* subsp. *enterica* serovar Heidelberg str. SL486; Genbank Accession No. ABEL01000005, which is hereby incorporated by reference in its entirety); SEQ ID NO: 14 (*Salmonella enterica* subsp. *enterica* serovar Enteritidis str. P125109; Genbank Accession No. AM933172, which is hereby incorporated by reference in its entirety); SEQ ID NO: 15 (*Salmonella enterica* subsp. *enterica* serovar Kentucky str. CVM29188; Genbank Accession No. ABAK02000001, which is hereby incorporated by reference in its entirety); SEQ ID NO: 16 (*Salmonella enterica* subsp. *enterica* serovar Saintpaulia, strain SARA23; Genbank Accession No. ABAN01000004, which is hereby incorporated by reference in its entirety); SEQ ID NO: 17 (*Salmonella enterica* subsp. *enterica* serovar Agona strain SL483; Genbank Accession No. CP001138, which is hereby incorporated by reference in its entirety); and SEQ ID NO: 18 (*Salmonella enterica* subsp. *enterica* serovar Schwarzengrund str. CVM19633; Genbank Accession No. CP001127, which is hereby incorporated by reference in its entirety). The DNA molecules encoding other homologous AvrA proteins, including those identified above, have been identified in Genbank.

Also encompassed by the present invention are nucleic acid molecules that encode other AvrA homologs. Preferably, these AvrA homologs share at least 75 percent identity at the amino acid level, and are encoded by a nucleic acid molecule capable of hybridizing over substantially its full length to the complement of any one of SEQ ID NOS: 10-18 under stringent hybridization and wash conditions. Exemplary stringent hybridization and wash conditions include, without limitation, hybridization carried out for about 8 to about 20 hours at a temperature of about 42° C. using a hybridization medium that includes 0.9× sodium citrate ("SSC") buffer, followed by washing for about 5 minutes to about 1 hour with 0.2×SSC buffer at 42° C. Higher stringency can readily be attained by increasing the temperature for either hybridization or washing conditions or decreasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 55° C. up to and including about 65° C. (inclusive of all temperatures in such range) for about 8 up to about 20 hours in a hybridization medium containing 1M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 µg/ml E. coli DNA, followed by washing for about 5 minutes to about 1 hour, at about 55° C. up to and including about 65° C. (inclusive of all temperatures in such range) in a 0.2×SSC buffer.

Also encompassed by the present invention are codon-enhanced nucleic acid molecules that have their codons modified to enhance expression in a particular type of host cell during recombinant production and purification thereof.

The preparation of the nucleic acid constructs of the present can be carried out using methods well known in the art. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Suitable vectors include, but are not limited to, vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Several viral systems including murine retrovirus, adenovirus, parvovirus (adeno-associated virus), vaccinia virus, and herpes virus, such as herpes simplex virus and Epstein-Barr virus, and retroviruses, such as MoMLV have been developed as therapeutic gene transfer vectors (Nienhuis et al., *Hematology*, Vol. 16:*Viruses and Bone Marrow*, N. S. Young (ed.), pp. 353-414 (1993), which is hereby incorporated by reference in its entirety). Viral vectors provide a more efficient means of transferring genes into cells as compared to other techniques such as calcium phosphate or DEAE-dextran-mediated transfection, electroporation, or microinjection. It is believed that the efficiency of viral transfer is due to the fact that the transfer of DNA is a receptor-mediated process (i.e., the virus binds to a specific receptor protein on the surface of the cell to be infected.) Among the viral vectors that have been cited frequently for use in preparing transgenic mammal cells are adenoviruses (U.S. Pat. No. 6,203,975 to Wilson, which is hereby incorporated by reference in its entirety). In one embodiment of the present invention, a nucleic acid encoding the AvrA protein of the present invention is incorporated into an adenovirus or adeno-associated expression vector.

Once a suitable expression vector is selected, the desired nucleic acid sequence(s) cloned into the vector using standard cloning procedures in the art, as described by Sambrook et al., Molecular Cloning: *A Laboratory Manual, Cold Springs Laboratory*, Cold Springs Harbor, N.Y. (1989), or U.S. Pat. No. 4,237,224 to Cohen and Boyer, each of which is hereby incorporated by reference in its entirety. The vector is then introduced to a suitable host.

A variety of host-vector systems may be utilized to express the recombinant protein or polypeptide inserted into a vector as described above. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria, viral vectors, either with or without biolistics. The expression elements of these vectors vary in their strength and specificities. Depending upon the host-vector system utilized, any one of a number of suitable transcription and translation elements can be used to carry out this and other aspects of the present invention.

Different genetic signals and processing events control many levels of gene expression (e.g., DNA transcription and messenger RNA ("mRNA") translation). Transcription of DNA is dependent upon the presence of a promoter, which is a DNA sequence that directs the binding of RNA polymerase, and thereby promotes mRNA synthesis. The DNA sequences of eukaryotic promoters differ from those of prokaryotic promoters. Furthermore, eukaryotic promoters and accompanying genetic signals may not be recognized in, or may not function in, a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the PR and PL promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Common promoters suitable for directing expression in mammalian cells include, without limitation, SV40, MMTV, metallothionein-1, adenovirus E1a, CMV, immediate early, immunoglobulin heavy chain promoter and enhancer, and RSV-LTR. The promoters can be constitutive or, alternatively, tissue-specific or inducible. In addition, in some circumstances inducible (TetOn) tissue-specific promoters can be used. Exemplary intestinal epithelial cell-specific promoters include, without limitation, promoters of sucrase-isomaltase gene (Rodolosse et al., "A Limited Upstream Region of the Human Sucrase-isomaltase Gene Confers Glucose-regulated Expression on a Heterologous Gene," *Biochem. J.* 315: 301-6 (1996); Traber et al., "Regulation of Sucrase-isomaltase Gene Expression Along the Crypt-villus Axis of Rat Small Intestine," *Mol. Cell. Biol.* 12:3614-27 (1992), each of which is hereby incorporated by reference in its entirety); lactase-phlorizin hydrolase gene (Boll et al., "Structure of the Chromosomal Gene and cDNAs Coding for Lactase-phlorizin Hydrolase in Humans with Adult-type Hypolactasia or Persistence of Lactase," *Am. J. Hun. Genet.* 48:889-902 (1991); Troelsen et al., "1 kb of the Lactase-phlorizin Hydrolase Promoter Directs Post-weaning Decline and Small Intestinal-specific Expression in Transgenic Mice," *FEBS Lett.* 342:291-6 (1994), each of which is hereby incorporated by reference in its entirety); carbonic anhydrase gene (Brady et al., "The Human Carbonic Anhydrase I Gene has Two Promoters with Different Tissue Specificities," *Biochem. J.* 277: 903-5 (1991); Drummond et al., "The Caudal-type Homeobox Protein Cdx-2 Binds to the Colon Promoter of the Carbonic Anhydrase 1 Gene," *Eur. J. Biochem.* 236:670-81 (1996); Sowden et al., "Expression from the Proximal Promoter of the Carbonic Anhydrase 1 Gene as a Marker for Differentiation in Colon Epithelia," *Differentiation* 53:67-74 (1993), each of which is hereby incorporated by reference in its entirety); T3b gene (Aihara et al., "The T3b Gene Promoter Directs Intestinal Epithelial Cell-specific Expression in Transgenic Mice," *FEBS Letters* 463(1-2):185-188 (1999), which is hereby incorporated by reference in its entirety); CCL25 gene (Ericsson et al., "Functional Characterization of the CCL25 Promoter in Small Intestinal Epithelial Cells Suggests a Regulatory Role for Caudal-Related Homeobox (Cdx) Transcription Factors," *J. Immunol.* 176(6):3642-3651 (2006), which is hereby incorporated by reference in its entirety); FABP2 gene (intestinal) (Damcott et al., "Variation in the FABP2 Promoter Alters Transcriptional Activity and Is Associated with Body Composition and Plasma Lipid Levels," *Human Genet.* 112(5-6):610-6 (2003); Formanack et al. "Variation in the FABP2 Promoter Affects Gene Expression: Implications for Prior Association Studies," *Diabetologia* 47(2):349-51 (2004), each of which is hereby incorporated by reference in its entirety); and aminopeptidase gene (Olsen et al., "HNF1 alpha Activates the Aminopeptidase N Promoter in Intestinal (Caco-2) Cells," *FEBS Lett.* 342:325-8 (1994), which is hereby incorporated by reference in its entirety).

Specific initiation signals are also required for efficient gene transcription and translation in prokaryotic cells. These transcription and translation initiation signals may vary in "strength" as measured by the quantity of gene specific messenger RNA and protein synthesized, respectively. The nucleic acid expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used. Depending on the vector system and host utilized, any number of suitable transcription and/or translation elements, including constitutive, inducible, and repressible promoters, as well as minimal 5' promoter elements, enhancers or leader sequences may be used.

In eukaryotic systems, the polyadenylation signal sequence may be selected from any of a variety of polyadenylation signal sequences known in the art. Preferably, the polyadenylation signal sequence is the SV40 late polyadenylation signal sequence. The construct may also include sequences in addition to promoters which enhance expression in intestinal epithelial cells (e.g., enhancer sequences, introns, etc.). For example, the construct can include one or more introns, which can increase levels of expression of the DNA of interest, particularly where the DNA of interest is a cDNA (e.g., contains no introns of the naturally-occurring sequence). Any of a variety of introns known in the art may be used. One preferred intron is the human β-globin intron, which can be inserted in the construct at a position 5' to the DNA of interest.

Typically, when a recombinant host is produced, an antibiotic or other compound useful for selective growth of the transgenic cells only is added as a supplement to the media. The compound to be used will be dictated by the selectable marker element present in the plasmid with which the host was transformed. Suitable genes are those which confer resistance to gentamycin, G418, hygromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually.

The selection marker employed will depend on the target species and/or host or packaging cell lines compatible with a chosen vector.

A nucleic acid molecule encoding the desired product of the present invention (AvrA protein or polypeptide fragment, or fusion protein), a promoter molecule of choice, including, without limitation, enhancers, and leader sequences; a suitable 3' regulatory region to allow transcription in the host, and any additional desired components, such as reporter or marker genes, can be cloned into the vector of choice using standard cloning procedures in the art, such as described in Sambrook et al., *Molecular Cloning: A Laboratory Manual*, Cold Spring Laboratory, Cold Spring Harbor, N.Y. (1989); Ausubel et al., *"Short Protocols in Molecular Biology,"* New York:Wiley (1999), and U.S. Pat. No. 4,237,224 to Cohen and Boyer, each of which is hereby incorporated by reference in its entirety.

Once the expression vector has been prepared, it is ready to be incorporated into a host. Recombinant molecules can be introduced into cells by any suitable means including, without limitation, via transformation (if the host is a prokaryote), transfection (if the host is a eukaryote), transduction (if the host is a virus), conjugation, mobilization, or electroporation, lipofection, protoplast fusion, mobilization, particle bombardment, or electroporation, using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety.

Suitable hosts include, but are not limited to, bacteria, virus, yeast, and mammalian cells (e.g., human cells, whether as a cell line or primary cell isolates), including, without limitation, whole organisms.

Accordingly, another aspect of the present invention relates to a method of making a recombinant cell. Basically, this method is carried out by transforming a host with a nucleic acid construct of the present invention under conditions effective to yield transcription of the nucleic acid molecule in the host. Preferably, a nucleic acid construct containing a suitable nucleic acid molecule of the present invention is stably inserted into the genome of the recombinant host as a result of the transformation. Alternatively, the construct can be intentionally used for transient transfection, which results in the loss of the transgene phenotype over time.

As noted above, the present invention contemplates therapeutic administration to a mammalian subject, preferably though not exclusively human subject, of either the AvrA protein or polypeptide, or fusion protein containing the same, or a nucleic acid molecule or expression vector of the present invention. Although the descriptions of pharmaceutical compositions provided herein are principally directed to pharmaceutical compositions that are suitable for administration to humans, it will be understood by the skilled artisan that such compositions are generally suitable for administration to animals of all sorts, particularly mammals. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, domesticated animals, and animals used in agriculture.

Therapeutic administration thereof can be achieved by any suitable means, but preferably via parenteral (e.g., intravenous, intraarterial, intramuscular, subcutaneous injection), oral (e.g., dietary), topical, nasal, rectal, or via slow releasing microcarriers. Oral, parenteral and intravenous administration are preferred modes of administration. Formulation of the compound to be administered will vary according to the route of administration selected (e.g., solution, emulsion, gels, aerosols, and capsule). An appropriate pharmaceutical composition containing the protein or polypeptide or nucleic acid to be delivered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (see generally, Remington's Pharmaceutical Science, 16th Edition, Mack, Ed. (1980), which is hereby incorporated by reference in its entirety).

Therapeutically effective administration of the AvrA protein or polypeptide or fusion protein of the invention typically occurs in doses ranging from 0.1 mg/kg of body weight to 25 mg/kg. In some embodiments, the therapeutically effective dose is 0.3, 1.0, 3, 5, 7.5, 10 and 25 mg/kg. An amount effective to treat the disorders hereinbefore described depends upon such factors as the efficacy of the active compounds, the molecular weight of the agent chosen, the nature and severity of the disorders being treated and the weight of the mammal. However, a unit dose will normally contain 0.01 to 200 mg, for example 20 to 100 mg, of the compound of the invention. "Unit dose" includes a discrete amount of the pharmaceutical composition comprising a predetermined amount of the active ingredient. In some embodiments, a dose of 1-200 mg of AvrA is injected as a single bolus in a human in need of treatment, including but not limited to a human with inflammatory bowel disease or celiac disease. In some embodiments, a dose of 20 to 100 mg is administered. In another embodiment, 1-200 mg of AvrA is administered orally.

A subject who has or is at risk of IBD or CD is treated prior to the onset of one or more disease symptoms. Alternatively, the subject is treated concomitant to or after the onset of one or more disease symptoms. Therefore, the invention provides a method for preventing or reducing a symptom of inflammatory intestinal disease or condition in a mammalian subject, by identifying a mammalian subject at risk of the inflammatory intestinal disease or condition, and administering to the identified subject a therapeutically effective AvrA protein or polypeptide or encoding nucleic acid of the invention. A subject at risk of inflammatory intestinal disease or condition is identified on the basis of family history, i.e., one or more parents, grandparents, siblings, issue, or other relatives have been diagnosed with IBD or Celiac Disease. Alternatively, a subject at risk of IBD is identified because the subject has a prior history of inflammatory bowel disease, or celiac disease, but is currently asymptomatic.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or diglycerides. Other parentally-administrable formulations that are useful include those, which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

"Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

An AvrA protein or polypeptide or fusion protein, or encoding nucleic acid, of the invention can be delivered orally or via enema/suppository to treat the inflammatory intestinal disease or condition, or to control symptoms thereof. For oral delivery, the present invention provides pharmaceutical compositions such that the AvrA protein or polypeptide or fusion protein, or encoding nucleic acid, can pass into the small intestine without being destroyed by the harsh acidic environment of the stomach.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

In one embodiment, the present invention provides AvrA encapsulated in a polymer or other material that is resistant to acid hydrolysis or acid breakdown. In one embodiment, this formulation provides rapid release of AvrA upon entry into the duodenum. Accordingly, the invention includes a composition containing an AvrA protein or polypeptide or fusion protein and a pharmaceutically-acceptable acid-resistant ("enteric") carrier. By acid-resistant is meant that the carrier or coating does not dissolve in an acidic environment. An acidic environment is characterized by a pH of less than 7. The acid-resistant carrier is resistant to acids at pH less than about 4.0. Preferably, the carrier does not dissolve in pH 2-3. Most preferably, it does not dissolve in pH of less than 2. The coating dissolves after the pH is greater than about 4.0. For example, the coating dissolves in a neutral environment as is encountered in the small intestine, and does not dissolve in an acidic environment as is encountered in the stomach. Alternatively, the enteric coating dissolves when exposed to specific metabolic event such as an encounter with a digestive enzyme that is found in the small intestine. For example, the coating is digested by a pancreatic enzyme such as trypsin, chymotrypsin, or a pancreatic lipase. Enteric coating materials are known in the art, e.g., malic acid-propane 1,2-diol. Cellulose derivatives, e.g., cellulose acetate phthalate or hydroxypropyl methylcellulose phthalate (HPMCP), are also useful in enteric acid-resistant coatings. Other suitable enteric coatings include cellulose acetate phthalate, polyvinyl acetate phthalate, methylcellulose, hydroxypropylmethylcellulose phthalate and anionic polymers of methacrylic acid and methyl methacrylate. Another suitable enteric coating is a water emulsion of ethylacrylate methylacrylic acid copolymer, or hydroxypropyl methyl cellulose acetate succinate (HPMAS). See, e.g., U.S. Pat. Nos. 5,591,433, 5,750,104 and 4,079,125, each of which is hereby incorporated by reference in its entirety. An enteric coating is designed to resist solution in the stomach and to dissolve in the neutral or alkaline intestinal fluid. See also coatings described in Wilding et al., "Targeting of Drugs and Vaccines to the Gut," *Pharmac. Ther.* 62:97-124 (1994), which is hereby incorporated by reference in its entirety. In another embodiment, lyophilized, particulate AvrA mixed with bicarbonate (as buffer) is coated with Eudragit S100, L30D or L 100-44 according to the manufacturer's instructions (Evonik Industries).

In another embodiment, the formulations of the invention are those used successfully with lactase (see U.S. Pat. No. 6,008,027 to Langner et al., which is hereby incorporated by reference in its entirety). In this embodiment, gelatin capsules are filled with 50-90% lyophilized AvrA, the remaining capacity being filled with stabilizing dessicants such as silicon oxide, silicon dioxide or microcrystalline cellulose and bicarbonate buffer. The capsules are enterically coated with Eudragit polymer (Evonik Industries) or polyvinyl acetate phthalate (Sureteric, Colorcon) and vacuum dried prior to use. Similarly, diastase has been formulated with Eudragit RS 100 and cellulase acetate phthalate coatings for enteric use, and the present invention provides novel formulations that resemble these but contain AvrA instead of diastase (Vyas et al., "Enteric Spherules of Diastase in Enzyme Preparations, *J. Microencapsulation* 8: 447-454 (1991), which is hereby incorporated by reference in its entirety).

An alternative stabilizing agent that ensures AvrA delivery is a mammalian colostrum, whether produced as a hyperimmune colostrum for antibody-based therapeutics or as an in vitro mixture of the therapeutic agent and colostrum. See PCT Application Publ. No. WO/2003/080082 to Rawlin et al., which is hereby incorporated by reference in its entirety.

To demonstrate that a formulation can increase AvrA bioavailability in the small intestine, one uses any of the following tests. First, the ability of AvrA activity to withstand 0.5-2 h of simulated gastric treatment (pepsin, in 0.1N HCl, pH 2) can be evaluated. If >10% activity can be reproducibly retained, the formulation is exposed to simulated conditions in the duodenum (pH 6.5 buffer containing trypsin, chymotrypsin and carboxypeptidase at a 1:100 molar ratio and elastase at a 1:500 ratio to the AvrA). In one embodiment, full release of AvrA activity is achieved within 15 minutes. Formulations that satisfy the above criteria can be tested in or more animal models of IBD.

For oral delivery of nucleic acid-based therapies, a number of different approaches can be employed. For example, naked DNA can be delivered in accordance with U.S. Pat. No. 6,831,070 to German et al., which is hereby incorporated by reference in its entirety. Alternatively, the nucleic acid can be formulated into a delivery vehicle, such as the chitosan hexamer-PEI vector described in Ouji et al., "Polyethyleneimine/chitosan Hexamer-mediated Gene Transfection into Intestinal Epithelial Cell Cultured in Serum Containing Medium," *J. Biosci. Bioeng.* 94(1):81-3 (2002), which is hereby incorporated by reference in its entirety, or chitosan-DNA nanoparticles containing an AAV expression vector as described in Chen et al., "Transfection of mEpo Gene to Intestinal Epithelium in vivo Mediated by Oral Delivery of Chitosan-DNA Nanoparticles," *World J Gastroenterol* 10(1):112-116 (2004), which is hereby incorporated by reference in its entirety.

The AvrA proteins or polypeptides and encoding nucleic acids of the present invention can also be administered in combination with other known therapies for IBD or CD or gastroenteritis. Such therapies include, without limitation, anti-inflammatory drugs such as sulfasalazine, corticosteroids such as prednisone, and immune system suppressors such as azathioprine and mercaptopurine. An antibiotic, such as metronidazole, may also be helpful for killing germs in the intestines, especially for Crohn's disease. To help treat symptoms, anti-diarrheals, laxatives, and pain relievers can also be used.

Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Thus, the compounds of the invention and the other pharmacologically active agent may be administered to a patient simultaneously, sequentially or in combination. If administered sequentially, the time between administrations of each individual drug generally varies from 0.1 to about 48 hours. More preferably, the time between administrations varies from 4 hours and 24 hours. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

EXAMPLES

The following Examples are meant to be non-limiting and illustrative of the invention.

Materials and Methods

Cell Culture:

T84 epithelial cells (American Type Culture Collection, Manassas, Va.) were grown in 1:1 DMEM and Ham's F-12 medium supplemented with 15 mM HEPES (pH 7.5), 14 mM NaHCO3, antibiotics, and 5% neonatal calf serum. HT29-CL19A cells were grown in DMEM (high glucose, 4.5 g/L) containing 5% (vol/vol) fetal bovine serum, 50 ug/ml streptomycin, and 50 U/ml penicillin. Monolayers of T84 and HT29-CL19A cells were grown on permeable supports (0.33 or 4.67 $cm^2$, 0.4 μm pore. Costar, Cambridge, Mass.) and utilized 6-14 days (T84) or 4-6 days (HT-29-CL19A) after being plated.

Bacterial Strains and Growth Conditions:

Bacteria strains included wild-type (WT) *S. Typhimurium* ATCC 14028s; *S. Typhimurium* PhoP$^c$, a derivative of wild-type *Salmonella* SL14028 (Miller et al., "Constitutive Expression of the phoP Regulon Attenuates *Salmonella* Virulence and Survival within Macrophages," *J Bacteriol* 172:2485-2490 (1990), which is hereby incorporated by reference in its entirety) with AvrA gene and protein expression; *Salmonella* PhoP$^c$ mutant strain lacking the AvrA gene (PhoP$^c$AvrA−); PhoP$^c$ AvrA− transcomplemented with a plasmid encoding WT AvrA (PhoP$^c$ AvrA−/AvrA+) (Collier-Hyams et al., "Cutting Edge: *Salmonella* AvrA Effector Inhibits the Key Proinflammatory, Anti-apoptotic NF-kappa B Pathway," *J Immunol* 169:2846-2850 (2002), which is hereby incorporated by reference in its entirety); and *Escherichia coli* F18 (a flagellated nonpathogenic strain (McCormick et al., "*Salmonella typhimurium* Attachment to Human Intestinal Epithelial Monolayers: Transcellular Signalling to Subepithelial Neutrophils," *J Cell Biol* 123:895-907 (1993); Kohler et al., "*Salmonella enterica* serovar *Typhimurium* Regulates Intercellular Junction Proteins and Facilitates Transepithelial Neutrophil and Bacterial Passage," *Am J Physiol Gastrointest Liver Physiol* 293:G178-187 (2007), each of which is hereby incorporated by reference in its entirety). *S. Typhimurium* mutant PhoP$^c$, PhoP$^c$ AvrA−, and PhoP$^c$ AvrA−/AvrA+ were provided by Dr. Andrew Neish of Emory University. The wild-type strain *Salmonella* ATCC 14028s used in this study is known to have the AvrA gene but has low AvrA protein expression (Streckel et al., "Expression Profiles of Effector Proteins SopB, SopD1, SopE1, and AvrA Differ with Systemic, Enteric, and Epidemic Strains of *Salmonella enterica*," *Mol Nutr Food Res* 48:496-503 (2004); Ben-Barak et al., "The Expression of the Virulence-associated Effector Protein Gene avrA is Dependent on a *Salmonella enterica*-specific Regulatory Function," *Int J Med Microbiol* 296:25-38 (2006), each of which is hereby incorporated by reference in its entirety). Wild-type *S. Typhimurium* AvrA+ was generated by transforming with the pWSK29-AvrA plasmid and ampicillin-resistance selected. Bacterial growth conditions were as follows: non-agitated microaerophilic bacterial cultures were prepared by inoculation of 10 ml of Luria-Bertani broth with 0.01 ml of a stationary phase culture, followed by overnight incubation (~18 h) at 37° C., as previously described (McCormick et al., "*Salmonella typhimurium* Attachment to Human Intestinal Epithelial Monolayers: Transcellular Signalling to Subepithelial Neutrophils," *J Cell Biol* 123:895-907 (1993), which is hereby incorporated by reference in its entirety). Bacterial overnight cultures were concentrated 33-fold in Hank's balanced salt solution (HBSS) supplemented with 10 mM HEPES, pH 7.4.

PhoP$^c$ is a PhoP-PhoQ constitutive mutation of a WT *Salmonella Typhimurium* strain 14028s that increases the expression of PhoP-activated genes, represses the synthesis of approximately 20 proteins encoded by the PhoP-repressed genes, and attenuates virulence (Miller et al., "Constitutive Expression of the phoP Regulon Attenuates *Salmonella* Virulence and Survival within Macrophages," *J Bacteriol* 172:2485-2490 (1990), which is hereby incorporated by reference in its entirety). Reed et al. showed that PhoP$^c$ has similar adherence ability as the WT *Salmonella* and is less invasive than the WT *Salmonella* using the MDCK and T84 cell models (Reed et al., "The *Salmonella typhimurium* Flagellar Basal Body Protein FliE Is Required for Flagellin Production and to Induce a Proinflammatory Response in Epithelial Cells," *J Biol Chem* 277:13346-13353 (2002), which is hereby incorporated by reference in its entirety). A previous study demonstrated that PhoP$^c$ is able to inhibit the activation of the proinflammatory NF-κB pathway (Neish et al., "Prokaryotic Regulation of Epithelial Responses by Inhibition of IκB-alpha Ubiquitination," *Science* 289:1560-1563 (2000), which is hereby incorporated by reference in its entirety). Further study showed that AvrA expression in PhoP$^c$ plays an importance role in attenuating the NF-κB activity by stabilizing IκBα, the inhibitor of NF-κB (Collier-Hyams et al., "Cutting Edge: *Salmonella* AvrA Effector Inhibits the Key Proinflammatory, Anti-apoptotic NF-kappa B Pathway," *J Immunol* 169:2846-2850 (2002); Ye et al., "*Salmonella* effector AvrA Regulation of Colonic Epithelial Cell Inflammation by Deubiquitination," *Am J Pathol* 171:882-892 (2007), each of which is hereby incorporated by reference in its entirety).

Bacterial Colonization in the Polarized Epithelial Cells In Vitro:

Polarized human colonic epithelial cells were colonized with equal numbers of the indicated bacteria for 30 min, washed with HBSS, and incubated in DMEM containing gentamicin (500 μg/ml) for the times indicated in previous studies (Ye et al., "*Salmonella* effector AvrA Regulation of Colonic Epithelial Cell Inflammation by Deubiquitination," *Am J Pathol* 171:882-892 (2007); Sun et al., "Bacterial Activation of Beta-catenin Signaling in Human Epithelia," *Am J Physiol Gastrointest Liver Physiol* 287:G220-227 (2004), each of which is hereby incorporated by reference in its entirety). The first 30-minute incubation allowed bacteria to contact the surface of the epithelial cells and inject the effectors in the host cells. After extensive HBSS washing, the extracellular bacteria were washed away. Incubation with gentamicin inhibited the growth of bacteria. In this way, the affect of the bacterial effectors injected into the host cells was assessed.

Streptomycin pre-treated mouse model: Animal experiments were performed using specific-pathogen-free female C57BL/6 mice (Taconic) that were 6-7 weeks old. The protocol was approved by the University of Rochester Committee on Animal Resources Water and food were withdrawn 4 h before oral gavage with 7.5 mg/mouse of streptomycin (75 µl of sterile solution or 75 µl of sterile water [control]). Afterwards, animals were supplied with water and food ad libitum. Twenty hours after streptomycin treatment, water and food were withdrawn again for 4 hours before the mice were infected with $1\times10^7$ CFU of *S. Typhimurium* (50-µl suspension in HBSS) or treated with sterile HBSS (control) by oral gavage as previously described (McCormick et al., "*Salmonella typhimurium* Attachment to Human Intestinal Epithelial Monolayers: Transcellular Signalling to Subepithelial Neutrophils," *J Cell Biol* 123:895-907 (1993), which is hereby incorporated by reference in its entirety). At 6, 18, and 24 hours after infection, mice were sacrificed and tissue samples from the intestinal tracts were removed for analysis.

Immunoblotting:

Mouse epithelial cells were scraped and lysed in lysis buffer (1% Triton X-100, 150 mM NaCl, 10 mM Tris pH 7.4, 1 mM EDTA, 1 mM EGTA pH 8.0, 0.2 mM sodium orthovanadate, protease inhibitor cocktail) and protein concentration measured. T84 or HT29-CL19A Cells were colonized with equal numbers of the indicated bacteria for 30 minutes, washed with HBSS, and incubated in DMEM containing gentamicin (500 µg/ml) for the times indicated. Cells were lysed in protein loading buffer (50 mM Tris, pH 6.8, 100 mM dithiothreitol, 2% SDS, 0.1% bromphenol blue, 10% glycerol). Equal volumes of total cell lysate were separated by SDS-PAGE, transferred to nitrocellulose, and processed for immunoblotting with Mouse anti-α-catenin, Rabbit anti-claudin-1, Mouse anti-occludin-1, Mouse anti-ZO-1 antibodies from Zymed Laboratories Inc. (South San Francisco, Calif.), or E-cadherin antibodies from BD Transduction Laboratories (Franklin Lakes, N.J.).

Immunoblotting for AvrA:

Bacteria were lysed in lysis buffer [in mM: 50 Tris, pH 8.0, 150 NaCl, 5 EDTA with a complete Mini protease inhibitor cocktail (1 tablet/10 ml, Roche), and 1% Triton X-100], and sonicated. Equal amounts of total proteins were loaded, separated by SDS-PAGE, and processed for immunoblotting with custom-made AvrA antibody. The 15 amino acid (aa) peptide CGEEPFLPSDKADRY corresponds to residues 216-230 of SEQ ID NO: 1.

AvrA Transfection:

HT29CL19A cells were grown in 12-well plates. At 70-80% confluence, cells were transfected with a pCMV-myc-AvrA wild-type gene construct, a pCMV-myc-AvrAC186A AvrA mutant construct, or control empty pCMV-myc plasmid using LipofectAMINE (Invitrogen). The AvrA mutant C186A is a single amino acid residue transition which is mutated at the key cysteine required for AvrA's activity as previously described (Collier-Hyams et al., "Cutting Edge: *Salmonella* AvrA Effector Inhibits the Key Proinflammatory, Anti-apoptotic NF-kappa B Pathway," *J Immunol* 169:2846-2850 (2002); Ye et al., "*Salmonella* effector AvrA Regulation of Colonic Epithelial Cell Inflammation by Deubiquitination," *Am J Pathol* 171:882-892 (2007), each of which is hereby incorporated by reference in its entirety). 24 h after transfection, cells were lysed in protein loading buffer (50 mM Tris, pH 6.8, 100 mM dithiothreitol, 2% SDS, 0.1% bromophenol blue, 10% glycerol). Equal volumes of total cell lysate were separated by SDS-PAGE, transferred to nitrocellulose, and processed for immunoblotting.

Immunofluorescence Staining:

Cultured epithelial cells T84 or HT29-CL19A were incubated with equal numbers of the indicated bacteria for 30 minutes and washed with HBSS. Immunofluorescent labeling of cells grown on inserts was performed as follows: cells were fixed for 30 minutes in 1% paraformaldehyde in PBS and then washed in PBS. Fixed samples were incubated in blocking solution (5% bovine serum albumin, 0.1% saponin, 1 mM calcium in PBS) for 20 minutes, followed by a 90 minute incubation with primary antibodies diluted in blocking solution (1% bovine serum albumin, 0.1% saponin, 1 mM calcium in PBS): 1:100 Rabbit anti-Claudin-1 (Zymed Laboratories Inc., South San Francisco, Calif.); 1:1000 Mouse anti-ZO-1 (Zymed Laboratories Inc., San Francisco, Calif.). After a 60 minute incubation with secondary antibodies: 1:200 Alexa Fluor 488 goat-anti-rabbit IgG H+L; 1:200 Alexa Fluor 594 goat-anti-mouse IgG H+L; 1:10,000 4',6-diamidino-2-phenyl-indole, dihydrochoride (DAPI) (all from Molecular Probes, Eugene, Oreg.), the inserts were mounted with SlowFade (SlowFade® AntiFade Kit, Molecular Probes) followed by a coverslip, and the edges were sealed to prevent drying. Specimens were examined with a Leica SP2 A OBS Laser Scanning confocal microscope.

Colonic tissues from the proximal and distal portion of the colon were freshly isolated and embedded in paraffin wax after fixation with 10% neutral buffered formalin. After preparation of the slides as described above, slides were incubated in 3% $H_2O_2$ for 20 minutes at room temperature to block endogenous peroxidase activity, followed by incubation for 20 min in 5% BSA with 0.1% saponin in PBS to reduce nonspecific background. The samples were incubated with primary antibodies as indicated for 90 minutes at room temperature. Samples were then incubated with goat anti-rabbit Alexa Fluor 488 (Molecular Probes, Invitrogen Detection Technologies, Eugene, Oreg., USA; 1:200), goat anti-mouse Alexa Fluor 594 (Molecular Probes, CA, USA; 1:200), and DAPI (Molecular Probes 1:10 000) for 1 h at room temperature. Tissues were mounted with SlowFade. Specimens were examined with a Leica SP2 A OBS Laser Scanning confocal microscope.

TER Measurement:

Cells were grown as monolayers on collagen-coated polycarbonate membrane Transwell supports (Corning-Costar, Acton, Mass.). Cells were colonized with equal numbers of the indicated bacteria for 30 minutes, washed with HBSS, and incubated in DMEM containing gentamicin (500 µg/ml, Invitrogen Corporation) for the time indicated. Transepithelial resistance (TER) was measured with an epithelial voltohmmeter (EVOM, World Precision Instruments, Sarasota, Fla.). Each measurement was performed in triplicate.

Fluorescence Permeability In Vivo:

Streptomycin pre-treated mice were infected with different bacterial strains for 24 hours. Fluorescein Dextran (Molecular weight 3000 Da, diluted in HBSS) was gavaged (50 mg/g mouse). Four hours later, mouse blood samples were collected by cardiac puncture. Fluorescence intensity of the plasma was measured on a fluorescent plate reader (Caplan et al., "Bifidobacterial Supplementation Reduces the Incidence of Necrotizing Enterocolitis in a Neonatal Rat Model," *Gastroenterology* 117:577-583 (1999), which is hereby incorporated by reference in its entirety).

Statistical Analysis:

Data are expressed as mean±SD. Differences between two samples were analyzed by Student's t test. P-values of 0.05 or less were considered significant.

Example 1

Figure 3A:
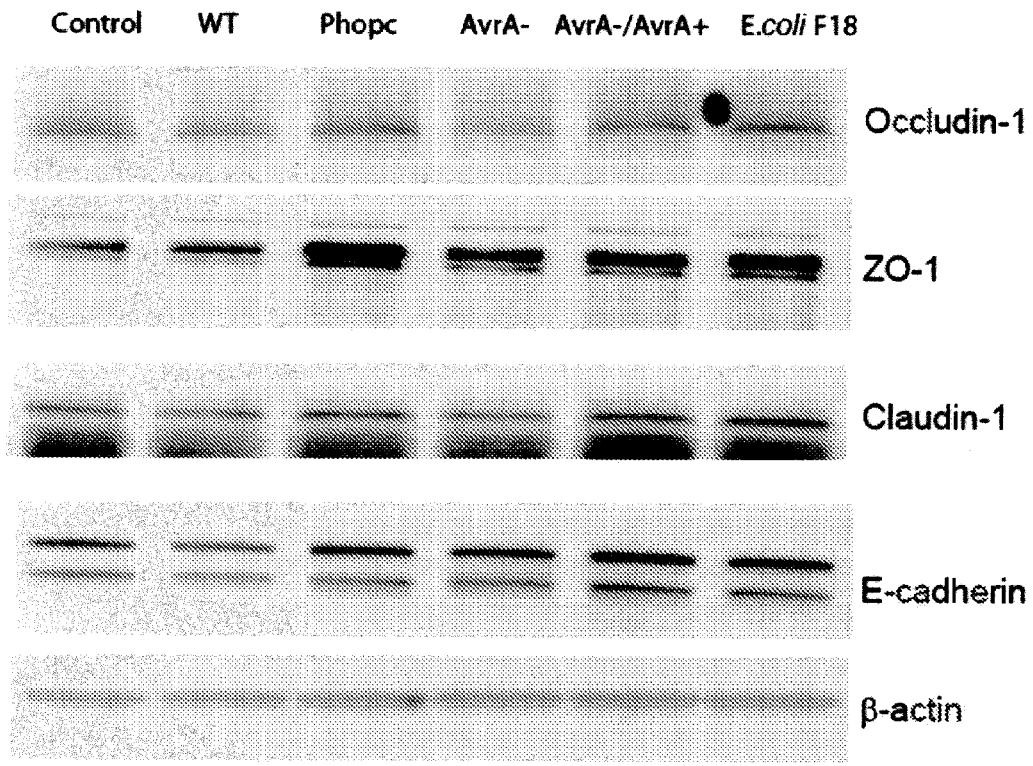
FIGS. 3A-B illustrate that AvrA expression stabilizes the protein expressions of occludin and ZO-1 in vitro.
Figure 3B:
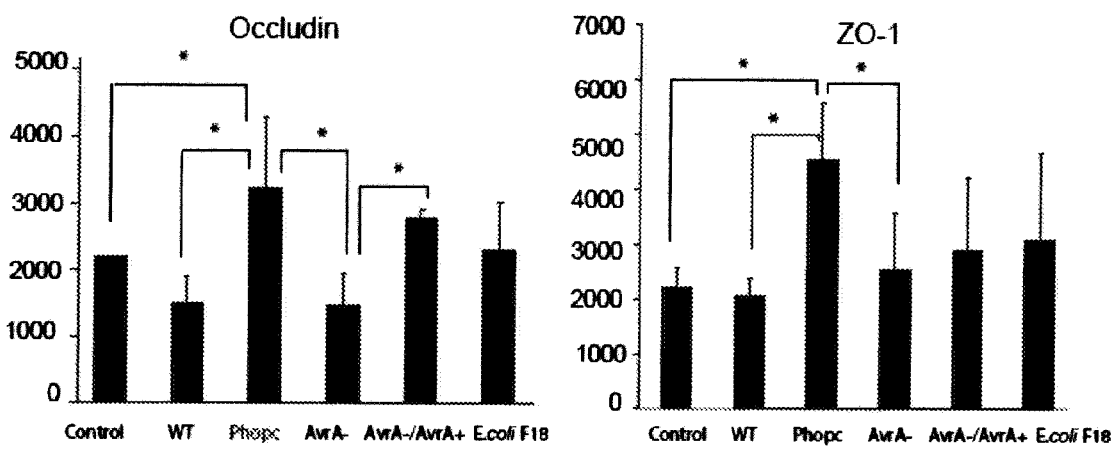

AvrA Expression Alters Tight Junction Protein Expression in Human Epithelial Cells The analysis first assessed whether infection of T84 cell monolayers with AvrA protein-sufficient or -deficient bacterial strains could influence the expression of the major proteins, which comprise the tight junction complex. The expression of tight junction proteins claudin-1, occludin-1, and Zonula occludens-1 (ZO-1) was assessed by Western blot. The adhesion protein E-cadherin was also assessed. After bacterial colonization in epithelial cells for only one hour, both the wild-type *S. Typhimurium* 14028s (with insufficient AvrA expression) and the PhoP$^c$ AvrA mutant strain lacking the AvrA gene (PhoP$^c$ AvrA−) led to a down-regulation of the TJ proteins ZO-1, occludin, and claudin-1 (FIG. 3A). In contrast, the parental PhoP$^c$ with sufficient AvrA expression stabilized TJ protein expression. *E. coli* F18 failed to modulate the expression of occludin-1 and claudin-1, which is consistent with the report by Köhler et al. ("*Salmonella enterica* serovar *Typhimurium* Regulates Intercellular Junction Proteins and Facilitates Transepithelial Neutrophil and Bacterial Passage," *Am J Physiol Gastrointest Liver Physiol* 293:G178-187 (2007), which is hereby incorporated by reference in its entirety). In FIG. 3B, the immunoblot intensity analysis demonstrated that occludin and ZO-1 expression was significantly increased by the presence of PhoP$^c$ with AvrA protein expression, whereas the AvrA-deficient strain (AvrA−) and wild-type *Salmonella* 14028s with insufficient AvrA protein induced a significantly less in ZO-1 and occludin expression. AvrA expression also stabilized TJ proteins in HT-29CL19A monolayers.

Example 2

Figure 4A:
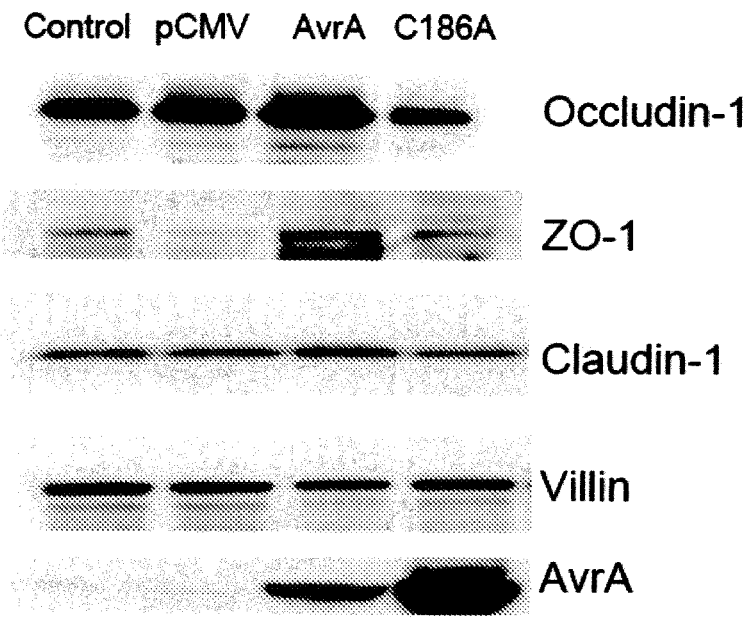
FIGS. 4A-B illustrate that AvrA transfection in epithelial cells increases TJ protein expression.
Figure 4B:
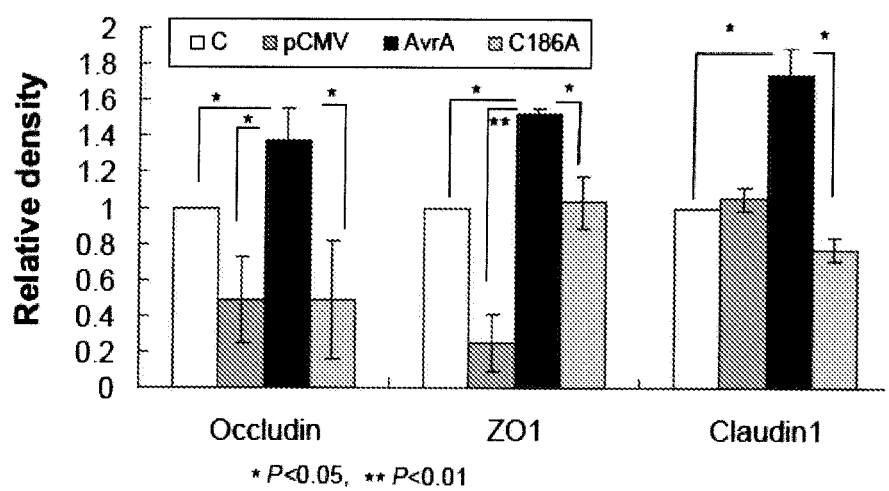

AvrA Overexpression in Epithelial Cells Increases Tight Junction Protein Expression To determine whether AvrA expression directly regulates TJ protein, human colonic epithelial HT29CL19A cells were transfected with a pCMV-myc-AvrA wild-type gene construct, a pCMV-myc-AvrAC186A AvrA mutant construct, or a control pCMV-myc plasmid. The AvrA mutant C186A is a single amino acid residue transition which is mutated at the key cysteine required for AvrA activity as previously described (Collier-Hyams et al., "Cutting Edge: *Salmonella* AvrA Effector Inhibits the Key Proinflammatory, Anti-apoptotic NF-kappa B Pathway," *J Immunol* 169:2846-2850 (2002); Ye et al., "*Salmonella* effector AvrA Regulation of Colonic Epithelial Cell Inflammation by Deubiquitination," *Am J Pathol* 171:882-892 (2007), each of which is hereby incorporated by reference in its entirety). As shown in FIG. 4, AvrA overexpression in colonic epithelial cells increased ZO-1, claudin-1, and occludin-1 expression significantly, whereas the AvrA mutant C186A was able to reverse the effect and decrease the TJ protein expression to the levels comparable to those in the cells transfected with empty pCMV-myc vector. These data indicate that AvrA expression directly increases TJ protein expression. The cysteine site required for the AvrA activity is involved in AvrA regulation of TJ protein expression.

Example 3

AvrA Expression Alters Tight Junction Protein Distribution in vitro

Tight junction protein distribution was further examined. Epithelial cells colonized with AvrA-sufficient or -deficient strains were analyzed for the location of claudin-1 and ZO-1.

Figure 5:
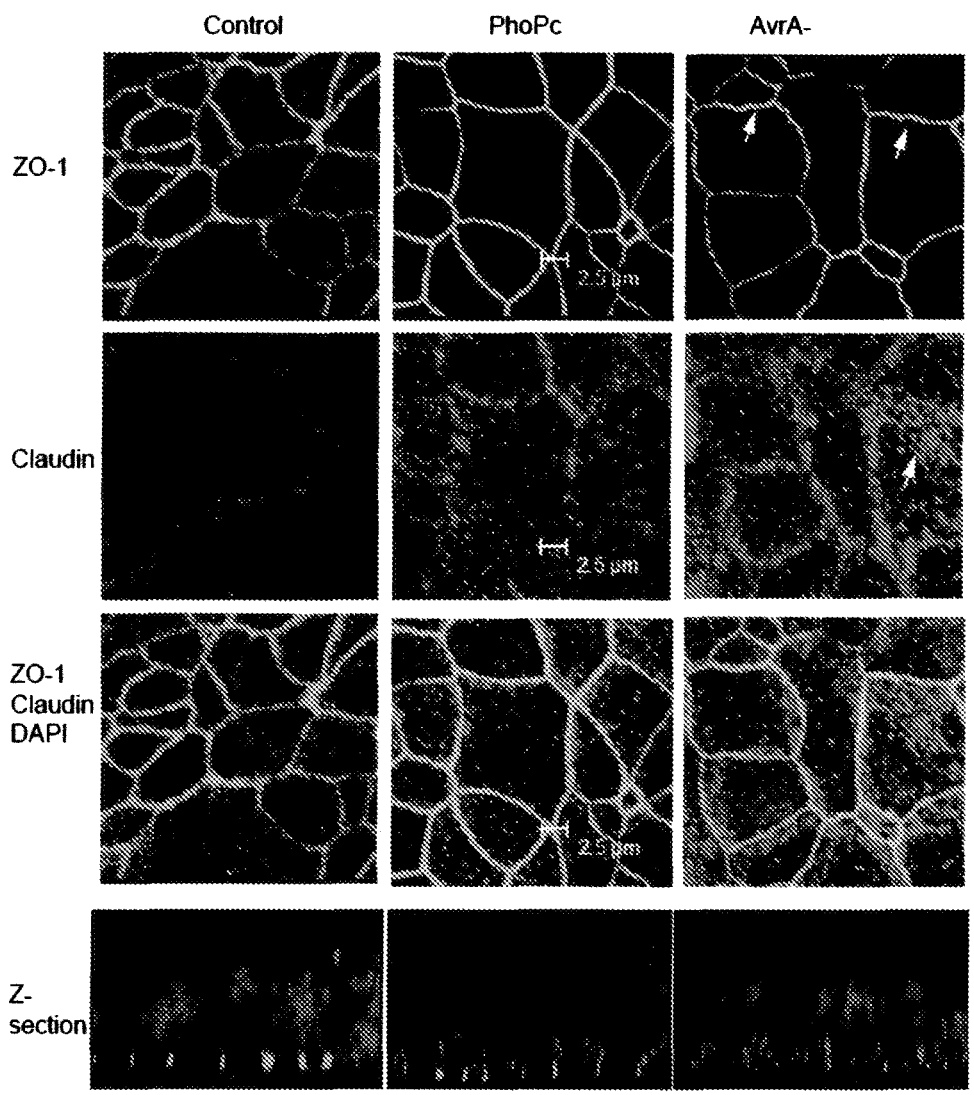
FIG. 5 illustrates the immunostaining of claudin-1 and ZO-1 in cells colonized with AvrA-sufficient or -deficient bacteria in vitro. T84 monolayers were treated with PhoPc or AvrA–. After 8 hours, the monolayers were fixed and immunostained for claudin-1 and ZO-1. ZO-1 distribution in the control cells without any treatment has its normally smooth nature. In PhoP$^c$-treated cells, the distribution of ZO-1 was very similar to that in the control cells. ZO-1's appearance in PhoP$^c$ group was similar as the control group when cells were viewed in cross-Z-section (Z-section for Control and PhoP$^c$). However, in cells treated with *Salmonella* derivative AvrA– mutant (without AvrA), the normally smooth arc-like ZO-1 profiles were transformed into a complex series of irregular undulations (first row of panels AvrA–). ZO-1 staining became thinner and more sinuous. The Z-section panel in FIG. 5 shows the weak staining of ZO-1 in AvrA–. AvrA absence induced a disorganization of transmembrane protein claudin-1, and the protein was moreover expanded intracellularly (second row, see arrow). PhoP$^C$ treatment also slightly changed the distribution of claudin-1. Intracellular claudin-1 was detectable in the cytosol of the cells colonized with PhoP$^c$. Results are representative of five independent experiments.

ZO-1: ZO-1 is a cytoplasmic plaque tight junction protein. In control monolayers without any treatment, ZO-1 was restricted to cellular borders and distributed in a smooth arc-like pattern. In PhoP$^c$ treated cells, the distribution of ZO-1 was very similar to that in the control cells. The appearance of ZO-1 in the PhoP$^c$ group was similar to the control group when cells were viewed in cross-Z-section (FIG. 5, Z-section for Control and PhoP$^c$). However, in cells treated with *Salmonella* derivative AvrA− mutant (without AvrA), the normally smooth arc-like ZO-1 profiles were transformed into a complex series of irregular undulations (FIG. 5, first row of panels AvrA−). Further, ZO-1 staining became thinner and more sinuous. The Z-section panel in FIG. 5 shows the weak staining of ZO-1 in AvrA−.

Claudin-1: Claudin-1 is highly enriched at sites of cell-cell contact, co-localizing with the TJ marker, ZO-1 (Anderson et al., "Setting up a Selective Barrier at the Apical Junction Complex," *Curr Opin Cell Biol* 16:140-145 (2000), which is hereby incorporated by reference in its entirety). AvrA absence induced a disorganization of transmembrane protein claudin-1, and the protein was expanded intracellularly (FIG. 5, second row, at arrow). Interestingly, PhoP$^C$ treatment also slightly changed the distribution of claudin-1. Intracellular claudin-1 was detectable in the cytosol of the cells colonized with PhoP$^c$. This indicated that additional bacterial proteins may be involved in regulating TJs. Overall, the immunofluorescence data suggest that AvrA modulates junctional localization of ZO-1 and claudin-1 proteins.

Example 4

Transepithelial Resistance and AvrA

Transepithelial resistance (TER) is a measure of intestinal epithelial integrity and tissue viability (Turner et al., "Transepithelial Resistance can be Regulated by the Intestinal Brush-Border Na$^{(+)}$/H$^{(+)}$ Exchanger NHE3," *Am J Physiol Cell Physiol* 279:C1918-1924 (2000); Turner et al., "Physiological Regulation of Epithelial Tight Junctions Is Associated with Myosin Light-chain Phosphorylation," *Am J Physiol* 273:C1378-1385 (1997), each of which is hereby incorporated by reference in its entirety). The TER of the epithelial cells was assessed before and after bacterial colonization. Cells were colonized with AvrA-sufficient or -deficient bacterial strains for 30 minutes and then washed. TER of monolayers was measured after switching to fresh media containing gentamicin to prevent further bacterial growth. The data showed that the baseline TER ($\Omega cm^2$) at 0 minute in controls without treatment was 987.1±6.8 $\Omega cm^2$. The TER values for cultured epithelial cells from the control group remained relatively stable over the 30 to 90 minute incubation period. There was a decrease of TER (482.1±5.3 $\Omega cm^2$) after AvrA– colonization for 30 minutes, whereas parental PhoP$^c$, a derivative of wild-type Salmonella SL14028s, did not change TER significantly. It is consistent with previous study that SL14028s did not have effect on the TER of T84 cells (McCormick et al., "*Salmonella typhimurium* Attachment to Human Intestinal Epithelial Monolayers: Transcellular Signalling to Subepithelial Neutrophils," *J Cell Biol* 123:895-907 (1993), each of which is hereby incorporated by reference in its entirety). In this study, the TER change was focus in the initial 6 hours. Overall, cells colonized with the AvrA-deficient bacterial strain (AvrA–) had the lowest TER compared to the control, PhoP$^c$, and PhoPc AvrA+/AvrA– groups, but there was no significant difference among the groups.

Example 5

AvrA Expression and Permeability in vivo

Figure 6:
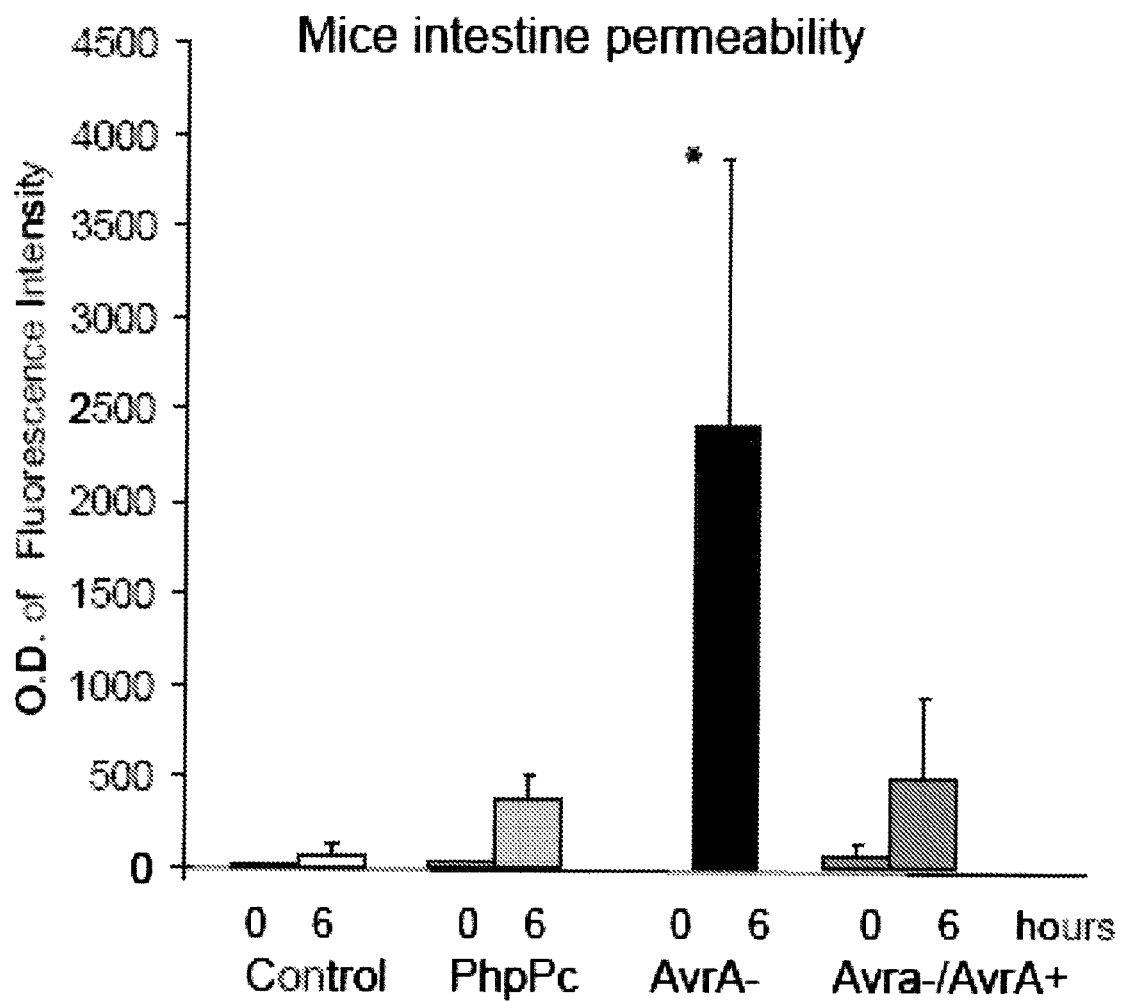
FIG. 6 is a graph illustrating AvrA regulated permeability in the human colonic epithelial cells in vivo. Data are representative of three experiments. P<0.05 for control vs. AvrA–, PhoP$^C$ vs. AvrA–, and AvrA– vs. AvrA–/+ after infection for 28 hours.

To assess the biological relevance of AvrA expression in vivo, a streptomycin-pretreatment mouse model was utilized (Barthel et al., "Pretreatment of Mice with Streptomycin Provides a *Salmonella enterica* serovar *Typhimurium* Colitis Model that Allows Analysis of Both Pathogen and Host," *Infect Immun* 71:2839-2858 (2003), which is hereby incorporated by reference in its entirety), and the mice were gavaged with parental PhoP$^c$, AvrA–, or PhoP$^c$ AvrA–/AvrA+ strains. Immunofluorescence-tagged FITC-dextran was also gavaged in each mouse for the permeability assay (FIG. 6). Mouse serum was collected to measure the intensity of fluorescence. Higher FITC readings indicate higher permeability of the intestine. There was a 5-fold increase of the fluorescence reading in the AvrA– infected mouse serum compared to that in the PhoP$^c$ mouse serum. In the PhoP$^c$ AvrA–/AvrA+ group, complemented AvrA expression was able to significantly decrease cell permeability. The data demonstrated that AvrA-sufficient bacteria significantly decrease the intestinal permeability compared to AvrA-deficient bacteria. It indicates the physiological function of AvrA in preserving intestinal epithelial cell integrity in vivo.

Example 6

Figure 7:
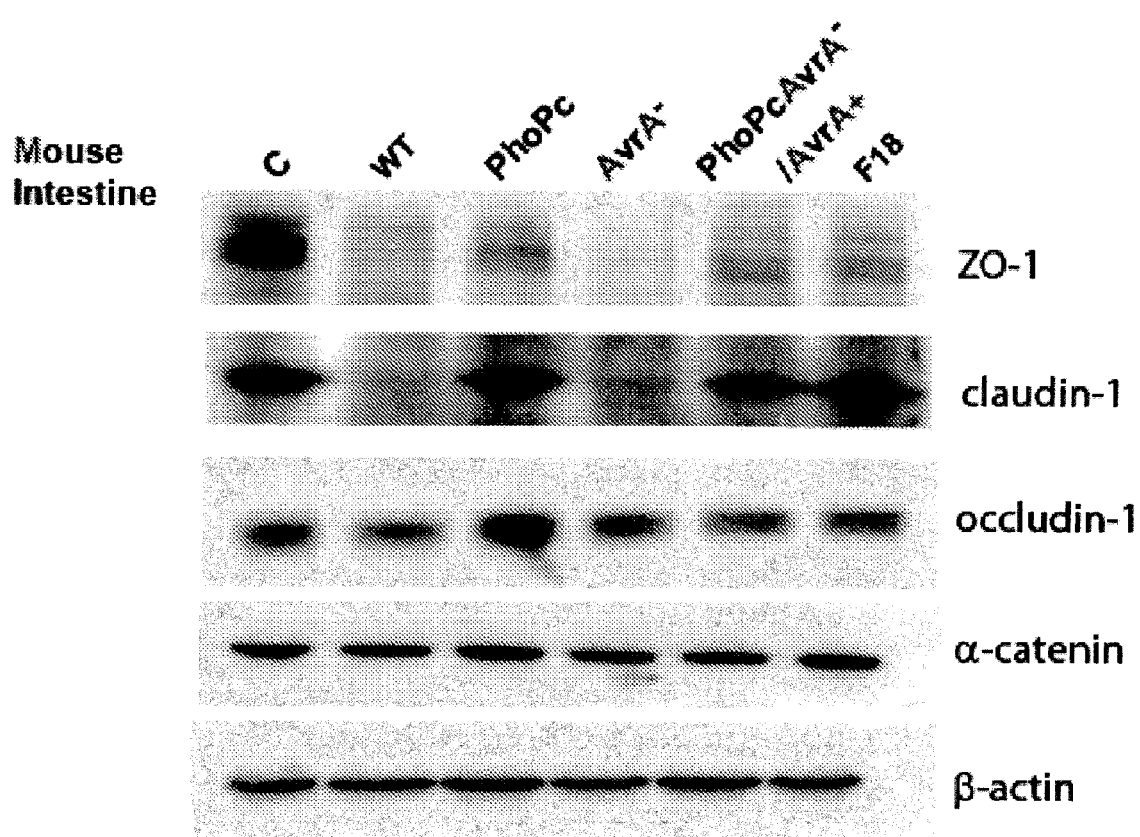
FIG. 7 illustrates the *Salmonella* AvrA protein modulated ZO-1, occludin, and claudin-1 expression in vivo. Mice were infected with bacteria for 18 hrs and intestinal epithelial cells were harvested for ZO-1, claudin-1, occludin, and α-catenin expression by immunoblot. Experimental groups: C: normal mouse cells; WT: wild-type *S. Typhimurium* ATCC 14028s without sufficient AvrA protein expression; PhoP$^c$: parental PhoP$^c$ with sufficient AvrA protein expression; AvrA$^-$: PhoP$^c$ AvrA mutant; PhoP$^c$ AvrA$^-$/AvrA$^+$: PhoP$^c$ AvrA– transcomplemented with a plasmid encoding WT AvrA; or *E. coli* F18: commensal bacteria isolated from human intestine. Images shown are from a single experiment and are representative of three separate experiments.

AvrA Expression Stabilizes the Expression of Tight Junction Proteins in vivo Epithelial cells from mouse colon were collected, and TJ protein expression was quantitated (FIG. 7). As expected, wild-type *Salmonella* 14028s colonization decreased the total amount ZO-1, claudin-1, and occludin-1 protein expression. AvrA– decreased ZO-1, claudin-1, and occludin-1 expression, whereas total occludin-1 expression was increased by the parental PhoP$^c$ strain with AvrA expression. Interestingly, the claudin-1 expression was stabilized but not increased by the PhoP$^c$ colonization. In the PhoP$^c$ AvrA–/AvrA+ group with complemented AvrA, the expression of ZO-1, claudin-1, and occludin-1 was stabilized to levels comparable to those in the samples from the parental PhoP$^c$-treated group. Compared to the normal mice without bacterial infection, all the bacterial infected colonic epithelial cells had decrease ZO-1 expression. In a cell cultured model, *E. coli* F18 infection failed to change the expression of TJ proteins (FIG. 3). However, *E. coli* F18 infection in vivo decreased ZO-1 expression. This suggests that other bacterial proteins are involved in the regulation of ZO-1 expression in vivo. Interestingly, wild-type *Salmonella* and *E. coli* F18 infection did not change the expression of α-catenin in vivo. AvrA has no effect on the expression of α-catenin.

Example 7

AvrA Expression Changes Distribution of Tight Junction Proteins in vivo

Immunostaining of ZO-1 and claudin-1 in the experimental animal models further showed that parental PhoP$^c$ with AvrA expression maintained TJ structure in the epithelial cells.

ZO-1: ZO1 was detected at the tight junction of villous enterocytes in both normal control and PhoP$^c$-treated animals. Intracellular ZO-1 deposits were not detected after PhoP$^c$ infection. Under low magnitude observation in FIG. 8, it was observed that the AvrA-deficient mutant disrupted the TJ structure, whereas parental PhoP$^c$ with AvrA protein expression stabilized the TJ structure. Arrows in FIG. 8 ZO-1 show the staining of ZO-1 protein on the top of the intestinal crypts. Please note the disorganized structure of ZO-1 in the colonic epithelial cells infected with the AvrA– bacterial strain. Under high magnification observation in FIG. 9: the ring like structure of ZO-1 was disrupted in mouse colon infected by the AvrA-deficient bacteria.

Claudin-1: The staining of green claudin-1 is weaker in the AvrA– treated intestinal epithelium. Intracellular claudin-1 deposits were not detected after PhoP$^c$ or AvrA– infection. These in vivo data combined with in vitro data (FIG. 5) indicate that additional bacterial proteins may be involved in regulating the distribution of the TJ proteins. Overall, the immunofluorescent data suggested that AvrA modulates junctional localization of ZO-1 and claudin-1 proteins.

Figure 8:
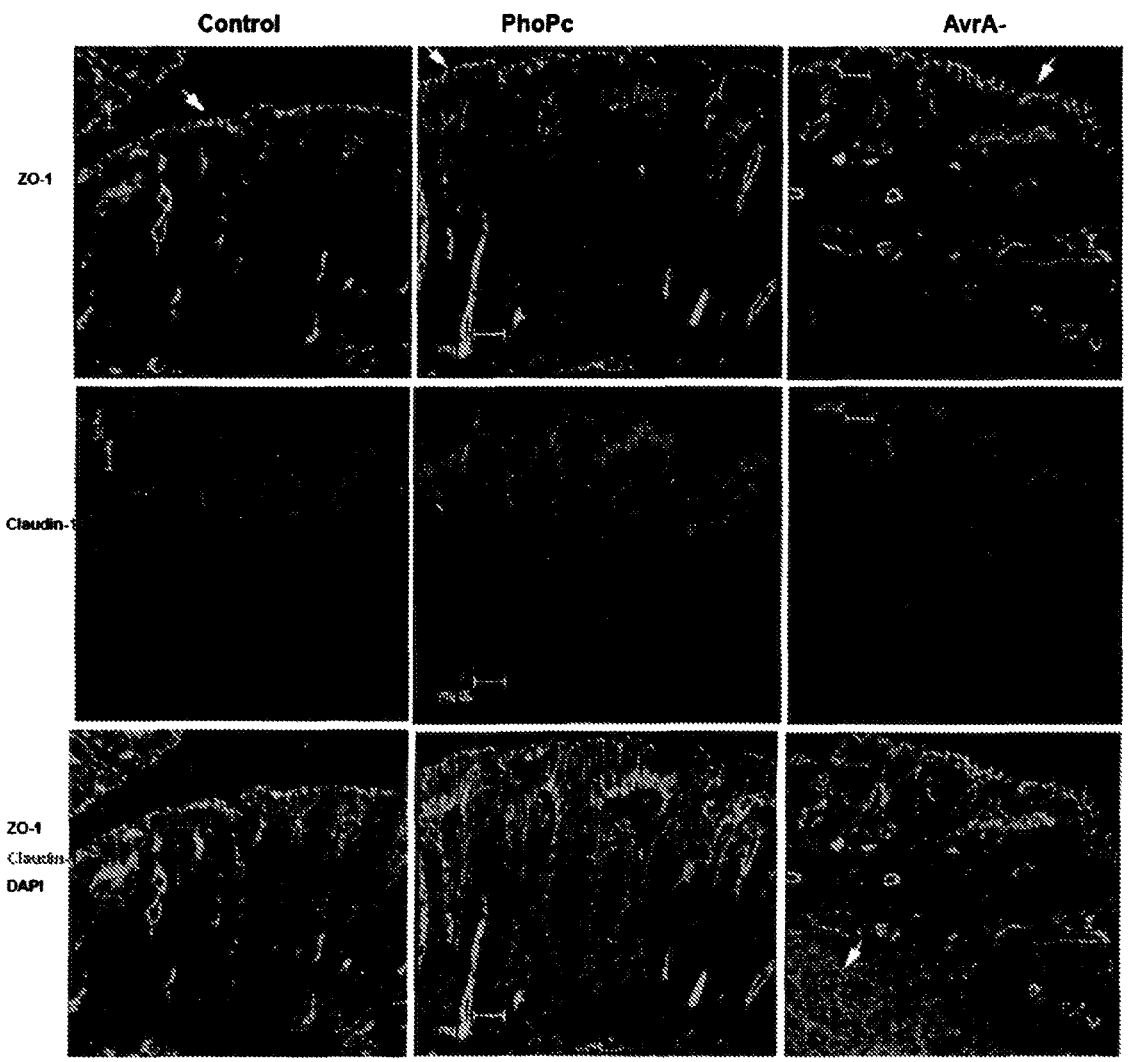
FIG. 8 illustrates the immunostaining of claudin-1 and ZO-1 in vivo. Immunostaining on mouse colonic epithelial cells was performed 24 hours after mouse infection with PhoP$^c$, AvrA$^-$ or AvrA$^-$/AvrA$^+$. Experimental groups: Control: normal mouse cells; PhoP$^c$: mice infected with parental PhoP$^c$ with sufficient AvrA protein expression; AvrA$^-$: mice infected with PhoP$^c$ AvrA mutant. Tissues were fixed, permeabilized, and stained with claudin-1 and ZO-1 antibodies, followed by A488 secondary antibodies, A594 secondary antibodies, and DAPI. AvrA$^-$ infected mice display disruption of the TJ structure. Arrows in Panel ZO-1 show the staining of ZO-1 protein on the top of the intestinal crypts.

Also, in FIG. 8, AvrA– with ZO-1, Claudin-1 overlapped DAPI staining; there was increased inflammation in the epithelial cells as measured by lymphoid aggregation, whereas the tight junction structure was disrupted. The H & E staining indicated that AvrA absence in the bacterial strain (AvrA–) increased the inflammation score in the infected intestine. In the mice infected with parental PhoP$^c$, the tight junction structure was still well organized, and there was less inflammation in the intestine.

Example 8

AvrA Protein Expression Attenuates IL-6 Secretion

It is known that cells colonized with AvrA-sufficient bacteria lack inflammatory response (Ye et al., "*Salmonella* effector AvrA Regulation of Colonic Epithelial Cell Inflammation by Deubiquitination," *Am J Pathol* 171:882-892 (2007), which is hereby incorporated by reference in its entirety). AvrA may stabilize TJ structure by dampening the inflammatory response. To assess the biological relevance of AvrA expression in vivo, mice were infected with WT *Salmonella Typhimurium* strain 14028s (WT) having insufficient AvrA expression or WT 14028s having AvrA overexpression (WTAvrA+). As shown in FIG. 10A, AvrA protein expression is undetectable in WT *Salmonella* 14028s, whereas WTAvrA+ showed a significant increase in AvrA expression. The inflammatory cytokine IL-6 was measured in mouse serum after bacterial infection. WT *Salmonella* induced significantly more IL-6 secretion as measured in infected mouse serum than did the WTAvrA+ (FIG. 10B). In mice infected with the WTAvrA+, AvrA overexpression was able to lower IL-6 serum levels. It is suggested that AvrA expression in the WT *Salmonella* is able to decrease the expression of inflammatory cytokine IL-6.

Discussion of Examples 1-8

The above data demonstrate that the bacterial effector protein AvrA stabilizes the expression and distribution of tight junction proteins such as ZO-1, and the function of tight junctions in vitro and in vivo. AvrA overexpression in transfected colonic epithelial cells increases TJ protein expression. Bacterial strains with AvrA stabilize host cell permeability, cell adhesion, and tight junction and inhibit the inflammatory response. In contrast, AvrA-deficient strains induce morphological and biochemical changes, including increased cell permeability, disrupted TJ structure, and inflammatory responses.

An intriguing aspect of this study is the finding that AvrA stabilized the TJs, whereas the other TTSS proteins, SopB, SopE, SopE2, and SpiA, are known to disrupt the TJs (Boyle et al., "*Salmonella enterica* serovar *Typhimurium* Effectors SopB, SopE, SopE2 and SipA Disrupt Tight Junction Structure and Function," *Cell Microbiol* 8:1946-1957 (2006), which is hereby incorporated by reference in its entirety). Although initially this observation appears unusual, it may represent a highly refined bacterial strategy to overcome many effective host defense mechanisms. Previous studies have demonstrated that AvrA does not stimulate fluid secretion into infected calf ileal loops, whereas SopB and SopD elevate fluid accumulation in bovine intestine (Zhang et al., "The *Salmonella enterica* serotype *typhimurium* Effector Proteins SipA, SopA, SopB, SopD, and SopE2 Act in Concert to Induce Diarrhea in Calves," *Infect Immun* 70:3843-3855 (2002), which is hereby incorporated by reference in its entirety). Current studies show that lack of AvrA increases the cell permeability and disrupted TJ structure, whereas AvrA expression is able to maintain the TJ structure and function and limit the cell permeability. The data on AvrA stabilization of TJ structure and permeability suggest a different role for AvrA distinct from the role of other *Salmonella* effectors in regulating fluid accumulation in intestine.

*Salmonella* effectors, such as SopB, SopE, SopE2, are known to activate the proinflammatory response by directly stimulating proinflammatory signaling events in host cells (Steele-Mortimer et al., "Activation of Akt/protein Kinase B in Epithelial Cells by the *Salmonella typhimurium* Effector sigD," *J Biol Chem* 275:37718-37724 (2000); Friebel et al., "SopE and SopE2 from *Salmonella typhimurium* Activate Different Sets of Rho GTPases of the Host Cell." *J Biol Chem* 276:34035-34040 (2001); Zhang et al., "Molecular Pathogenesis of *Salmonella enterica* serotype *typhimurium*-Induced Diarrhea," *Infect Immun* 71:1-12 (2003); Huang et al., "Cooperative Interactions Between Flagellin and SopE2 in the Epithelial Interleukin-8 Response to *Salmonella enterica* serovar *typhimurium* Infection," *Infect Immun* 72:5052-5062 (2004), each of which is hereby incorporated by reference in its entirety). In contrast, AvrA is able to attenuate the key proinflammatory NF-κB transcription factor (Collier-Hyams et al., "Cutting Edge: *Salmonella* AvrA Effector Inhibits the Key Proinflammatory, Anti-apoptotic NF-kappa B Pathway," *J Immunol* 169:2846-2850 (2002); Ye et al., "*Salmonella* effector AvrA Regulation of Colonic Epithelial Cell Inflammation by Deubiquitination," *Am J Pathol* 171:882-892 (2007), each of which is hereby incorporated by reference in its entirety), activate the β-catenin transcription factor (Sun et al., "Bacterial Activation of Beta-catenin Signaling in Human Epithelia," *Am J Physiol Gastrointest Liver Physiol* 287: G220-227 (2004); Duan et al., "Beta-Catenin Activity Negatively Regulates Bacteria-induced Inflammation," *Lab Invest* 87:613-624 (2007), each of which is hereby incorporated by reference in its entirety), and inhibit cell apoptosis in mouse epithelial cells (Ye et al., "*Salmonella* effector AvrA Regulation of Colonic Epithelial Cell Inflammation by Deubiquitination," *Am J Pathol* 171:882-892 (2007), which is hereby incorporated by reference in its entirety). Therefore, AvrA may function as an anti-inflammatory protein to stabilize TJs, prevent cell death, and help the bacteria survive in the host; whereas the other bacterial effectors do the opposite.

The PhoP$^c$ strain is a derivative of wild-type *Salmonella Typhimurium* SL14028. Previous studies indicated that infection with wild type SL14028 did not influence TER (McCormick et al., "*Salmonella typhimurium* Attachment to Human Intestinal Epithelial Monolayers: Transcellular Signalling to Subepithelial Neutrophils," *J Cell Biol* 123:895-907 (1993), which is hereby incorporated by reference in its entirety), whereas recent studies using the SL1344 showed different results (Boyle et al., "*Salmonella enterica* serovar *Typhimurium* Effectors SopB, SopE, SopE2 and SipA Disrupt Tight Junction Structure and Function," *Cell Microbiol* 8:1946-1957 (2006); Kohler et al., "*Salmonella enterica* serovar *Typhimurium* Regulates Intercellular Junction Proteins and Facilitates Transepithelial Neutrophil and Bacterial Passage," *Am J Physiol Gastrointest Liver Physiol* 293:G178-187 (2007), each of which is hereby incorporated by reference in its entirety). Several factors explain these differences. First, the *S. Typhimurium* background of these strains is different. Since the SL1344 strain induces a more robust response in the ability to induce PMN transepithelial migration than the 14028 strain, and this differences in the virulence phenotype could explain, in part, differences at the level of the TER (Kohler et al., "*Salmonella enterica* serovar *Typhimurium* Regulates Intercellular Junction Proteins and Facilitates Transepithelial Neutrophil and Bacterial Passage," *Am J Physiol Gastrointest Liver Physiol* 293:G178-187 (2007), which is hereby incorporated by reference in its entirety). Second, the level of AvrA expression by a particular *Salmonella* strain may ultimately determine how that organism will behave. Wild type *Salmonella* strains express AvrA conditionally, but at levels insufficient to counteract the actions of other bacterial agents. SL14028 does not have detectable AvrA protein (Steckel et al., "Expression Profiles of Effector Proteins SopB, SopD1, SopE1, and AvrA Differ with Systemic, Enteric, and Epidemic Strains of *Salmonella enterica*," *Mol Nutr Food Res* 48:496-503 (2004); Ben-Barak et al., "The Expression of the Virulence-associated Effector Protein Gene avrA is Dependent on a *Salmonella enterica*-specific Regulatory Function," *Int J Med Microbiol* 296:25-38 (2006), each of which is hereby incorporated by reference in its entirety), whereas the SL1344 sufficiently expresses AvrA protein (Hardt et al., "A Secreted *Salmonella* Protein with Homology to an Avirulence Determinant of Plant Pathogenic Bacteria," *Proc Natl Acad Sci USA* 94:9887-9892 (1997), each of which is hereby incorporated by reference in its entirety). Therefore, the TER was not changed by infection with SL14028, whereas it was changed by infection with SL1344.

Expression of occludin-1, claudin-1, and ZO-1 are altered by AvrA expression using a gene-transfected system, cultured polarized epithelial cells, and a mouse model. Based on these data, AvrA is believed to have a specific role in the expression of ZO-1 and occludin. The key 186 amino acid cysteine is required for AvrA regulation of TJ expression. However, it is not clear whether AvrA regulates these TJ proteins through phosphorylation or through ubiquitination. AvrA acts as a deubiquitinase to inhibit the degradation of the inflammatory regulators IκBα and β-catenin (Ye et al., "*Salmonella* effector AvrA Regulation of Colonic Epithelial Cell Inflammation by Deubiquitination," *Am J Pathol* 171:882-892 (2007), which is hereby incorporated by reference in its entirety). Occludin is a functional target of the E3 ligase Itch (Traweger et al., "The Tight Junction-specific Protein Occludin is a Functional Target of the E3 Ubiquitin-protein Ligase Itch," *J Biol Chem* 277:10201-10208 (2002), which is hereby incorporated by reference in its entirety). Thus, AvrA may stabilize TJ protein by removing ubiquitin from occludin. Rho GTPase is known to be involved in bacteria-induced tight junction disruption (Boyle et al., "*Salmonella enterica* serovar *Typhimurium* Effectors SopB, SopE, SopE2 and SipA Disrupt Tight Junction Structure and Function," *Cell Microbiol* 8:1946-1957 (2006); Zhou et al., "A *Salmonella* Inositol Polyphosphatase Acts in Conjunction with Other Bacterial Effectors to Promote Host Cell Actin Cytoskeleton Rearrangements and Bacterial Internalization," *Mol Microbiol* 39:248-259 (2001); Galan et al., "Striking a Balance: Modulation of the Actin Cytoskeleton by *Salmonella*," *Proc Natl Acad Sci USA* 97:8754-8761 (2000); Soong et al., "The Type III Toxins of *Pseudomonas aeruginosa* Disrupt Epithelial Barrier Function," *J Bacteriol* 190:2814-2821 (2008); Hardt et al., "*S. typhimurium* Encodes an Activator of Rho GTPases that Induces Membrane Ruffling and Nuclear Responses in Host Cells," *Cell* 93:815-826 (1998), each of which is hereby incorporated by reference in its entirety). The data presented herein demonstrates that AvrA is able to stabilize the TJ structure, but it is unclear whether Rho GTPase is influenced by the AvrA expression.

Example 9

Generation of AvrA Point-Mutants and Truncation-Mutants

To explore the molecular mechanism of AvrA-host interaction, a series of AvrA mutants was generated. Based on the sequence alignment of representative AvrA members: the adenovirus-like proteases, YopJ, and AvrBsT (Orth et al., "Disruption of Signaling by *Yersinia* effector YopJ, a Ubiquitin-like Protein Protease," *Science* 290:1594-1597 (2000), which is hereby incorporated by reference in its entirety), the key catalytic amino acids in the AvrA protein are predicted as His$^{123}$, Glu$^{142}$ (or Asp), Cys$^{179}$, as well as Cys$^{186}$ (FIG. 11A). AvrA point-mutations were generated at positions 123, 142, 179, 186 (key amino acid sites), and 180 (non-specific amino acid site) to investigate the relative contributions of these catalytic residues in AvrA function (FIG. 11B).

To make the AvrA C-terminus truncation mutations, a stop codon was added to the AvrA DNA resulting in a premature STOP signal, and therefore generating a shorter AvrA protein (FIGS. 11C-D). The approximate size of the AvrA truncation is illustrated in FIG. 11C. With a myc tag in the mutated proteins, the protein expression could be detected (FIG. 11D). All point-mutant and truncation mutant proteins were properly expressed (FIGS. 11B, 11D), although peptide A6 proved not to be stable.

In addition to the C-terminus truncations, an N-terminal truncation mutant, designated AN, was made by introducing a new start codon into a shorter open reading frame. This peptide is lacking about 38 amino acids from the N-terminus (FIG. 11C).

Example 10

Effect of AvrA Point-Mutants on Tight Junction Proteins

Following transfection of HT29C19A cells with a pCMV-myc-AvrA wild-type gene construct, control empty pCMV-myc plasmid, or the pCMV-myc-AvrA-C186A, -E142A, and -E123A plasmids encoding the point mutants and the pCMV-myc-AvrA-180A control mutant, cells were lysed in protein-loading buffer and immunoblotting was performed for ZO-1, occludin-1, claudin-1, IκBα, c-myc, and β-actin. The results without and with TNFα exposure (30 minutes) are illustrated in FIGS. 12 and 13.

The results demonstrate that expression of full-length AvrA achieved only a slight increase in ZO-1 expression in the absence of TNFα, but achieved a significant increase in ZO-1 expression in the presence of TNFα. These data indicate that AvrA can stabilize the tight junction protein expression especially during the inflammatory stimulation.

Example 11

Effects of Truncated AvrA on Pro-Inflammatory NF-κB Pathway in HCT116 Cell Line

Transfection studies in HCT116 cell line using pCMV-AvrA (full length AvrA) and pA1-6 (truncated AvrA 1-6 fragments) with and without of TNFα demonstrated that only the larger fragments A1 and A2 can produce similar results to full length AvrA with respect to phosphorylated p65 levels (FIG. 14). Shorter fragments A3, A4, A5, and A6 resulted in much higher levels of phosphorylation for p65 (FIG. 14).

Transfection studies in HCT116 cell line showed that full length AvrA and truncation mutant A1 are able to protect IκBα from degradation, whereas truncation mutants A2-A4 lose the ability to protect IκBα from degradation (FIGS. 15 and 16). Fragments A5 and A6 possess no ability to protect IκBα from degradation. The N-terminal truncation, AN, also showed some ability to protect IκBα from degradation.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for treating inflammatory intestinal disease or disorder in a mammalian subject in need thereof, the method comprising: administering to the subject a therapeutically effective dose of an isolated AvrA protein or polypeptide comprising an amino acid sequence that is at least about 90% identical to the full length of SEQ ID NO: 19.

2. The method of claim 1, wherein the inflammatory intestinal disease or disorder is Inflammatory Bowel Disease, Celiac Disease, or gastroenteritis.

3. The method of claim 1, wherein the AvrA protein is a *Salmonella* AvrA protein.

4. The method of claim 1, wherein the AvrA protein or polypeptide is administered at a dose ranging from 0.1 mg to 10 mg of said protein or polypeptide per kg of said subject's body weight.

5. The method of claim 1, wherein said administering is carried out parenterally, orally, topically, intranasally, rectally, or via slow releasing microcarriers.

6. The method of claim 1, wherein the isolated AvrA protein or polypeptide is present in a composition further comprising a stabilizing agent.

7. The method of claim 1, wherein the isolated AvrA protein or polypeptide comprises an amino acid sequence that is at least about 95% identical to the full length of SEQ ID NO: 19.

8. The method of claim 1, wherein the isolated AvrA protein or polypeptide comprises an amino acid sequence that is at least about 97% identical to the full length of SEQ ID NO: 19.

* * * * *

SEQUENCE LISTING

```
<160> NUMBER OF SEQ ID NOS: 19

<210> SEQ ID NO 1
<211> LENGTH: 301
<212> TYPE: PRT
<213> ORGANISM: Salmonella enterica
```

```
<400> SEQUENCE: 1

Met Ile Phe Ser Val Gln Glu Leu Ser Cys Gly Gly Lys Ser Met Leu
1               5                   10                  15

Ser Pro Thr Thr Arg Asn Met Gly Ala Ser Leu Ser Pro Gln Pro Asp
            20                  25                  30

Val Ser Gly Glu Leu Asn Thr Glu Ala Leu Thr Cys Ile Val Glu Arg
        35                  40                  45

Leu Glu Ser Glu Ile Ile Asp Gly Ser Trp Ile His Ile Ser Tyr Glu
    50                  55                  60

Glu Thr Asp Leu Glu Met Met Pro Phe Leu Val Ala Gln Ala Asn Lys
65                  70                  75                  80

Lys Tyr Pro Glu Leu Asn Leu Lys Phe Val Met Ser Val His Glu Leu
                85                  90                  95

Val Ser Ser Ile Lys Glu Thr Arg Met Glu Gly Val Glu Ser Ala Arg
            100                 105                 110

Phe Leu Val Asn Met Gly Ser Ser Gly Ile His Ile Ser Val Val Asp
        115                 120                 125

Phe Arg Val Met Asp Gly Lys Thr Ser Val Ile Leu Phe Glu Pro Ala
    130                 135                 140

Ala Cys Ser Ala Phe Gly Pro Ala Leu Ala Leu Arg Thr Lys Ala Ala
145                 150                 155                 160

Leu Glu Arg Glu Gln Leu Pro Asp Cys Tyr Phe Ala Met Val Glu Leu
                165                 170                 175

Asp Ile Gln Arg Ser Ser Ser Glu Cys Gly Ile Phe Ser Leu Ala Leu
            180                 185                 190

Ala Lys Lys Leu Gln Leu Glu Phe Met Asn Leu Val Lys Ile His Glu
        195                 200                 205

Asp Asn Ile Cys Glu Arg Leu Cys Gly Glu Glu Pro Phe Leu Pro Ser
    210                 215                 220

Asp Lys Ala Asp Arg Tyr Leu Pro Val Ser Phe Tyr Lys His Thr Gln
225                 230                 235                 240

Gly Ala Gln Arg Leu Asn Glu Tyr Val Glu Ala Asn Pro Ala Ala Gly
                245                 250                 255

Ser Ser Ile Val Asn Lys Lys Asn Glu Thr Leu Tyr Glu Arg Phe Asp
            260                 265                 270

Asn Asn Ala Val Met Leu Asn Asp Lys Lys Leu Ser Ile Ser Ala His
        275                 280                 285

Lys Lys Arg Ile Ala Glu Tyr Lys Ser Leu Leu Lys Pro
    290                 295                 300

<210> SEQ ID NO 2
<211> LENGTH: 302
<212> TYPE: PRT
<213> ORGANISM: Salmonella enterica

<400> SEQUENCE: 2

Met Ile Phe Ser Val Gln Glu Leu Ser Cys Gly Gly Lys Ser Met Leu
1               5                   10                  15

Ser Pro Thr Thr Arg Asn Met Gly Ala Ser Leu Ser Pro Gln Pro Asp
            20                  25                  30

Val Ser Gly Glu Leu Asn Thr Glu Ala Leu Thr Cys Ile Val Glu Arg
        35                  40                  45

Leu Glu Ser Glu Ile Ile Asp Gly Ser Trp Ile His Ile Ser Tyr Glu
    50                  55                  60

Glu Thr Asp Leu Glu Met Met Pro Phe Leu Val Ala Gln Ala Asn Lys
```

```
                65                  70                  75                  80
Lys Tyr Pro Glu Leu Asn Leu Lys Phe Val Met Ser Val His Glu Leu
                85                  90                  95
Val Ser Ser Ile Lys Glu Thr Arg Met Glu Gly Val Glu Ser Ala Arg
            100                 105                 110
Phe Leu Val Asn Met Gly Ser Gly Ile His Ile Ser Val Val Asp
            115                 120                 125
Phe Arg Val Met Asp Gly Lys Thr Ser Val Ile Leu Phe Glu Pro Ala
        130                 135                 140
Ala Cys Ser Ala Phe Gly Pro Ala Leu Leu Ala Leu Arg Thr Lys Ala
145                 150                 155                 160
Ala Leu Glu Arg Glu Gln Leu Pro Asp Cys Tyr Phe Ala Met Val Glu
                165                 170                 175
Leu Asp Ile Gln Arg Ser Ser Glu Cys Gly Ile Phe Ser Leu Ala
            180                 185                 190
Leu Ala Lys Lys Leu Gln Leu Glu Phe Met Asn Leu Val Lys Ile His
            195                 200                 205
Glu Asp Asn Ile Cys Glu Arg Leu Cys Gly Glu Glu Pro Phe Leu Pro
210                 215                 220
Ser Asp Lys Ala Asp Arg Tyr Leu Pro Val Ser Phe Tyr Lys His Thr
225                 230                 235                 240
Gln Gly Ala Gln Arg Leu Asn Glu Tyr Val Glu Ala Asn Pro Ala Ala
                245                 250                 255
Gly Ser Ser Ile Val Asn Lys Lys Asn Glu Thr Leu Tyr Glu Arg Phe
            260                 265                 270
Asp Asn Asn Ala Val Met Leu Asn Asp Lys Lys Leu Ser Ile Ser Ala
        275                 280                 285
His Lys Lys Arg Ile Ala Glu Tyr Lys Ser Leu Leu Lys Pro
            290                 295                 300

<210> SEQ ID NO 3
<211> LENGTH: 302
<212> TYPE: PRT
<213> ORGANISM: Salmonella enterica

<400> SEQUENCE: 3

Met Ile Phe Ser Val Gln Glu Leu Ser Cys Gly Gly Lys Ser Met Leu
1               5                   10                  15
Ser Pro Thr Thr Arg Asn Met Gly Ala Ser Leu Ser Pro Gln Pro Asp
            20                  25                  30
Val Ser Gly Glu Leu Asn Thr Glu Ala Leu Thr Cys Ile Val Glu Arg
        35                  40                  45
Leu Glu Ser Glu Ile Ile Asp Gly Ser Trp Ile His Ile Ser Tyr Glu
    50                  55                  60
Glu Thr Asp Leu Glu Met Met Pro Phe Leu Val Ala Gln Ala Asn Lys
65                  70                  75                  80
Lys Tyr Pro Glu Leu Asn Leu Lys Phe Val Met Ser Val His Glu Leu
                85                  90                  95
Val Ser Ser Ile Lys Glu Thr Arg Met Glu Gly Val Glu Ser Ala Arg
            100                 105                 110
Phe Leu Val Asn Met Gly Ser Ser Gly Ile His Ile Ser Val Val Asp
        115                 120                 125
Phe Arg Val Met Asp Gly Lys Thr Ser Val Ile Leu Phe Glu Pro Ala
    130                 135                 140
Ala Cys Ser Ala Phe Gly Pro Ala Leu Leu Ala Leu Arg Thr Lys Ala
```

```
              145                 150                 155                 160
Ala Leu Glu Arg Glu Gln Leu Pro Asp Cys Tyr Phe Ala Met Val Glu
                165                 170                 175

Leu Asp Ile Gln Arg Ser Ser Ser Glu Cys Gly Ile Phe Ser Leu Ala
            180                 185                 190

Leu Ala Lys Lys Leu Gln Leu Glu Phe Met Asn Leu Val Lys Ile His
        195                 200                 205

Glu Asp Asn Ile Cys Glu Arg Leu Cys Gly Glu Pro Phe Leu Pro
    210                 215                 220

Ser Asp Lys Ala Asp Arg Tyr Leu Pro Val Ser Phe Tyr Lys His Thr
225                 230                 235                 240

Gln Gly Val Gln Arg Leu Asn Glu Tyr Val Glu Ala Asn Pro Ala Ala
                245                 250                 255

Gly Ser Ser Ile Val Asn Lys Lys Asn Glu Thr Leu Tyr Glu Arg Phe
                260                 265                 270

Asp Asn Asn Ala Val Met Leu Asn Asp Lys Lys Leu Ser Ile Ser Ala
            275                 280                 285

His Lys Lys Arg Ile Ala Glu Tyr Lys Ser Leu Leu Lys Ser
        290                 295                 300

<210> SEQ ID NO 4
<211> LENGTH: 280
<212> TYPE: PRT
<213> ORGANISM: Salmonella enterica

<400> SEQUENCE: 4

Met Gly Ala Ser Leu Ser Pro Gln Pro Asp Val Ser Gly Glu Leu Asn
1               5                   10                  15

Thr Glu Ala Leu Thr Cys Ile Val Glu Arg Leu Glu Ser Glu Ile Ile
            20                  25                  30

Asp Gly Ser Trp Ile His Ile Ser Tyr Glu Glu Thr Asp Leu Glu Met
        35                  40                  45

Met Pro Phe Leu Val Ala Gln Ala Asn Lys Lys Tyr Pro Glu Leu Asn
    50                  55                  60

Leu Lys Phe Val Met Ser Val His Glu Leu Val Ser Ser Ile Lys Glu
65                  70                  75                  80

Thr Arg Met Glu Gly Val Glu Ser Ala Arg Phe Leu Val Asn Met Gly
                85                  90                  95

Ser Ser Gly Ile His Ile Ser Val Val Asp Phe Arg Val Met Asp Gly
            100                 105                 110

Lys Thr Ser Val Ile Leu Phe Glu Pro Ala Ala Cys Ser Ala Phe Gly
        115                 120                 125

Pro Ala Leu Leu Ala Leu Arg Thr Lys Ala Ala Leu Glu Arg Glu Gln
    130                 135                 140

Leu Pro Asp Cys Tyr Phe Ala Met Val Glu Leu Asp Ile Gln Arg Ser
145                 150                 155                 160

Ser Ser Glu Cys Gly Ile Phe Ser Leu Ala Leu Ala Lys Lys Leu Gln
                165                 170                 175

Leu Glu Phe Met Asn Leu Val Lys Ile His Glu Asp Asn Ile Cys Glu
            180                 185                 190

Arg Leu Cys Gly Glu Pro Phe Leu Pro Ser Asp Lys Ala Asp Arg
        195                 200                 205

Tyr Leu Pro Val Ser Phe Tyr Lys His Thr Gln Gly Val Gln Arg Leu
    210                 215                 220

Asn Glu Tyr Val Glu Ala Asn Pro Ala Ala Gly Ser Ser Ile Val Asn
```

```
            225                 230                 235                 240
Lys Lys Asn Glu Thr Leu Tyr Glu Arg Phe Asp Asn Asn Ala Val Met
                245                 250                 255

Leu Asn Asp Lys Lys Leu Ser Ile Ser Ala His Lys Lys Arg Ile Ala
                260                 265                 270

Glu Tyr Lys Ser Leu Leu Lys Ser
                275                 280

<210> SEQ ID NO 5
<211> LENGTH: 302
<212> TYPE: PRT
<213> ORGANISM: Salmonella enterica

<400> SEQUENCE: 5

Met Ile Phe Ser Val Gln Glu Leu Ser Cys Gly Gly Lys Ser Met Leu
1               5                   10                  15

Ser Pro Thr Thr Arg Asn Met Gly Ala Ser Leu Ser Pro Gln Pro Asp
            20                  25                  30

Val Ser Gly Glu Leu Asn Thr Glu Ala Leu Thr Cys Ile Val Glu Arg
        35                  40                  45

Leu Glu Ser Glu Ile Ile Asp Gly Ser Trp Ile His Ile Ser Tyr Glu
    50                  55                  60

Glu Thr Asp Leu Glu Met Met Pro Phe Leu Val Ala Gln Ala Asn Lys
65                  70                  75                  80

Lys Tyr Pro Glu Leu Asn Leu Lys Phe Val Met Ser Val His Glu Leu
                85                  90                  95

Val Ser Ser Ile Lys Glu Thr Arg Met Glu Gly Val Glu Ser Ala Arg
            100                 105                 110

Phe Leu Val Asn Met Gly Ser Ser Gly Ile His Ile Ser Val Val Asp
        115                 120                 125

Phe Arg Val Met Asp Gly Lys Thr Ser Val Ile Leu Phe Glu Pro Ala
    130                 135                 140

Ala Cys Ser Ala Phe Gly Pro Ala Leu Leu Ala Leu Arg Thr Lys Ala
145                 150                 155                 160

Ala Leu Glu Arg Glu Gln Leu Pro Asp Cys Tyr Phe Ala Met Val Glu
                165                 170                 175

Leu Asp Ile Gln Arg Ser Ser Glu Cys Gly Ile Phe Ser Leu Ala
            180                 185                 190

Leu Ala Lys Lys Leu Gln Leu Glu Phe Met Asn Leu Val Lys Ile His
        195                 200                 205

Glu Asp Asn Ile Cys Glu Arg Leu Cys Gly Glu Pro Phe Leu Pro
    210                 215                 220

Ser Asp Lys Ala Asp Arg Tyr Leu Pro Val Ser Phe Tyr Lys His Thr
225                 230                 235                 240

Gln Gly Val Gln Arg Leu Asn Glu Tyr Val Glu Ala Asn Pro Ala Ala
                245                 250                 255

Gly Ser Ser Ile Val Asn Lys Asn Glu Thr Leu Tyr Glu Arg Phe
            260                 265                 270

Asp Asn Asn Ala Val Met Leu Asn Asp Lys Lys Leu Ser Ile Ser Ala
        275                 280                 285

His Lys Lys Arg Ile Ala Glu Tyr Lys Ser Leu Leu Lys Ser
    290                 295                 300

<210> SEQ ID NO 6
<211> LENGTH: 280
<212> TYPE: PRT
```

<213> ORGANISM: Salmonella enterica

<400> SEQUENCE: 6

Met Gly Ala Ser Leu Ser Pro Gln Pro Asp Val Ser Gly Glu Leu Asn
1               5                   10                  15

Thr Glu Ala Leu Thr Cys Ile Val Glu Arg Leu Glu Ser Glu Ile Ile
            20                  25                  30

Asp Gly Ser Trp Ile His Ile Ser Tyr Glu Glu Thr Asp Leu Glu Met
        35                  40                  45

Met Pro Phe Leu Val Ala Gln Ala Asn Lys Lys Tyr Pro Glu Leu Asn
    50                  55                  60

Leu Lys Phe Val Met Ser Val His Glu Leu Val Ser Ser Ile Lys Glu
65                  70                  75                  80

Thr Arg Met Glu Gly Val Glu Ser Ala Arg Phe Leu Val Asn Met Gly
                85                  90                  95

Ser Ser Gly Ile His Ile Ser Val Val Asp Phe Arg Val Met Asp Gly
            100                 105                 110

Lys Thr Ser Val Ile Leu Phe Glu Pro Ala Ala Cys Ser Ala Phe Gly
        115                 120                 125

Pro Ala Leu Leu Ala Leu Arg Thr Lys Ala Ala Leu Glu Arg Glu Gln
    130                 135                 140

Leu Pro Asp Cys Tyr Phe Ala Met Val Glu Leu Asp Ile Gln Arg Ser
145                 150                 155                 160

Ser Ser Glu Cys Gly Ile Phe Ser Leu Ala Leu Ala Lys Lys Leu Gln
                165                 170                 175

Leu Glu Phe Met Asn Leu Val Lys Ile His Glu Asp Asn Ile Cys Glu
            180                 185                 190

Arg Leu Cys Gly Glu Glu Pro Phe Leu Pro Ser Asp Lys Ala Asp Arg
        195                 200                 205

Tyr Leu Pro Val Ser Phe Tyr Lys His Thr Gln Gly Val Gln Arg Leu
    210                 215                 220

Asn Glu Tyr Val Glu Ala Asn Pro Ala Ala Gly Ser Ser Ile Val Asn
225                 230                 235                 240

Lys Lys Asn Glu Thr Leu Tyr Glu Arg Phe Asp Asn Asn Ala Val Met
                245                 250                 255

Leu Asn Asp Lys Lys Leu Ser Ile Ser Ala His Lys Lys Arg Ile Ala
            260                 265                 270

Glu Tyr Lys Ser Leu Leu Lys Pro
        275                 280

<210> SEQ ID NO 7
<211> LENGTH: 288
<212> TYPE: PRT
<213> ORGANISM: Salmonella enterica

<400> SEQUENCE: 7

Met Leu Ser Pro Thr Thr Arg Asn Met Gly Ala Ser Leu Ser Pro Gln
1               5                   10                  15

Pro Asp Val Ser Gly Glu Leu Asn Thr Glu Ala Leu Thr Cys Ile Val
            20                  25                  30

Glu Arg Leu Glu Ser Glu Ile Ile Asp Gly Ser Trp Ile His Ile Ser
        35                  40                  45

Tyr Glu Glu Thr Asp Leu Glu Met Met Pro Phe Leu Val Ala Gln Ala
    50                  55                  60

Asn Lys Lys Tyr Pro Glu Leu Asn Leu Lys Phe Val Met Ser Val His
65                  70                  75                  80

-continued

Glu Leu Val Ser Ser Ile Lys Glu Thr Arg Met Glu Gly Val Glu Ser
                85                  90                  95

Ala Arg Phe Leu Val Asn Met Gly Ser Ser Gly Ile His Ile Ser Val
            100                 105                 110

Val Asp Phe Arg Val Met Asp Gly Lys Thr Ser Val Ile Leu Phe Glu
        115                 120                 125

Pro Ala Ala Cys Ser Ala Phe Gly Pro Ala Leu Leu Ala Leu Arg Thr
    130                 135                 140

Lys Ala Ala Leu Glu Arg Glu Gln Leu Pro Asp Cys Tyr Phe Ala Met
145                 150                 155                 160

Val Glu Leu Asp Ile Gln Arg Ser Ser Glu Cys Gly Ile Phe Ser
                165                 170                 175

Leu Ala Leu Ala Lys Lys Leu Gln Leu Glu Phe Met Asn Leu Val Lys
            180                 185                 190

Ile His Glu Asp Asn Ile Cys Glu Arg Leu Cys Gly Glu Pro Phe
        195                 200                 205

Leu Pro Ser Asp Lys Ala Asp Arg Tyr Leu Pro Val Ser Phe Tyr Lys
    210                 215                 220

His Thr Gln Gly Val Gln Arg Leu Asn Glu Tyr Val Glu Ala Asn Pro
225                 230                 235                 240

Ala Ala Gly Ser Ser Ile Val Asn Lys Asn Glu Thr Leu Tyr Glu
                245                 250                 255

Arg Phe Asp Asn Asn Ala Val Met Leu Asn Asp Lys Lys Leu Ser Ile
            260                 265                 270

Phe Ala His Lys Lys Arg Ile Ala Glu Tyr Lys Ser Leu Leu Lys Pro
        275                 280                 285

<210> SEQ ID NO 8
<211> LENGTH: 288
<212> TYPE: PRT
<213> ORGANISM: Salmonella enterica

<400> SEQUENCE: 8

Met Leu Ser Pro Thr Thr Arg Asn Met Gly Ala Ser Leu Ser Pro Gln
1               5                   10                  15

Pro Asp Val Ser Gly Glu Leu Asn Thr Glu Ala Leu Thr Cys Ile Val
            20                  25                  30

Glu Arg Leu Glu Ser Glu Ile Ile Asp Gly Ser Trp Ile His Ile Ser
        35                  40                  45

Tyr Glu Glu Thr Asp Leu Glu Met Met Pro Phe Leu Val Ala Gln Ala
    50                  55                  60

Asn Lys Lys Tyr Pro Glu Leu Asn Leu Lys Phe Val Met Ser Val His
65                  70                  75                  80

Glu Leu Val Ser Ser Ile Lys Glu Thr Arg Met Glu Gly Val Glu Ser
                85                  90                  95

Ala Arg Phe Leu Val Asn Met Gly Ser Ser Gly Ile His Ile Ser Val
            100                 105                 110

Val Asp Phe Arg Val Met Asp Gly Lys Thr Ser Val Ile Leu Phe Glu
        115                 120                 125

Pro Ala Ala Cys Ser Ala Phe Gly Pro Ala Leu Leu Ala Leu Arg Thr
    130                 135                 140

Lys Ala Ala Leu Glu Arg Glu Gln Leu Pro Asp Cys Tyr Phe Ala Met
145                 150                 155                 160

Val Glu Leu Asp Ile Gln Arg Ser Ser Ser Glu Cys Gly Ile Phe Ser
                165                 170                 175

-continued

Leu Ala Leu Ala Lys Lys Leu Gln Leu Glu Phe Met Asn Leu Val Lys
            180                 185                 190

Ile His Glu Asp Asn Ile Cys Glu Arg Leu Cys Gly Glu Glu Pro Phe
            195                 200                 205

Leu Pro Ser Asp Lys Ala Asp Arg Tyr Leu Pro Val Ser Phe Tyr Lys
            210                 215                 220

His Thr Gln Gly Val Gln Arg Leu Asn Glu Tyr Val Gln Ala Asn Pro
225                 230                 235                 240

Ala Ala Gly Ser Ser Ile Val Asn Lys Lys Asn Glu Thr Leu Tyr Glu
                245                 250                 255

Arg Phe Asp Asn Asn Ala Val Met Leu Asn Asp Lys Lys Leu Ser Ile
            260                 265                 270

Ser Ala His Lys Lys Arg Ile Ala Glu Tyr Lys Ser Leu Leu Lys Pro
            275                 280                 285

<210> SEQ ID NO 9
<211> LENGTH: 288
<212> TYPE: PRT
<213> ORGANISM: Salmonella enterica

<400> SEQUENCE: 9

Met Leu Ser Pro Thr Thr Arg Asn Met Gly Ala Ser Leu Ser Pro Gln
1               5                   10                  15

Ser Asp Val Ser Gly Glu Leu Asn Thr Glu Ala Leu Thr Cys Ile Val
            20                  25                  30

Glu Arg Leu Glu Ser Glu Ile Ile Asp Gly Ser Trp Ile His Ile Ser
            35                  40                  45

Tyr Glu Glu Thr Asp Leu Glu Met Met Pro Phe Leu Val Ala Gln Ala
        50                  55                  60

Asn Lys Lys Tyr Pro Glu Leu Asn Leu Lys Phe Val Met Ser Val His
65                  70                  75                  80

Glu Leu Val Ser Ser Ile Lys Glu Thr Arg Met Glu Gly Val Glu Ser
                85                  90                  95

Ala Arg Phe Ile Val Asn Met Gly Ser Ser Gly Ile His Val Ser Val
            100                 105                 110

Val Asp Phe Arg Val Met Asp Gly Lys Thr Ser Val Ile Leu Phe Glu
            115                 120                 125

Pro Ala Ala Cys Ser Ala Phe Gly Pro Ala Leu Leu Ala Leu Arg Thr
130                 135                 140

Lys Ala Ala Leu Glu Arg Glu Gln Leu Pro Asp Cys Tyr Phe Ala Met
145                 150                 155                 160

Val Glu Leu Asp Ile Gln Arg Ser Ser Glu Cys Gly Ile Phe Ser
                165                 170                 175

Leu Ala Leu Ala Lys Lys Leu His Leu Glu Phe Met Asn Leu Val Lys
            180                 185                 190

Ile His Glu Asp Asn Ile Cys Glu Arg Leu Cys Gly Glu Pro Phe
            195                 200                 205

Leu Pro Ser Asp Lys Ala Asp Arg Tyr Leu Pro Val Ser Phe Tyr Lys
            210                 215                 220

His Thr Gln Gly Val Gln Arg Leu Asn Glu Tyr Val Gln Ala Asn Pro
225                 230                 235                 240

Ala Ala Gly Ser Ser Ile Val Asn Lys Lys Asn Glu Thr Leu Tyr Glu
                245                 250                 255

Arg Phe Asp Asn Asn Ala Val Met Leu Asn Asp Lys Lys Leu Ser Ile
            260                 265                 270

Ser Ala His Lys Lys Arg Ile Ala Glu Tyr Lys Ser Leu Leu Lys Pro
        275                 280                 285

<210> SEQ ID NO 10
<211> LENGTH: 906
<212> TYPE: DNA
<213> ORGANISM: Salmonella enterica

<400> SEQUENCE: 10

```
atgatatttt cggtgcagga gctatcatgt ggagggaaaa gtatgctaag tcctacgact      60
cgtaatatgg gggcgagttt atcgcctcag cctgacgtca gcggggagct aaacaccgaa     120
gcattgacct gtattgttga gcgtctggaa agtgaaatta gatggcag ctggattcat      180
atcagttacg aggaaaccga tctcgaaatg atgccttttc ttgttgcaca ggccaataag     240
aagtatccag agttaaatct taaatttgtt atgtcagtcc atgagcttgt ttcctctata     300
aaggagacca gaatggaagg cgttgaatct gcccgatttc tcgtaaatat gggaagttca     360
ggtatccata tttcagtcgt cgattttaga gttatggacg aaagacatc ggtgattttg     420
ttcgaaccag cagcgtgtag cgcttttgga cctgcactgg cgttgaggac aaagcagct    480
cttgaacgtg aacaactgcc tgattgttat tttgctatgg tcgagctgga cattcaacga     540
agctcttctg aatgcggtat ttttagcctg cgctcgcca aaaaacttca gcttgaattt     600
atgaacttag taaaaattca tgaagataat atttgtgaac gtctgtgtgg tgaagaacct     660
tttctcccgt ccgataaagc agaccgctat ctgccggtga ttttttacaa acatactcaa     720
ggcgcacaac gattaaatga atatgtggag gccaatccgg cggcgggaag cagtatagta     780
aacaaaaaga tgaaacgct ttatgagcga ttcgataaca atgccgttat gctaaacgat     840
aaaaaactct ctatatccgc tcataaaaaa aggatagctg aatataagtc tttacttaaa     900
ccgtaa                                                                906
```

<210> SEQ ID NO 11
<211> LENGTH: 909
<212> TYPE: DNA
<213> ORGANISM: Salmonella enterica

<400> SEQUENCE: 11

```
atgatatttt cggtgcagga gctatcatgt ggagggaaaa gtatgctaag tcctacgact      60
cgtaatatgg gggcgagttt atcgcctcag cctgacgtca gcggggagct aaacaccgaa     120
gcattgacct gtattgttga gcgtctggaa agtgaaatta gatggcag ctggattcat      180
atcagttacg aggaaaccga tctcgaaatg atgccttttc ttgttgcaca ggccaataag     240
aagtatccag agttaaatct taaatttgtt atgtcagtcc atgagcttgt ttcctctata     300
aaggagacca gaatggaagg cgttgaatct gcccgatttc tcgtaaatat gggaagttca     360
ggtatccata tttcagtcgt cgattttaga gttatggacg aaagacatc ggtgattttg     420
ttcgaaccag cagcgtgtag cgcttttgga cctgctttac tggcgttgag gaccaaagca    480
gctcttgaac gtgaacaact gcctgattgt tattttgcta tggtcgagct ggacattcaa     540
cgaagctctt ctgaatgcgg tattttttagc ctggcgctcg ccaaaaaact tcagcttgaa     600
tttatgaact tagtaaaaaat tcatgaagat aatatttgtg aacgtctgtg tggtgaagaa     660
ccttttctcc cgtccgataa agcagaccgc tatctgccgg tgagttttta caaacatact     720
caaggcgcac aacgattaaa tgaatatgtg gaggccaatc cggcggcggg aagcagtata     780
gtaaacaaaa agaatgaaac gctttatgag cgattcgata acaatgccgt tatgctaaac     840
```

| | |
|---|---|
| gataaaaaac tctctatatc cgctcataaa aaaaggatag ctgaatataa gtctttactt | 900 |
| aaaccgtaa | 909 |

<210> SEQ ID NO 12
<211> LENGTH: 909
<212> TYPE: DNA
<213> ORGANISM: Salmonella enterica

<400> SEQUENCE: 12

| | |
|---|---|
| atgatatttt cggtgcagga gctatcatgt ggagggaaaa gtatgctaag tcctacgact | 60 |
| cgtaatatgg gggcgagttt atcgcctcag cctgacgtca gcggggagct aaacaccgaa | 120 |
| gcattgacct gtattgttga gcgtctggaa agtgaaatta gatggcag ctggattcat | 180 |
| atcagttacg aggaaaccga tctcgaaatg atgcctttc ttgttgcaca ggccaataag | 240 |
| aagtatccag agttaaatct taaatttgtt atgtcagtcc atgagcttgt ttcctctata | 300 |
| aaggagacca gaatggaagg cgttgaatct gcccgatttc tcgtaaatat gggaagttca | 360 |
| ggtatccata tttcagtcgt cgattttaga gttatggacg aaagacatc ggtgattttg | 420 |
| ttcgaaccag cagcgtgtag cgcttttgga cctgctttac tggcgttgag gaccaaagca | 480 |
| gctcttgaac gtgaacaact gcctgattgt tattttgcta tggtcgagct ggacattcaa | 540 |
| cgaagctctt ctgaatgcgg tattttagc ctggcgctcg ccaaaaaact tcagcttgaa | 600 |
| tttatgaact tagtaaaaat tcatgaagat aatatttgtg aacgtctgtg tggtgaagaa | 660 |
| cctttttctcc cgtccgataa agcagaccgt tatctgccgg tgagttttta caaacatact | 720 |
| caaggcgtac aacgattaaa tgaatatgtg gaggccaatc cggcggcggg aagcagtata | 780 |
| gtaaacaaaa agaatgaaac gctttatgag cgattcgata acaatgccgt tatgctaaac | 840 |
| gataaaaaac tctctatatc cgctcataaa aaaaggatag ctgaatataa gtctttactt | 900 |
| aaatcgtaa | 909 |

<210> SEQ ID NO 13
<211> LENGTH: 843
<212> TYPE: DNA
<213> ORGANISM: Salmonella enterica

<400> SEQUENCE: 13

| | |
|---|---|
| atgggggcga gtttatcgcc tcagcctgac gtcagcgggg agctaaacac cgaagcattg | 60 |
| acctgtattg ttgagcgtct ggaaagtgaa attatagatg gcagctggat tcatatcagt | 120 |
| tacgaggaaa ccgatctcga aatgatgcct tttcttgttg cacaggccaa taagaagtat | 180 |
| ccagagttaa atcttaaatt tgttatgtca gtccatgagc ttgtttcctc tataaaggag | 240 |
| accagaatgg aaggcgttga atctgcccga tttctcgtaa atatgggaag ttcaggtatc | 300 |
| catatttcag tcgtcgattt tagagttatg gacggaaaga catcggtgat tttgttcgaa | 360 |
| ccagcagcgt gtagcgcttt tggacctgct ttactggcgt tgaggaccaa agcagctctt | 420 |
| gaacgtgaac aactgcctga ttgttatttt gctatggtcg agctggacat tcaacgaagc | 480 |
| tcttctgaat gcgtatttt tagcctggcg ctcgccaaaa aacttcagct tgaatttatg | 540 |
| aacttagtaa aaattcatga agataatatt tgtgaacgtc tgtgtggtga agaaccttt | 600 |
| ctcccgtccg ataaagcaga ccgttatctg ccggtgagtt tttacaaaca tactcaaggc | 660 |
| gtacaacgat taaatgaata tgtggaggcc aatccggcgg cgggaagcag tatagtaaac | 720 |
| aaaaagaatg aaacgcttta tgagcgattc gataacaatg ccgttatgct aaacgataaa | 780 |
| aaactctcta tatccgctca taaaaaaagg atagctgaat ataagtcttt acttaaatcg | 840 |

```
taa                                                                      843

<210> SEQ ID NO 14
<211> LENGTH: 909
<212> TYPE: DNA
<213> ORGANISM: Salmonella enterica

<400> SEQUENCE: 14
atgatatttt cggtgcagga gctatcatgt ggagggaaaa gtatgctaag tcctacgact     60
cgtaatatgg gggcgagttt atcgcctcag cctgacgtca gcgggagct aaacaccgaa     120 gcattgacct gtattgttga gcgtctggaa agtgaaatta tagatggcag ctggattcat    180
atcagttacg aggaaaccga tctcgaaatg atgccttttc ttgttgcaca ggccaataag    240
aagtatccag agttaaatct taaatttgtt atgtcagtcc atgagcttgt ttcctctata    300
aaggagacca gaatggaagg cgttgaatct gcccgatttc tcgtaaatat gggaagttca    360
ggtatccata tttcagtcgt cgattttaga gttatggacg aaagacatc ggtgattttg     420 ttcgaaccag cagcgtgtag cgcttttgga cctgctttac tggcgttgag gaccaaagca    480
gctcttgaac gtgaacaact gcctgattgt tattttgcta tggtcgagct ggacattcaa    540
cgaagctctt ctgaatgcgg tattttagc ctggcgctcg ccaaaaaact tcagcttgaa     600
tttatgaact agtaaaaat tcatgaagat aatatttgtg aacgtctgtg tggtgaagaa    660
ccttttctcc cgtccgataa agcagaccgt tatctgccgg tgagttttta caaacatact    720
caaggcgtac aacgattaaa tgaatatgtg gaggccaatc cggcggcggg aagcagtata    780
gtaaacaaaa agaatgaaac gctttatgag cgattcgata caatgccgt tatgctaaac     840 gataaaaaac tctctatatc cgctcataaa aaaggatag ctgaatataa gtctttactt     900
aaatcgtaa                                                            909

<210> SEQ ID NO 15
<211> LENGTH: 843
<212> TYPE: DNA
<213> ORGANISM: Salmonella enterica

<400> SEQUENCE: 15
atgggggcga gtttatcgcc tcagcctgac gtcagcgggg agctaaacac cgaagcattg     60
acctgtattg ttgagcgtct ggaaagtgaa attatagatg cagctggat tcatatcagt    120 tacgaggaaa ccgatctcga aatgatgcct tttcttgttg cacaggccaa taagaagtat    180
ccagagttaa atcttaaatt tgttatgtca gtccatgagc ttgtttcctc tataaaggag    240
accagaatgg aaggcgttga atctgcccga tttctcgtaa atatgggaag ttcaggtatc    300
catatttcag tcgtcgattt tagagttatg acggaaaga catcggtgat tttgttcgaa    360
ccagcagcgt gtagcgcttt tggacctgct ttactggcgt tgaggaccaa agcagctctt    420
gaacgtgaac aactgcctga ttgttatttt gctatggtcg agctggacat tcaacgaagc    480
tcttctgaat gcggtatttt agcctggcg ctcgccaaaa aacttcagct tgaatttatg     540
aacttagtaa aaattcatga agataatatt tgtaacgtc tgtgtggtga agaaccttt     600 ctcccgtccg ataaagcaga ccgctatctg ccggtgagtt tttacaaaca tactcaaggc    660
gtacaacgat aaatgaata tgtggaggcc aatccggcgg cgggaagcag tatagtaaac    720 aaaagaatg aaacgcttta tgagcgattc gataacaatg ccgttatgct aaacgataaa    780
aaactctcta tatccgctca taaaaaaagg atagctgaat ataagtcttt acttaaaccg    840
taa                                                                  843
```

<210> SEQ ID NO 16
<211> LENGTH: 867
<212> TYPE: DNA
<213> ORGANISM: Salmonella enterica

<400> SEQUENCE: 16

| | | | | | | |
|---|---|---|---|---|---|---|
| atgctaagtc | ctacgactcg | taatatgggg | gcgagtttat | cgcctcagcc | tgacgtcagc | 60 |
| ggggagctaa | acaccgaagc | attgacctgt | attgttgagc | gtctggaaag | tgaaattata | 120 |
| gatggcagct | ggattcatat | cagttacgag | gaaaccgatc | tcgaaatgat | gccttttctt | 180 |
| gttgcacagg | ccaataagaa | gtatccagag | ttaaatctta | aatttgttat | gtcagtccat | 240 |
| gagcttgttt | cctctataaa | ggagaccaga | atggaaggcg | ttgaatctgc | ccgatttctc | 300 |
| gtaaatatgg | gaagttcagg | tatccatatt | tcagtcgtcg | attttagagt | tatggacgga | 360 |
| aagacatcgg | tgattttgtt | cgaaccagca | gcgtgtagcg | cttttggacc | tgctttactg | 420 |
| gcgttgagga | ccaaagcagc | tcttgaacgt | gaacaactgc | ctgattgtta | ttttgctatg | 480 |
| gtcgagctgg | acattcaacg | aagctcttct | gaatgcggta | tttttagcct | ggcgctcgcc | 540 |
| aaaaaacttc | agcttgaatt | tatgaactta | gtaaaaattc | atgaagataa | tatttgtgaa | 600 |
| cgtctgtgtg | gtgaagaacc | ttttctcccg | tccgataaag | cagaccgcta | tctgccggtg | 660 |
| agttttttaca | aacatactca | aggcgtacaa | cgattaaatg | aatatgtgga | ggccaatccg | 720 |
| gcggcgggaa | gcagtatagt | aaacaaaaag | aatgaaacgc | tttatgagcg | attcgataac | 780 |
| aatgccgtta | tgctaaacga | taaaaaactc | tctatattcg | ctcataaaaa | aaggatagct | 840 |
| gaatataagt | ctttacttaa | accgtaa | | | | 867 |

<210> SEQ ID NO 17
<211> LENGTH: 867
<212> TYPE: DNA
<213> ORGANISM: Salmonella enterica

<400> SEQUENCE: 17

| | | | | | | |
|---|---|---|---|---|---|---|
| atgctaagtc | ctacgactcg | taatatgggg | gcgagtttat | cgcctcagcc | tgacgtcagc | 60 |
| ggggagctaa | acaccgaagc | attgacctgt | attgttgagc | gtctggaaag | tgaaattata | 120 |
| gatggcagct | ggattcatat | cagttacgag | gaaaccgatc | tcgaaatgat | gccttttctt | 180 |
| gttgcacagg | ccaataagaa | gtatccagag | ttaaatctta | aatttgttat | gtcagtccat | 240 |
| gagcttgttt | cctctataaa | ggagaccaga | atggaaggcg | ttgaatctgc | ccgatttctc | 300 |
| gtaaatatgg | gaagttcagg | tatccatatt | tcagtcgtcg | attttagagt | tatggacgga | 360 |
| aagacatcgg | tgattttgtt | cgaaccagca | gcgtgtagcg | cttttggacc | tgctttactg | 420 |
| gcgttgagga | ccaaagcagc | tcttgaacgt | gaacaactgc | ctgattgtta | ttttgctatg | 480 |
| gtcgagctgg | acattcaacg | aagctcttct | gaatgtggta | tttttagcct | ggcgctcgcc | 540 |
| aaaaaacttc | agcttgaatt | tatgaactta | gtaaaaattc | atgaagataa | tatttgtgaa | 600 |
| cgtctgtgtg | gtgaagaacc | ttttctcccg | tctgataaag | cagaccgtta | tctgccggtg | 660 |
| agttttttaca | aacatactca | aggcgtacaa | cgattaaatg | aatatgtgca | ggccaatccg | 720 |
| gcggcgggaa | gcagtatagt | aaacaaaaag | aatgaaacgc | tttatgagcg | attcgataac | 780 |
| aatgccgtta | tgctaaacga | taaaaaactc | tctatatccg | ctcataaaaa | aaggatagct | 840 |
| gaatataagt | ctttgcttaa | accgtaa | | | | 867 |

<210> SEQ ID NO 18
<211> LENGTH: 867
<212> TYPE: DNA

-continued

<213> ORGANISM: Salmonella enterica

<400> SEQUENCE: 18

```
atgctaagtc ctacgactcg taatatgggg gcgagtttat cgcctcagtc tgacgtcagc    60
ggggagctaa acaccgaagc attgacctgt attgttgagc gtctggaaag tgaaattata   120
gatggcagct ggattcatat cagttacgag gaaaccgatc tcgaaatgat gccttttctt   180
gttgcacagg ccaataagaa gtatccgagg ttaaatctta aatttgttat gtcagtccat   240
gagcttgttt cctctataaa ggagaccaga atggaaggcg ttgaatctgc ccgatttatc   300
gtaaatatgg gaagttcagg tatccatgtt tcagtcgtcg attttagagt tatggacgga   360
aagacatcgg tgattttgtt cgaaccagca gcgtgtagcg cttttggacc tgctttactg   420
gcattgagga ccaaagcagc tcttgaacgt gaacaattgc ctgattgtta ttttgctatg   480
gtcgagctgg acattcaacg aagctcttct gaatgcggta tttttagcct ggcgctcgcc   540
aaaaaacttc atcttgaatt tatgaactta gtaaaaattc atgaagataa tatttgtgaa   600
cgtctgtgtg gtgaagaacc ttttctcccg tccgataaag cagaccgcta tctgccggtg   660
agtttttaca acatactca aggcgtacaa cgattaaatg aatatgtgca ggccaatccg   720
gcggcgggaa gcagtatagt aaacaaaaag aatgaaacgc tttatgagcg attcgataac   780
aatgccgtta tgctaaacga taaaaaactc tctatatccg ctcataaaaa aggatagct   840
gaatataagt ctttacttaa accgtaa                                       867
```

<210> SEQ ID NO 19
<211> LENGTH: 302
<212> TYPE: PRT
<213> ORGANISM: Artificial
<220> FEATURE:
<223> OTHER INFORMATION: AvrA consensus
<220> FEATURE:
<221> NAME/KEY: MISC_FEATURE
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (114)..(114)
<223> OTHER INFORMATION: Xaa can be any naturally occurring amino acid
<220> FEATURE:
<221> NAME/KEY: MISC_FEATURE
<222> LOCATION: (124)..(124)
<223> OTHER INFORMATION: Xaa can be any naturally occurring amino acid
<220> FEATURE:
<221> NAME/KEY: MISC_FEATURE
<222> LOCATION: (153)..(153)
<223> OTHER INFORMATION: Xaa is optional and can be any naturally
      occurring amino acid
<220> FEATURE:
<221> NAME/KEY: MISC_FEATURE
<222> LOCATION: (198)..(198)
<223> OTHER INFORMATION: Xaa can be any naturally occurring amino acid
<220> FEATURE:
<221> NAME/KEY: MISC_FEATURE
<222> LOCATION: (243)..(243)
<223> OTHER INFORMATION: Xaa can be any naturally occurring amino acid
<220> FEATURE:
<221> NAME/KEY: MISC_FEATURE
<222> LOCATION: (251)..(251)
<223> OTHER INFORMATION: Xaa can be any naturally occurring amino acid
<220> FEATURE:
<221> NAME/KEY: MISC_FEATURE
<222> LOCATION: (287)..(287)
<223> OTHER INFORMATION: Xaa can be any naturally occurring amino acid
<220> FEATURE:
<221> NAME/KEY: MISC_FEATURE
<222> LOCATION: (302)..(302)
<223> OTHER INFORMATION: Xaa can be any naturally occurring amino acid

<400> SEQUENCE: 19

-continued

```
Met Ile Phe Ser Val Gln Glu Leu Ser Cys Gly Gly Lys Ser Met Leu
1               5                   10                  15

Ser Pro Thr Thr Arg Asn Met Gly Ala Ser Leu Ser Pro Gln Xaa Asp
            20                  25                  30

Val Ser Gly Glu Leu Asn Thr Glu Ala Leu Thr Cys Ile Val Glu Arg
        35                  40                  45

Leu Glu Ser Glu Ile Ile Asp Gly Ser Trp Ile His Ile Ser Tyr Glu
    50                  55                  60

Glu Thr Asp Leu Glu Met Met Pro Phe Leu Val Ala Gln Ala Asn Lys
65                  70                  75                  80

Lys Tyr Pro Glu Leu Asn Leu Lys Phe Val Met Ser Val His Glu Leu
                85                  90                  95

Val Ser Ser Ile Lys Glu Thr Arg Met Glu Gly Val Glu Ser Ala Arg
            100                 105                 110

Phe Xaa Val Asn Met Gly Ser Ser Gly Ile His Xaa Ser Val Val Asp
        115                 120                 125

Phe Arg Val Met Asp Gly Lys Thr Ser Val Ile Leu Phe Glu Pro Ala
    130                 135                 140

Ala Cys Ser Ala Phe Gly Pro Ala Xaa Leu Ala Leu Arg Thr Lys Ala
145                 150                 155                 160

Ala Leu Glu Arg Glu Gln Leu Pro Asp Cys Tyr Phe Ala Met Val Glu
                165                 170                 175

Leu Asp Ile Gln Arg Ser Ser Ser Glu Cys Gly Ile Phe Ser Leu Ala
            180                 185                 190

Leu Ala Lys Lys Leu Xaa Leu Glu Phe Met Asn Leu Val Lys Ile His
        195                 200                 205

Glu Asp Asn Ile Cys Glu Arg Leu Cys Gly Glu Glu Pro Phe Leu Pro
    210                 215                 220

Ser Asp Lys Ala Asp Arg Tyr Leu Pro Val Ser Phe Tyr Lys His Thr
225                 230                 235                 240

Gln Gly Xaa Gln Arg Leu Asn Glu Tyr Val Xaa Ala Asn Pro Ala Ala
                245                 250                 255

Gly Ser Ser Ile Val Asn Lys Lys Asn Glu Thr Leu Tyr Glu Arg Phe
            260                 265                 270

Asp Asn Asn Ala Val Met Leu Asn Asp Lys Lys Leu Ser Ile Xaa Ala
        275                 280                 285

His Lys Lys Arg Ile Ala Glu Tyr Lys Ser Leu Leu Lys Xaa
    290                 295                 300
```